(12) United States Patent
Tybinkowski et al.

(10) Patent No.: US 8,905,637 B2
(45) Date of Patent: Dec. 9, 2014

(54) X-RAY TRANSPARENT BED AND GURNEY EXTENDER FOR USE WITH MOBILE COMPUTERIZED TOMOGRAPHY (CT) IMAGING SYSTEMS

(75) Inventors: Andrew P. Tybinkowski, Boxford, MA (US); Lidia Nemirovsky, Salem, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

(21) Appl. No.: 12/574,476

(22) Filed: Oct. 6, 2009

(65) Prior Publication Data

US 2010/0205740 A1   Aug. 19, 2010

Related U.S. Application Data

(63) Continuation-in-part of application No. 11/706,133, filed on Feb. 13, 2007, now Pat. No. 7,637,660, which is a continuation of application No. 11/193,941, filed on Jul. 29, 2005, now Pat. No. 7,175,347, said application No. 12/574,476 is a continuation-in-part of application No. 11/803,241, filed on May 14, 2007, now Pat. No. 7,736,056.

(60) Provisional application No. 60/670,164, filed on Apr. 11, 2005, provisional application No. 60/593,001, filed on Jul. 30, 2004, provisional application No. 61/195,287, filed on Oct. 6, 2008.

(51) Int. Cl.
| | |
|---|---|
| *A61B 6/04* | (2006.01) |
| *A61B 6/00* | (2006.01) |
| *G01N 23/04* | (2006.01) |
| *A61B 6/03* | (2006.01) |

(52) U.S. Cl.
CPC ............... *A61B 6/4405* (2013.01); *A61B 6/04* (2013.01); *G01N 23/046* (2013.01); *A61B 6/508* (2013.01); *A61B 6/032* (2013.01)
USPC ................................ 378/209; 5/601

(58) Field of Classification Search
USPC .................. 378/208–209; 5/600, 601, 605
See application file for complete search history.

(56) References Cited

U.S. PATENT DOCUMENTS

| | | |
|---|---|---|
| 3,603,975 A | 9/1971 | Gordon |
| 3,631,241 A | 12/1971 | Franke et al. |
| 3,775,612 A | 11/1973 | Foster et al. |
| 3,904,878 A | 9/1975 | Burch et al. |
| 4,006,359 A | 2/1977 | Sullins et al. |
| 4,064,401 A | 12/1977 | Marden |
| 4,105,923 A * | 8/1978 | Hynes, Jr. ...................... 378/20 |
| 4,131,802 A | 12/1978 | Braden et al. |
| 4,409,695 A * | 10/1983 | Johnston et al. ................ 5/601 |
| 4,506,872 A | 3/1985 | Westerberg et al. |
| 4,688,780 A | 8/1987 | Hanz |

(Continued)

FOREIGN PATENT DOCUMENTS

| | | |
|---|---|---|
| CN | 1037450 | 11/1989 |
| DE | 29 38 261 A1 | 4/1981 |

(Continued)

*Primary Examiner* — Hoon Song
(74) *Attorney, Agent, or Firm* — Pandiscio & Pandiscio

(57) ABSTRACT

A support for supporting anatomy of a patient during scanning, comprising:
  a holder for supporting anatomy of a patient during scanning, wherein at least a portion of the holder is X-ray transparent; and
  a support for supporting the holder adjacent to a scanner.

12 Claims, 71 Drawing Sheets

(56) References Cited

U.S. PATENT DOCUMENTS

| | | | |
|---|---|---|---|
| 4,928,283 A | 5/1990 | Gordon | |
| 4,971,037 A | 11/1990 | Pelta | |
| 4,989,849 A | 2/1991 | Zupancic et al. | |
| 5,054,141 A * | 10/1991 | Foster et al. | 5/611 |
| 5,233,713 A | 8/1993 | Murphy et al. | |
| 5,422,928 A | 6/1995 | Payne | |
| 5,448,607 A | 9/1995 | McKenna | |
| 5,675,851 A | 10/1997 | Feathers | |
| 5,771,513 A | 6/1998 | Kirchgeorg et al. | |
| 5,867,553 A | 2/1999 | Gordon et al. | |
| 5,887,047 A | 3/1999 | Bailey et al. | |
| 5,982,843 A | 11/1999 | Bailey et al. | |
| 6,108,396 A | 8/2000 | Bechwati et al. | |
| 6,144,180 A | 11/2000 | Chen et al. | |
| 6,199,233 B1 * | 3/2001 | Kantrowitz et al. | 5/601 |
| 6,212,251 B1 | 4/2001 | Tomura et al. | |
| 6,217,214 B1 | 4/2001 | Cabral et al. | |
| 6,256,404 B1 | 7/2001 | Gordon et al. | |
| 6,285,028 B1 | 9/2001 | Yamakawa | |
| 6,295,671 B1 | 10/2001 | Reesby et al. | |
| 6,374,937 B1 | 4/2002 | Galando et al. | |
| 6,396,902 B2 | 5/2002 | Tybinkowski et al. | |
| 6,459,923 B1 | 10/2002 | Plewes et al. | |
| 6,470,068 B2 | 10/2002 | Cheng | |
| 6,705,758 B1 | 3/2004 | Luusua et al. | |
| 6,813,374 B1 | 11/2004 | Karimi et al. | |
| 6,857,778 B2 | 2/2005 | Mun et al. | |
| 6,926,441 B2 | 8/2005 | Stout, Jr. | |
| 6,959,068 B1 | 10/2005 | Sommer | |
| 7,175,347 B2 | 2/2007 | Tybinkowski et al. | |
| 7,319,738 B2 | 1/2008 | Lasiuk et al. | |
| 7,338,207 B2 | 3/2008 | Gregerson et al. | |
| 7,676,255 B2 | 3/2010 | Wang et al. | |
| 7,736,056 B2 | 6/2010 | Tybinkowski et al. | |
| 8,118,488 B2 | 2/2012 | Gregerson | |
| 8,292,505 B2 | 10/2012 | Tybinkowski et al. | |
| 2002/0035317 A1 | 3/2002 | Cheng et al. | |
| 2002/0039403 A1 | 4/2002 | Oota | |
| 2002/0138904 A1 * | 10/2002 | Wong | 5/600 |
| 2002/0152551 A1 * | 10/2002 | Perez et al. | 5/600 |
| 2003/0072613 A1 | 4/2003 | Colvard | |
| 2003/0084512 A1 | 5/2003 | Fujita et al. | |
| 2003/0095635 A1 | 5/2003 | Moritake et al. | |
| 2004/0055089 A1 | 3/2004 | Dinkler et al. | |
| 2004/0158926 A1 | 8/2004 | Stevens | |
| 2005/0135560 A1 | 6/2005 | Dafni et al. | |
| 2005/0284672 A1 | 12/2005 | Egen et al. | |
| 2006/0083354 A1 | 4/2006 | Tybinkowski et al. | |
| 2006/0083355 A1 | 4/2006 | Loser | |
| 2007/0183588 A1 | 8/2007 | Bailey et al. | |
| 2007/0183589 A1 | 8/2007 | Tybinkowski et al. | |
| 2007/0195938 A1 | 8/2007 | Bailey et al. | |
| 2008/0008290 A1 | 1/2008 | Tybinkowski et al. | |
| 2010/0172468 A1 | 7/2010 | Gregerson | |
| 2011/0222667 A1 | 9/2011 | Gregerson et al. | |
| 2011/0228910 A1 | 9/2011 | Gregerson et al. | |
| 2012/0256099 A1 | 10/2012 | Gregerson et al. | |
| 2012/0330087 A1 | 12/2012 | Gregerson | |

FOREIGN PATENT DOCUMENTS

| | | |
|---|---|---|
| DE | 44 06 493 A1 | 8/1995 |
| DE | 297 06 436 | 5/1997 |
| GB | 2 405 789 | 3/2005 |
| JP | HEI 11-164829 | 6/1999 |
| JP | 2003-190149 | 7/2003 |
| WO | WO 98/00681 | 7/1999 |
| WO | WO 2005/004723 | 1/2005 |
| WO | WO 2006/013185 | 2/2006 |

* cited by examiner

US 8,905,637 B2

X-RAY TRANSPARENT BED AND GURNEY EXTENDER FOR USE WITH MOBILE COMPUTERIZED TOMOGRAPHY (CT) IMAGING SYSTEMS

REFERENCE TO PENDING PRIOR PATENT APPLICATIONS

This patent application:

(i) is a continuation-in-part of prior U.S. patent application Ser. No. 11/706,133, filed Feb. 13, 2007 now U.S. Pat. No. 7,637,660 by Andrew P. Tybinkowski et al. for ANATOMICAL IMAGING SYSTEM WITH CENTIPEDE BELT DRIVE, which patent application is in turn a continuation of U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE BELT DRIVE, which patent application in turn claims benefit of (i) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE, and (ii) prior U.S. Provisional Patent Application Ser. No. 60/593,001, filed Jul. 30, 2004 by Bernard Gordon et al. for ANATOMICAL SCANNING SYSTEM;

(ii) is a continuation-in-part of prior U.S. patent application Ser. No. 11/803,241, filed May 14, 2007 now U.S. Pat. No. 7,736,056 by Andrew P. Tybinkowski et al. for X-RAY TRANSPARENT BED AND GURNEY EXTENDER FOR USE WITH MOBILE COMPUTERIZED TOMOGRAPHY (CT) IMAGING SYSTEMS; and (iii) claims benefit of prior U.S. Provisional Patent Application Ser. No. 61/195,287 filed Oct. 6, 2008 by Andrew P. Tybinkowski et al. for X-RAY TRANSPARENT BED AND GURNEY EXTENDER FOR USE WITH MOBILE COMPUTERIZED TOMOGRAPHY (CT) IMAGING SYSTEMS.

The six (6) above-identified patent applications are hereby incorporated herein by reference.

FIELD OF THE INVENTION

This invention relates to anatomical imaging systems in general, and more particularly to mobile Computerized Tomography (CT) imaging systems and X-ray transparent bed and gurney extenders for use with the same.

BACKGROUND OF THE INVENTION

Strokes are the third leading cause of death in the United States, causing approximately 177,000 deaths per year, and strokes are the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT scanners generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning (including non-enhanced CT scanning, CT angiography scanning and CT perfusion scanning) is able to provide substantially all of the information needed to effectively diagnose (and hence properly treat) a stroke.

Unfortunately, in practice, the CT machine is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient.

For this reason, as well as others, NeuroLogica Corporation of Danvers, Mass. has recently developed a mobile CT imaging system, i.e., the CereTom™ CT machine. The CereTom™ CT machine is particularly well suited for use in stroke applications. More particularly, the CereTom™ CT machine is a small, mobile CT machine which can be pre-positioned in the emergency room and moved to the patient so that the patient can be scanned at their current location, on their emergency room bed or gurney, thus effectively eliminating "round-trip" delays between the emergency room and radiology department and thereby dramatically reducing the time needed to properly diagnose the patient.

The CereTom™ CT machine also has application in numerous other situations where patients may be located remote from the CT machine, e.g., other hospital departments such as Intensive Care Units (ICUs), nursing homes, rehabilitation centers, etc.

Since the CereTom™ CT machine is designed to be as small and mobile as possible, and since the CereTom™ CT machine is intended primarily for stroke applications and thus need only scan the head of the patient, it is configured so as to have a relatively small-diameter scan opening, i.e., a scan opening just large enough to receive the head of the patient. Furthermore, since the beds and gurneys typically found in emergency rooms are too large to fit within the scan opening of the CereTom™ CT machine, there is an urgent need for a narrow, X-ray transparent extender for selective attachment to the bed or gurney so as to support the patient's head during scanning, whereby the patient can be quickly and easily scanned while remaining on their bed or gurney.

There is also a need for a narrow, X-ray transparent support for supporting the anatomy of a patient during scanning, whereby the patient can be quickly and easily scanned at their current location without requiring transportation to another location.

SUMMARY OF THE INVENTION

These and other objects of the present invention are addressed by the provision and use of a narrow, X-ray transparent extender for selective attachment to a bed or gurney so as to support a patient's head during scanning, whereby a patient can be quickly and easily scanned while remaining on their bed or gurney.

And these and other objects of the present invention are addressed by the provision and use of a narrow, X-ray transparent support for supporting the anatomy of a patient during scanning, whereby the patient can be quickly and easily scanned at their current location without requiring transportation to another location.

In accordance with the present invention, there is provided a bed and gurney extender for selective attachment to a standard hospital bed or gurney for supporting the head of a patient during scanning, comprising:

a support for supporting the head of the patient during scanning, wherein at least a portion of the support is X-ray transparent; and an adapter for selectively attaching the support to the bed or gurney.

In another form of the invention, there is provided apparatus for use in scanning a patient on a bed or gurney, comprising:

a bed and gurney extender for selective attachment to a standard hospital bed or gurney for supporting the head of the patient during scanning, comprising:

a support for supporting the head of the patient during scanning, wherein at least a portion of the support is X-ray transparent; and an adapter for selectively attaching the support to the bed or gurney.

In another form of the invention, there is provided a method for scanning a patient, comprising:

mounting an extender to the bed or gurney of the patient so as to present the head of the patient on an X-ray transparent support remote from the remainder of the bed or gurney;

positioning the head of the patient adjacent to the scanning zone of a scanner; and moving the scanner precisely relative to the patient during scanning while the head of the patient remains disposed on the X-ray transparent support.

In another form of the invention, there is provided a bed and gurney extender for selective attachment to a bed or gurney for supporting the head of a patient during scanning, comprising:

a support for supporting the head of the patient during scanning, wherein at least a portion of the support is transparent to the scanner; and an adapter for selectively attaching the support to the bed or gurney.

In another form of the invention, there is a provided apparatus for use in scanning a patient on a bed or gurney, comprising:

a bed and gurney extender for selective attachment to a bed or gurney for supporting the head of the patient during scanning, comprising:

a support for supporting the head of the patient during scanning, wherein at least a portion of the support is transparent to the scanner; and an adapter for selectively attaching the support to the bed or gurney.

In another form of the invention, there is provided a method for scanning a patient, comprising:

mounting an extender to the bed or gurney of the patient so as to present the head of the patient on a support remote from the remainder of the bed or gurney, wherein the support is transparent to the scanner;

positioning the head of the patient adjacent to the scanning zone of a scanner; and moving the scanner precisely relative to the patient during scanning while the head of the patient remains disposed on the scanner-transparent support.

In another preferred form of the invention, there is provided an extender for selective attachment to a standard operating table or like patient-supporting platform for supporting anatomy of a patient during scanning, comprising:

a support for supporting anatomy of a patient during scanning, wherein at least a portion of the support is transparent to the scanner; and an adapter for selectively attaching the support to the standard operating table or like patient-supporting platform.

In another preferred form of the invention, there is provided apparatus for use in scanning a patient on a standard operating table or like patient-supporting platform, comprising:

an extender for selective attachment to a standard operating table or like patient-supporting platform for supporting anatomy of a patient during scanning, the extender comprising:

a support for supporting anatomy of a patient during scanning, wherein at least a portion of the support is transparent to the scanner; and an adapter for selectively attaching the support to the standard operating table or like patient-supporting platform.

In another preferred form of the invention, there is provided a method for scanning a patient, comprising:

mounting an extender to a standard operating table or like patient-supporting platform supporting a patient so as to present anatomy of a patient on a support transparent to the scanner, wherein the support is remote from the remainder of the standard operating table or like patient-supporting platform;

positioning anatomy of a patient adjacent to the scanning zone of a scanner; and moving the scanner relative to a patient during scanning while anatomy of a patient remains disposed on the support which is transparent to the scanner.

In another preferred form of the invention, there is provided apparatus for use in scanning a patient, the apparatus comprising:

a free-standing support for supporting anatomy of a patient during scanning, the free-standing support comprising:

a holder for supporting anatomy of a patient during scanning, wherein at least a portion of the holder is transparent to the scanner; and a movable stand, the movable stand comprising a riser terminating in a head at its upper end and a base at its lower end, the holder being attached to the head, and the base comprising a plurality of casters which permit the movable stand to move about on a floor, and at least one brake for selectively stopping movement of the movable stand on a floor.

In another preferred form of the invention, there is provided a method for scanning a patient, comprising:
providing apparatus for use in scanning a patient, the apparatus comprising:
a free-standing support for supporting anatomy of a patient during scanning, the free-standing support comprising:
a holder for supporting anatomy of a patient during scanning, wherein at least a portion of the holder is transparent to the scanner; and
a movable stand, the movable stand comprising a riser terminating in a head at its upper end and a base at its lower end, the holder being attached to the head, and the base comprising a plurality of casters which permit the movable stand to move about on a floor, and at least one brake for selectively stopping movement of the movable stand on a floor;
positioning the free-standing support adjacent the scanner;
positioning anatomy of a patient on the holder; and
moving the scanner relative to a patient during scanning while anatomy of a patient remains disposed on the holder which is transparent to the scanner.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

CereTom™ CT Machine

Figure 1:
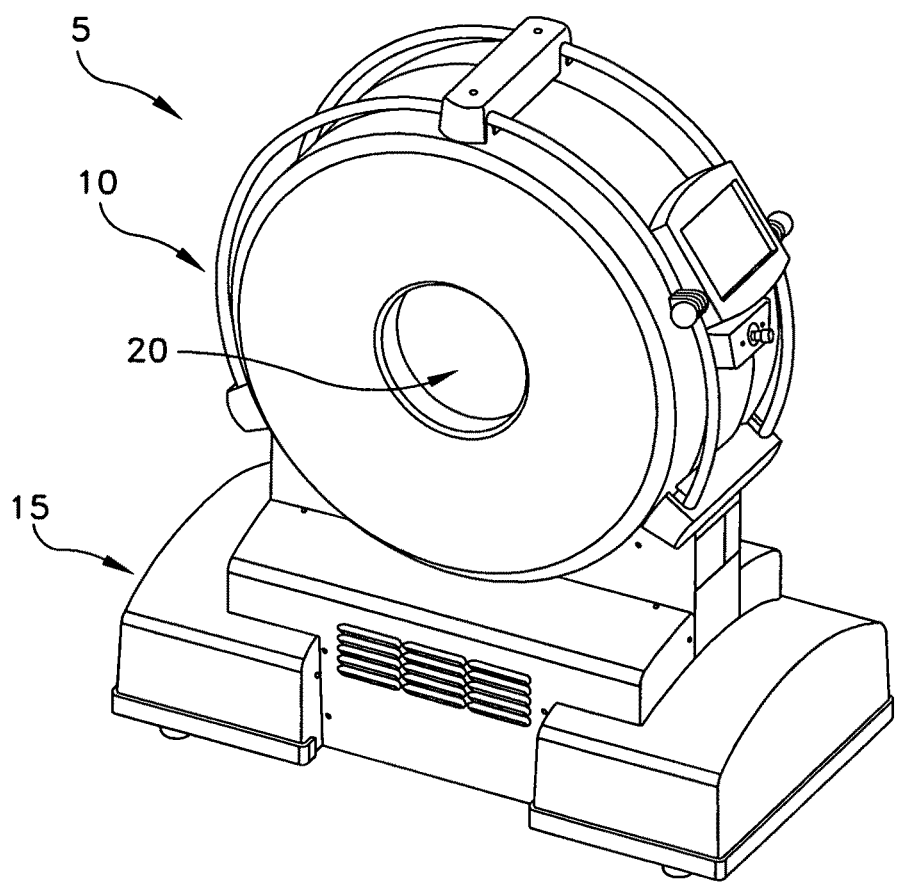
FIGS. 1 and 2 are schematic external views of a CereTom™ CT machine.
Figure 2:
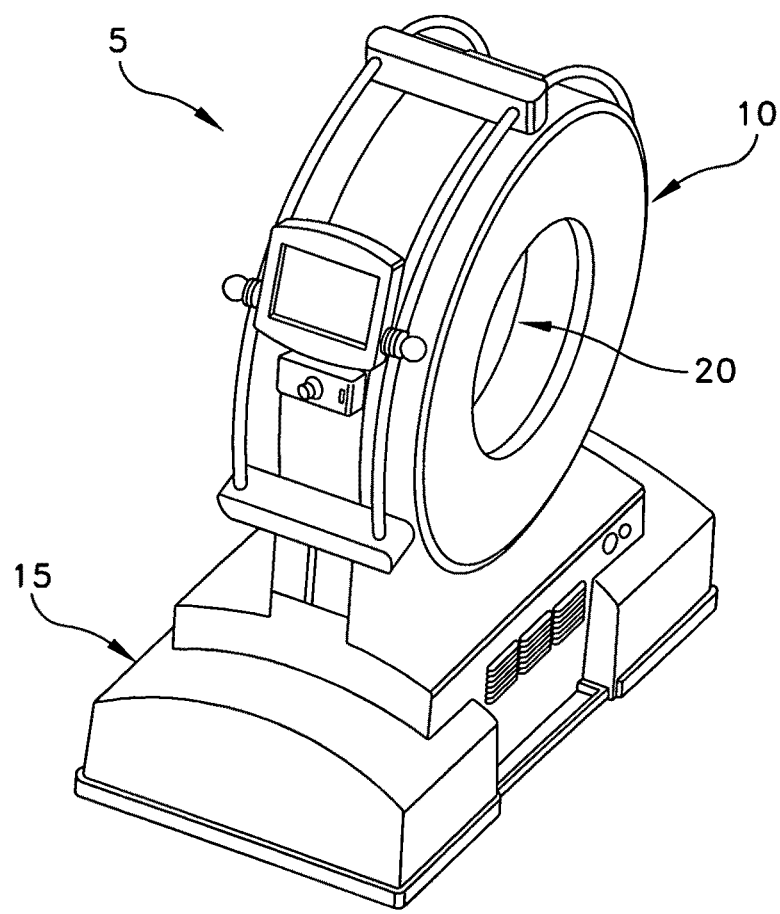

Looking first at FIGS. 1 and 2, there is shown a CereTom™ CT machine 5. CereTom™ CT machine 5 generally comprises a torus 10 which is supported by a base 15. A center opening 20 is formed in torus 10. Center opening 20 receives the patient anatomy which is to be scanned. Since CereTom™ CT machine 5 is designed to be as small and mobile as possible, and since CereTom™ CT machine 5 is intended primarily for stroke applications and thus need only scan the head of the patient, center opening 20 is configured to be just slightly larger than the head of the patient.

Figure 3:
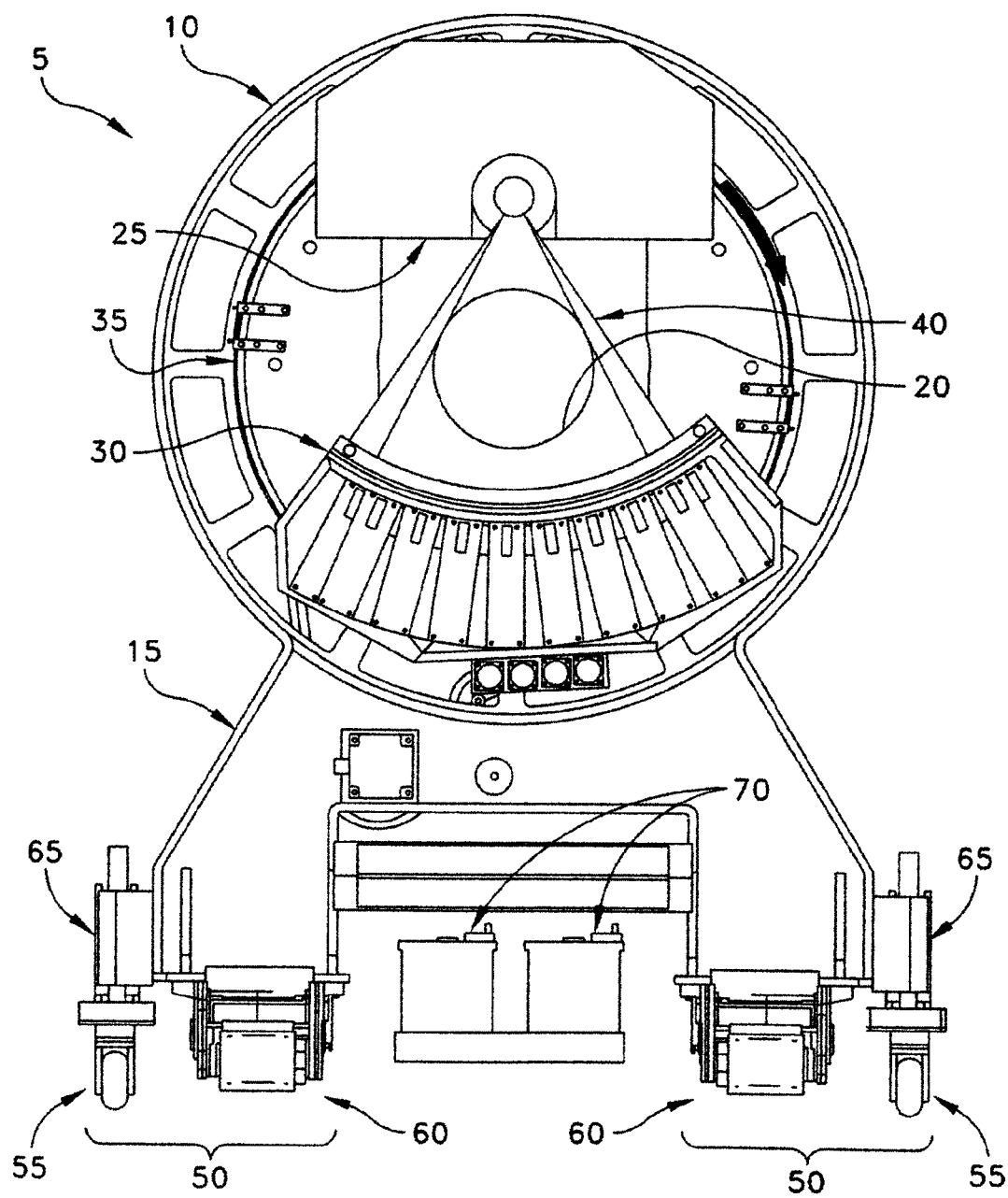
FIG. 3 is a schematic internal view of the CereTom™ CT machine shown in FIGS. 1 and 2.

Looking next at FIG. 3, torus 10 generally comprises an X-ray tube assembly 25, an X-ray detector assembly 30, and a rotating drum assembly 35. X-ray tube assembly 25 and X-ray detector assembly 30 are mounted to the rotating drum assembly 35 in diametrically-opposing relation, such that the X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on the rotating drum assembly 35 so that they are rotated concentrically about center opening 20, the X-ray beam 40 will be passed through the patient's anatomy along a full range of radial positions, so as to enable the CereTom™ CT machine to create the desired computer model of the scanned anatomy.

The various electronic hardware and software for controlling the operation of X-ray tube assembly 25, X-ray detector assembly 30, and rotating drum assembly 35, as well as for processing the acquired scan data so as to generate the desired computer model, are located in torus 10 and/or base 15.

Still looking now at FIG. 3, base 15 comprises a transport assembly 50 for moving CereTom™ CT machine 5 about relative to the patient. More particularly, as disclosed in the aforementioned U.S. patent application Ser. No. 11/706,133, which patent application is hereby incorporated herein by reference, transport assembly 50 comprises a gross movement mechanism 55 for moving CereTom™ CT machine 5 relatively quickly across room distances, and a fine movement mechanism 60 for moving CereTom™ CT machine 5 precisely, relative to the patient, during scanning. As discussed in detail in the aforementioned U.S. patent application Ser. No. 11/706,133, gross movement mechanism 55 preferably comprises a plurality of casters, and fine movement mechanism 60 preferably comprises a plurality of centipede belt drives. Hydraulic apparatus 65 permits either gross movement mechanism 55, or fine movement mechanism 60, to be engaged with the floor, whereby to facilitate appropriate movement of CereTom™ CT machine 5.

Base 15 also includes other system components in addition to those discussed above, e.g., batteries 70 for powering various electrical components of CereTom™ CT machine 5, etc.

As noted above, the various components of CereTom™ CT machine 5 are engineered so as to provide a relatively small, mobile and inexpensive CT machine.

CereTom™ CT machine 5 is particularly well suited for use in stroke applications. More particularly, CereTom™ CT machine 5 is a small, mobile unit which can be pre-positioned in the emergency room and moved to the patient so that the patient can be scanned at their current location, thus eliminating delays due to patient transport and thereby dramatically reducing the time needed to properly diagnose the patient.

More particularly, the mobile CereTom™ CT machine 5 can be located in the emergency room of a hospital and, when a patient presents stroke symptoms, the patient can be immediately scanned in the emergency room so as to determine if the patient is experiencing a stroke and, if so, to determine the nature of the stroke (i.e., hemorrhagic or ischemic). This may be done quickly and easily by moving CereTom™ CT machine 5 across the emergency room to the patient's bed or gurney using the casters of gross movement mechanism 55 and then, while the patient remains on their bed or gurney, scanning the patient by precision-advancing CereTom™ CT machine 5 relative to the patient using the centipede belt drives of fine movement mechanism 60, so that the scanning zone of CereTom™ CT machine 5 is moved relative to the patient. Thus, with CereTom™ CT machine 5, the patient can be scanned in the emergency room while remaining on their bed or gurney, without ever having to be moved from the emergency room to the radiology department and then back again, thereby eliminating the traditional scanning delays associated with conventional CT scanners and thus facilitating proper stroke treatment.

As noted above, the CereTom™ CT machine 5 also has application in numerous other situations where the patient is located remote from the CT machine, e.g., other hospital departments such as Intensive Care Units (ICUs), nursing homes, rehabilitation centers, etc.

X-Ray Transparent Bed and Gurney Extender

As noted above, CereTom™ CT machine 5 is designed to be as small and mobile as possible, and need only scan the head of the patient. As a result, CereTom™ CT machine 5 is configured so as to have a relatively small-diameter center scan opening 20 to receive the head of the patient. Since the hospital beds and gurneys typically found in emergency rooms are too large to fit within the scanning area of CereTom™ CT machine 5, the present invention provides a narrow, X-ray transparent extender for selective attachment to the bed or gurney so as to support the patient's head during scanning, whereby the patient can be quickly and easily scanned while remaining on their bed or gurney.

Figure 4:
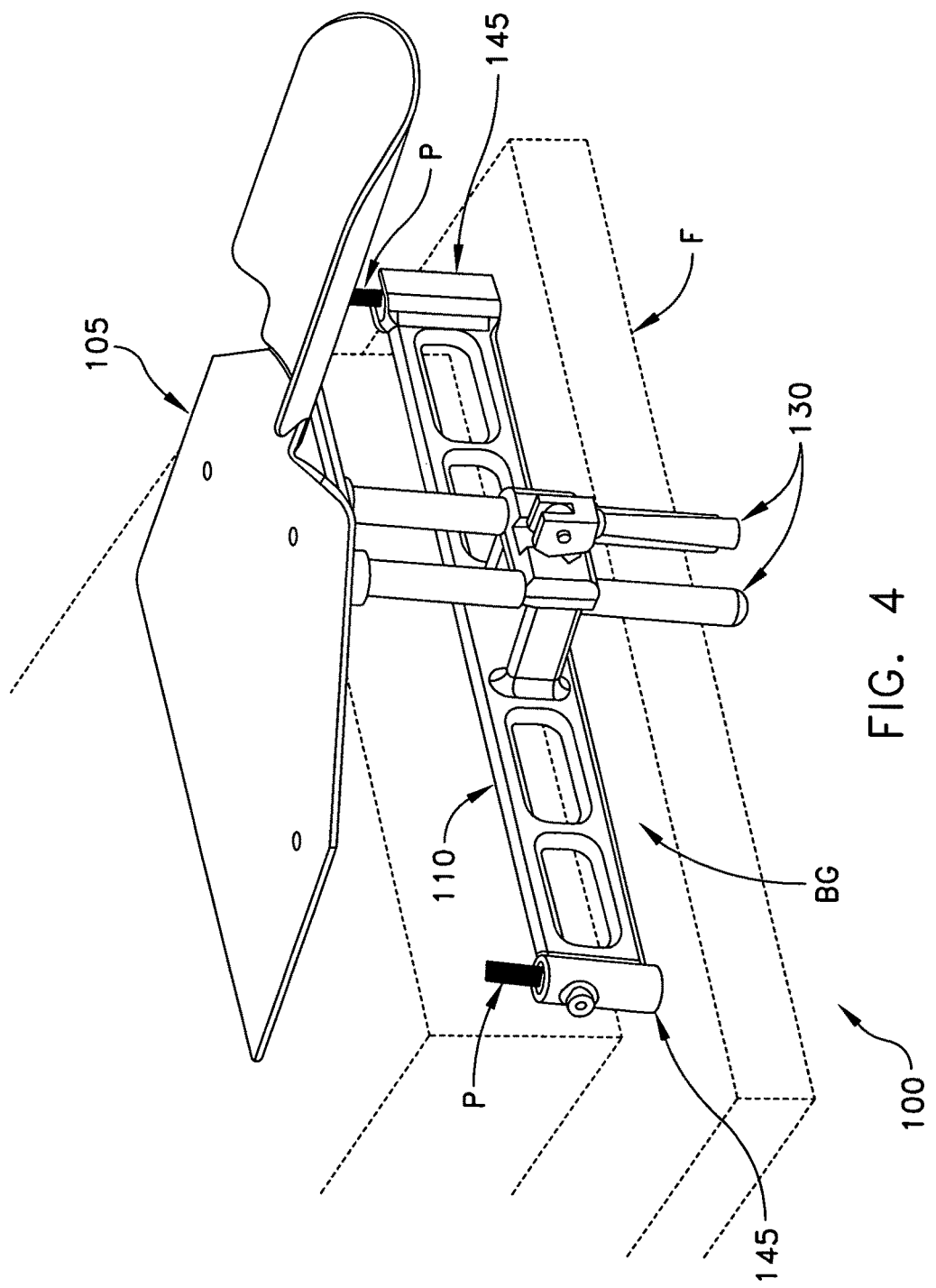
FIG. 4 is a schematic view showing a bed and gurney extender formed in accordance with the present invention.

More particularly, and looking now at FIG. 4, there is shown a bed and gurney extender 100 for selective attachment to a bed or gurney BG. For the purposes of the present invention, bed or gurney BG may be a conventional bed or gurney of the type typically found in an emergency room, or it may be any other patient-supporting platform, e.g., an examination table, an operating table, a medical reclining chair, etc.

Extender 100 generally comprises a support 105 for supporting the head of the patient during scanning, and an adapter 110 for selectively attaching support 105 to bed or gurney BG.

Figure 5:
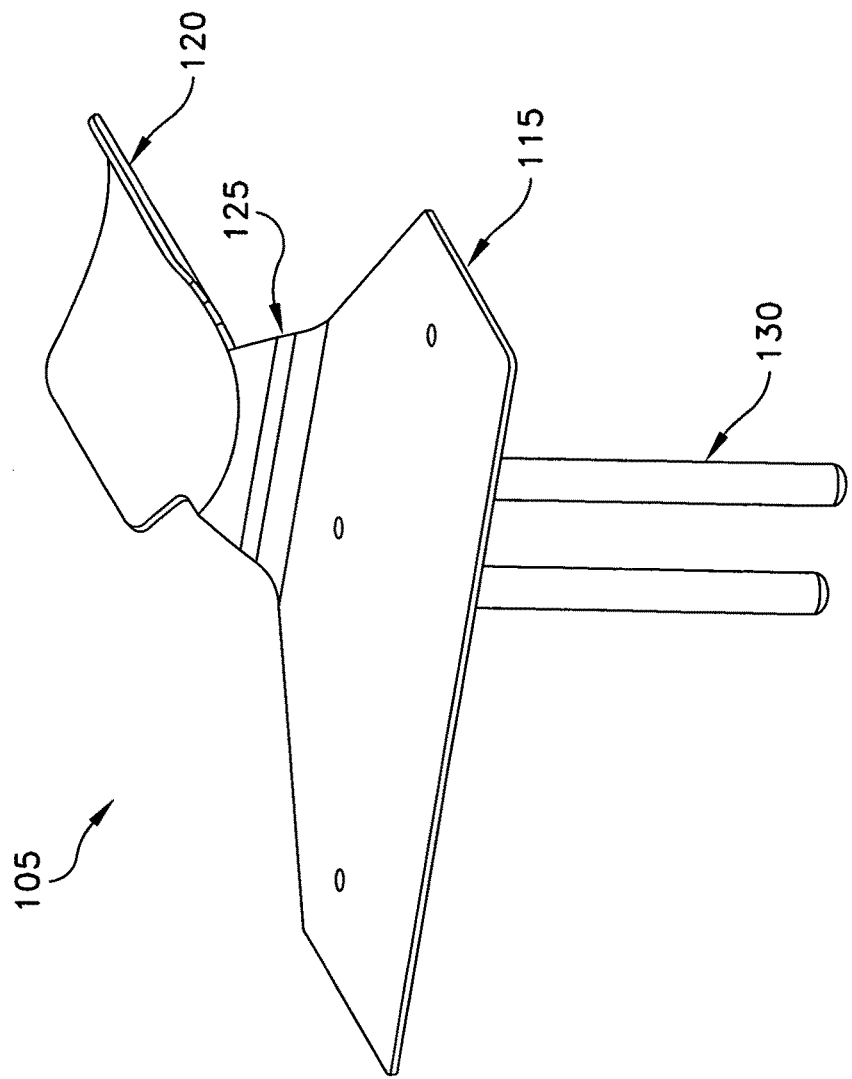
FIGS. 5 and 6 are schematic views showing the support portion of the bed and gurney extender shown in FIG. 4.
Figure 6:
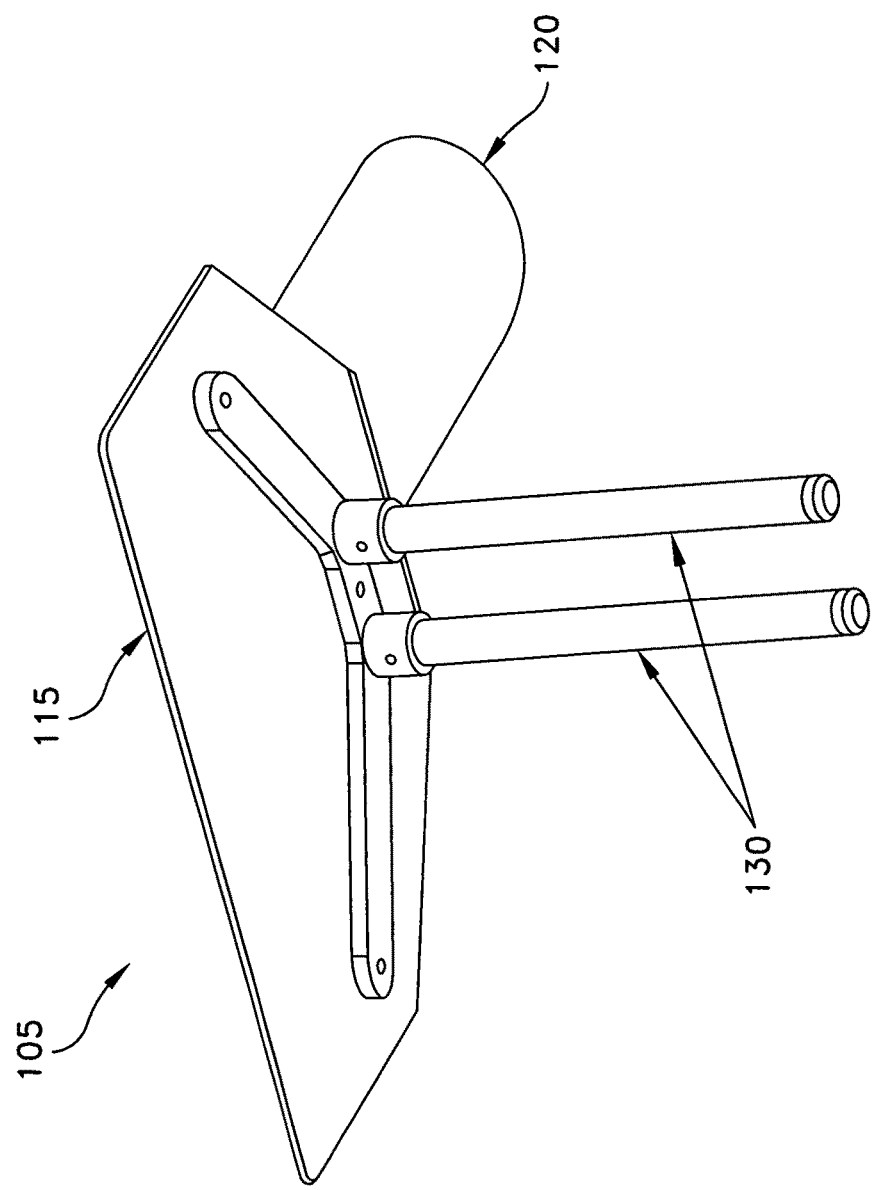
Figure 7:
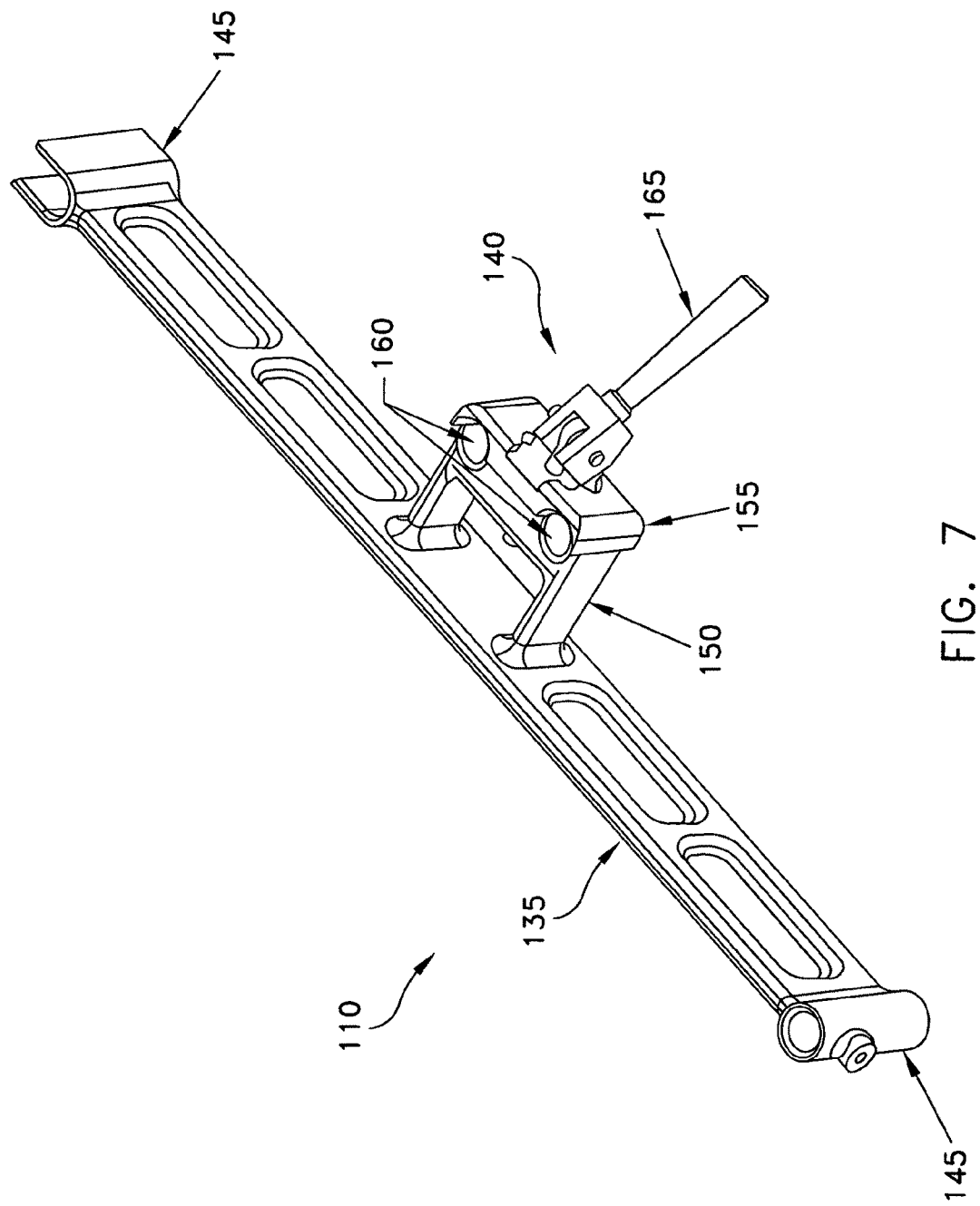
FIGS. 7-10 are schematic views showing the adapter portion of the bed and gurney extender shown in FIG. 4.
Figure 8:
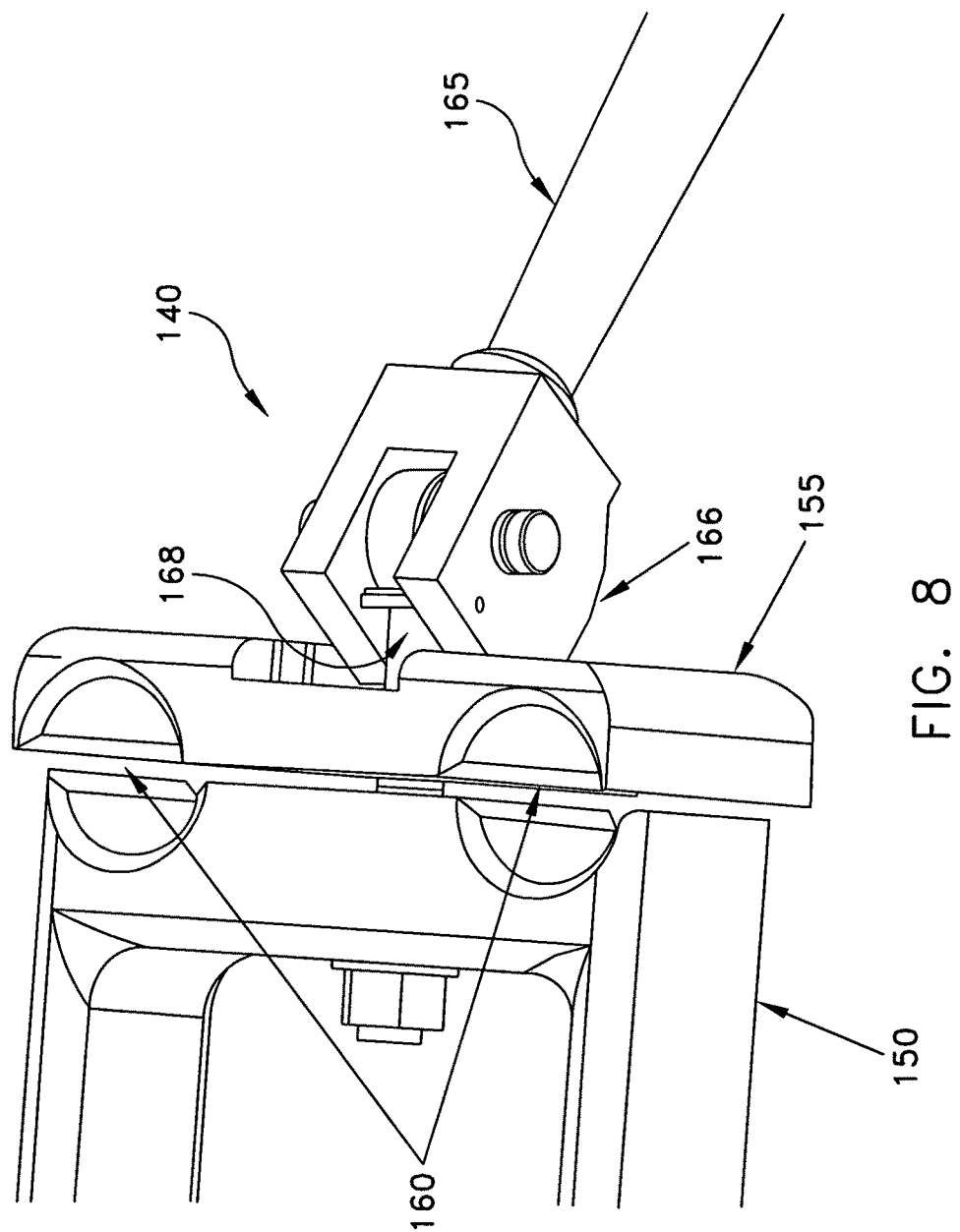
Figure 9:
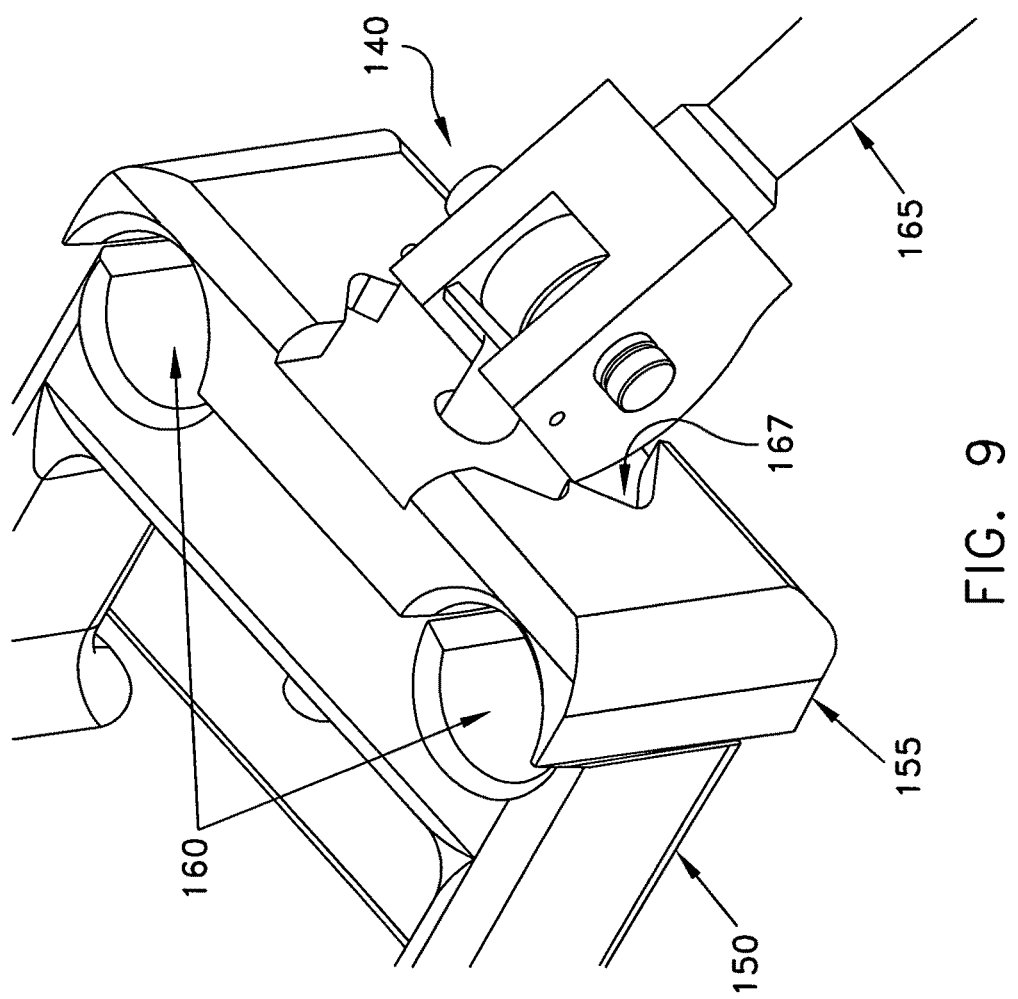
Figure 10:
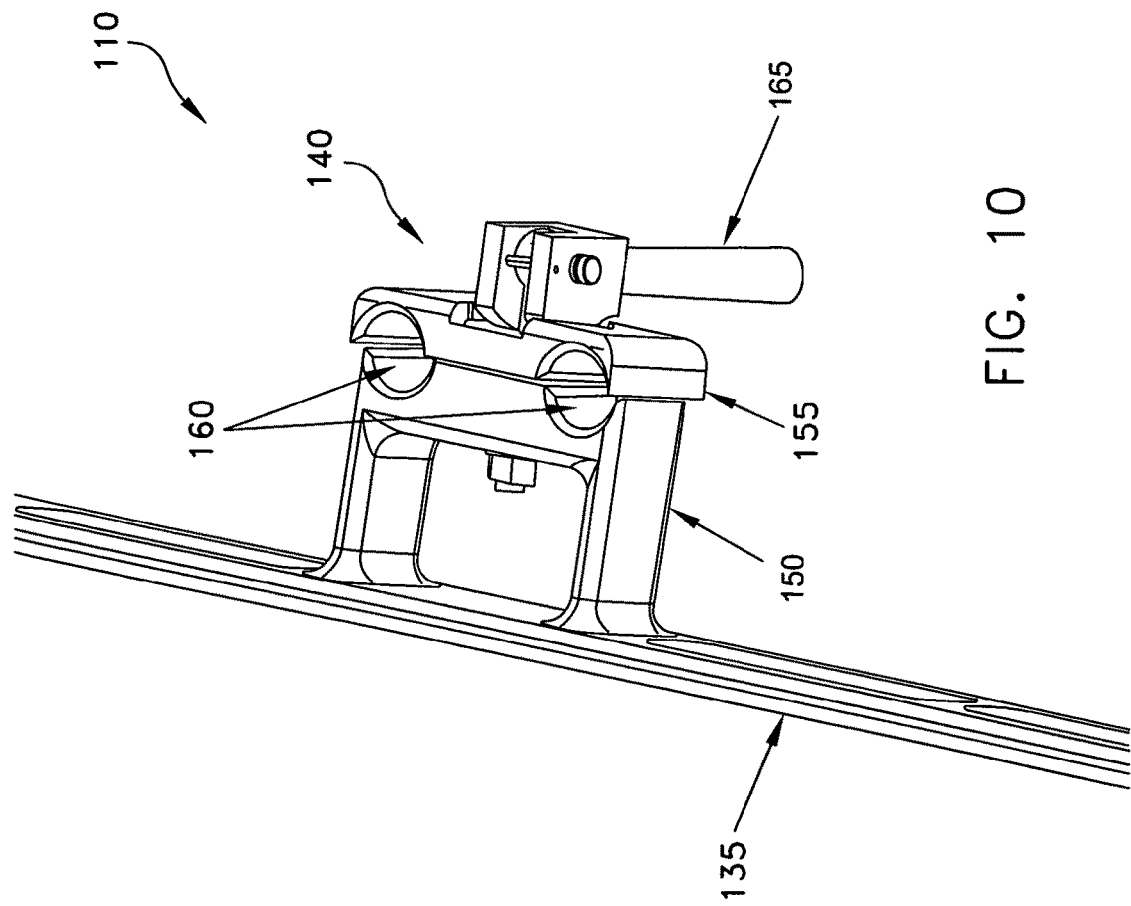

Looking next at FIGS. 5 and 6, support 105 generally comprises a shoulder section 115 for disposition on bed or gurney BG, under the shoulders of the patient, and a head section 120 for supporting the head of the patient. Preferably, head section 120 is connected to shoulder section 115 by a neck section 125.

At least head section 120 is formed out of an X-ray transparent material (e.g., carbon fiber, plastic, etc.), such that head section 120 can be in center opening 20 of CereTom™ CT machine 5 during scanning. If desired, shoulder section 115 and/or neck section 125 can also be formed out of an X-ray transparent material. At least one riser 130 extends out of the underside of shoulder section 115 for selective attachment to adapter 110. In one preferred form of the invention, two risers 130 are provided.

Adapter 110 is shown in FIGS. 4 and 7-10. Adapter 110 generally comprises a bed and gurney mount 135 for selective attachment to the bed or gurney BG, and a riser clamp 140 for selectively securing the at least one riser 130 of support 105 to adapter 110.

The specific configuration of bed and gurney mount 135 is chosen according to the specific configuration of bed or gurney BG. Thus, for example, as seen in FIG. 4, where bed or gurney BG comprises a pair of posts P upstanding from the frame F of bed or gurney BG, bed and gurney mount 135 may comprise a pair of receptacles 145 for receiving posts P, whereby to secure bed and gurney mount 135 to the bed or gurney BG.

Of course, other bed and gurney configurations exist in the marketplace, and hence other configurations may be provided for bed and gurney mount 135, with the specific configuration of bed and gurney mount 135 being matched to the particular configuration of the bed or gurney BG with which the extender 100 is to be used.

Riser clamp 140 comprises a fixed plate 150 and a movable plate 155 which together define at least one variably-sized opening 160 for selectively receiving and securing the at least one riser 130 of support 105. In one preferred form of the invention, two variably-sized openings 160 are provided for receiving the two risers 130 of support 105. In the construction shown in FIGS. 7-10, a handle 165 manipulates a cam mechanism for opening and closing riser clamp 140. In one preferred construction (FIGS. 7-10), handle 165 has a cam surface 166 which bears against plate surface 167 so as to selectively position movable plate 155 along shaft 168, whereby to open and close riser clamp 140. Thus it will be seen that when riser clamp 140 is in its open position, risers 130 can be slidably received in openings 160; and when riser clamp 140 is in its closed position, risers 130 are secured to adapter 110, whereby to secure support 105 to bed or gurney BG.

Use

The apparatus may be used as follows.

When a patient arrives at the emergency room presenting stroke-like symptoms, they are quickly scanned in the emergency room, on their bed or gurney, using CereTom™ CT machine 5 (which is pre-positioned in the emergency room) and extender 100. More particularly, CereTom™ CT machine 5 is raised on its gross movement mechanism 55, i.e., by actuating hydraulic actuators 65. CereTom™ CT machine 5 is then moved on its casters to the patient. Extender 100 is secured to the bed or gurney BG by securing adapter 110 to the bed or gurney BG, opening riser clamp 140 if it is not already open, moving risers 130 through openings 160 of riser clamp 140 until the extender's shoulder section 115 lies flat on the top surface of the bed or gurney BG (the patient may be lifted slightly to facilitate this), and then riser clamp 140 is closed, thereby securing support 105 to bed or gurney BG. Then the patient is moved as necessary so that the head of the patient lies on head section 120. Next, CereTom™ CT machine 5 (which is still raised on its casters) is moved relative to the bed or gurney BG so that the center opening 20 of CereTom™ CT machine 5 is aligned with the patient. Thereafter, hydraulic apparatus 65 is activated so that Cere-Tom™ CT machine 5 is supported on its fine movement mechanism 60 (i.e., the centipede belt drives). Scanning is then commenced, with fine movement mechanism 60 precision-advancing (or precision-retracting, or both precision-advancing and precision-retracting) CereTom™ CT machine 5 relative to the patient during scanning, with scanning being achieved while the patient remains on their bed or gurney. As scanning occurs, head section 120 (upon which the patient's head is supported) does not inhibit scanning, inasmuch as head section 120 is formed out of an X-ray transparent material.

Storing Bed and Gurney Extender 100

Figure 11:
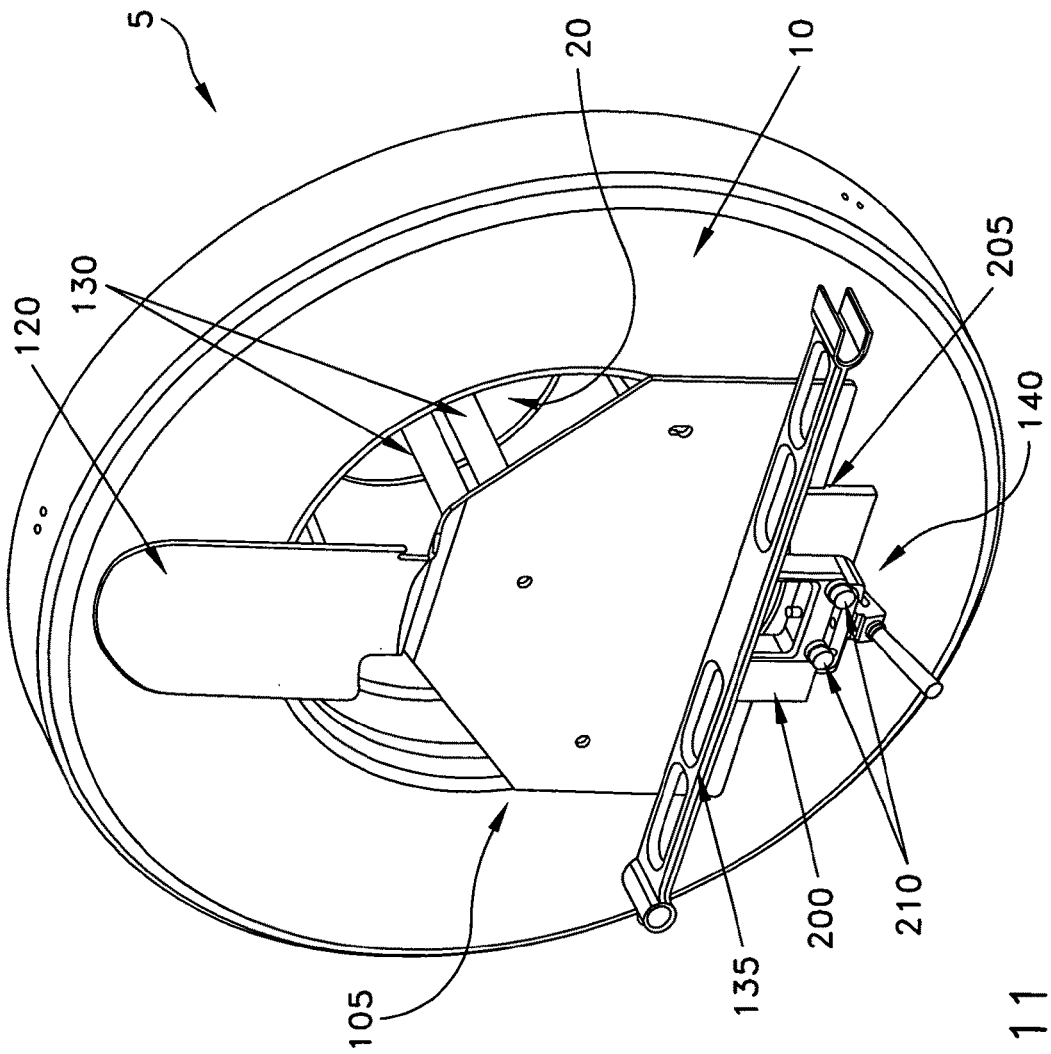
FIGS. 11-14 are schematic views showing how the bed and gurney extender may be stored on a CereTom™ CT machine.
Figure 12:
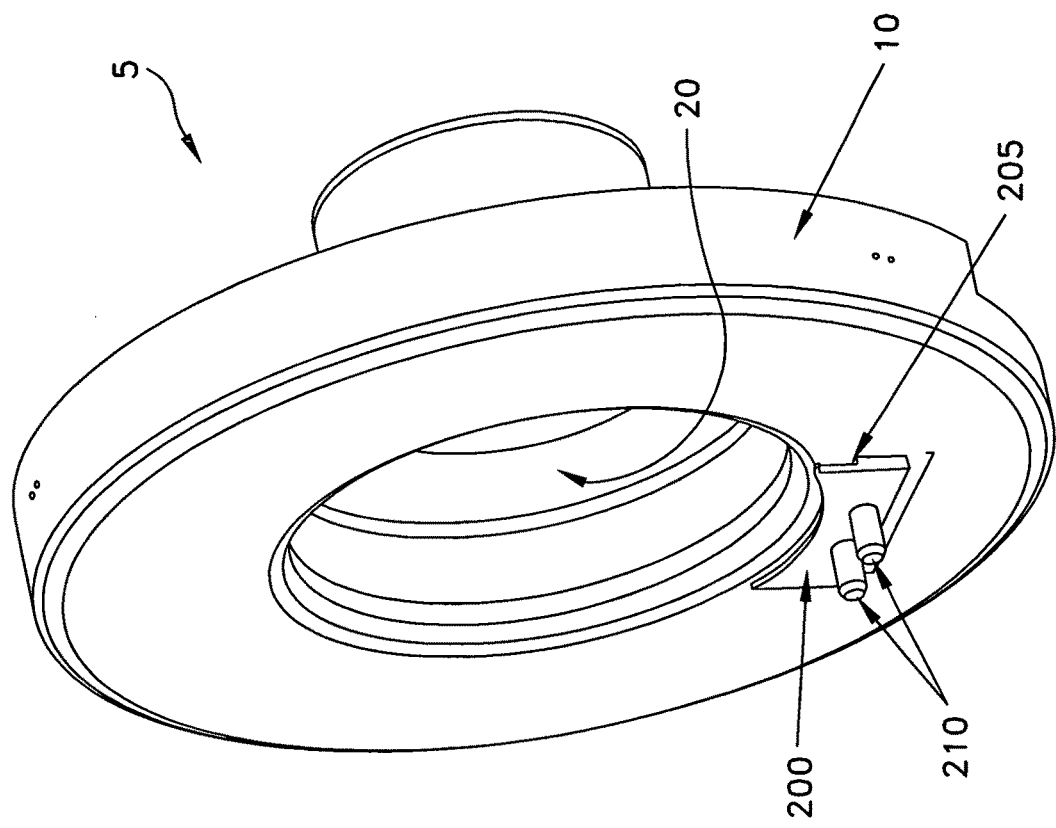
Figure 13:
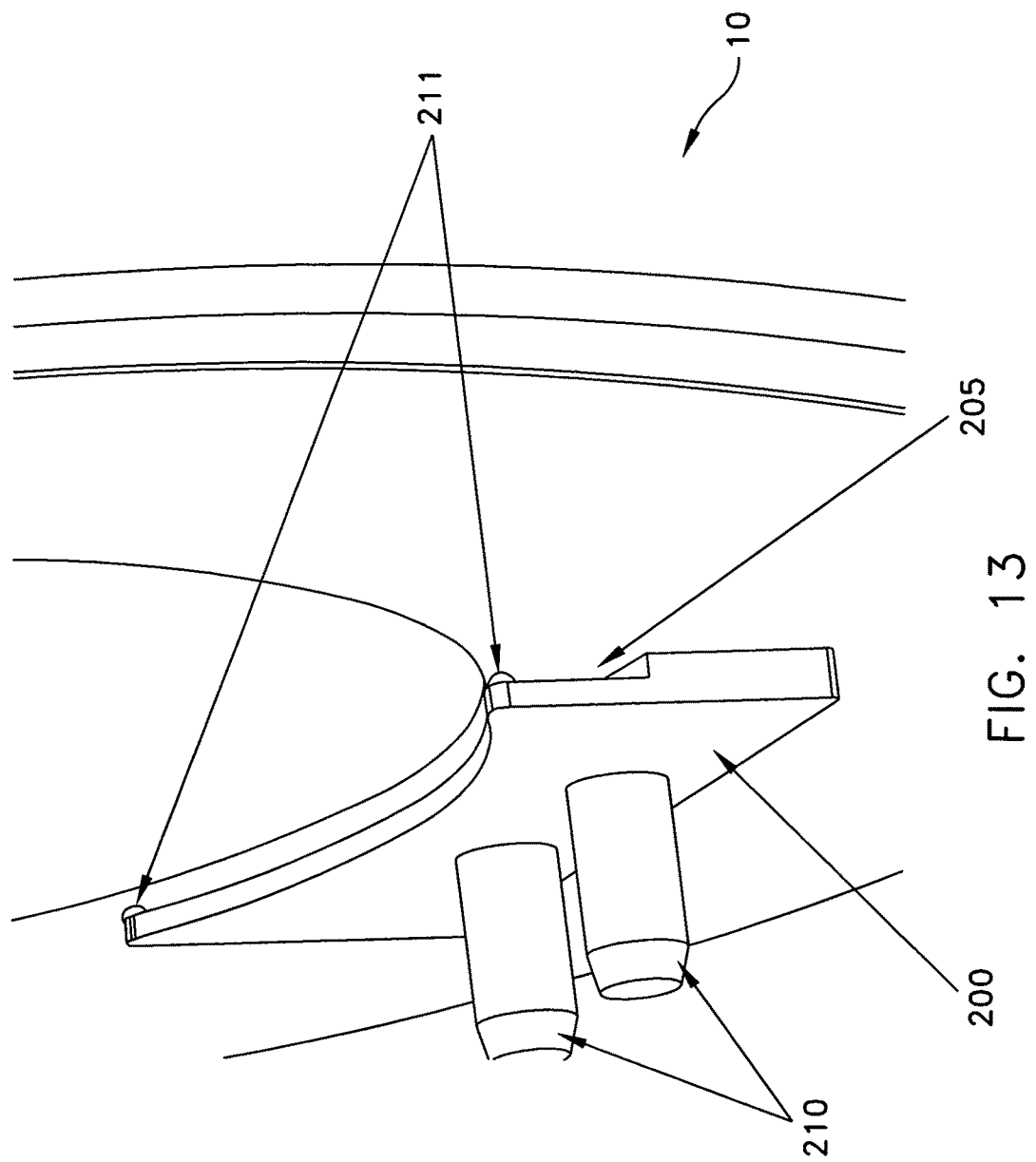
Figure 14:
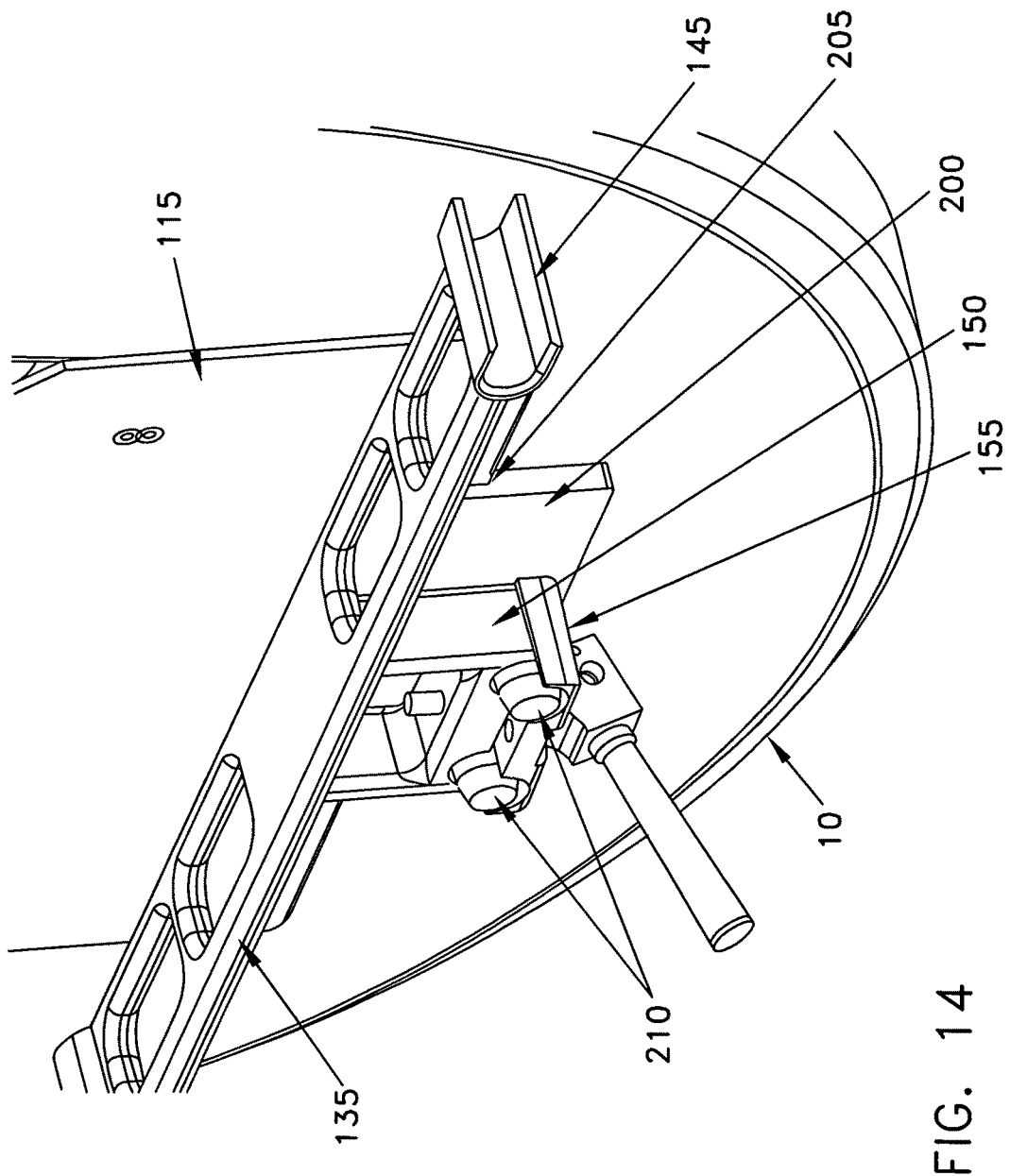
Figure 15:
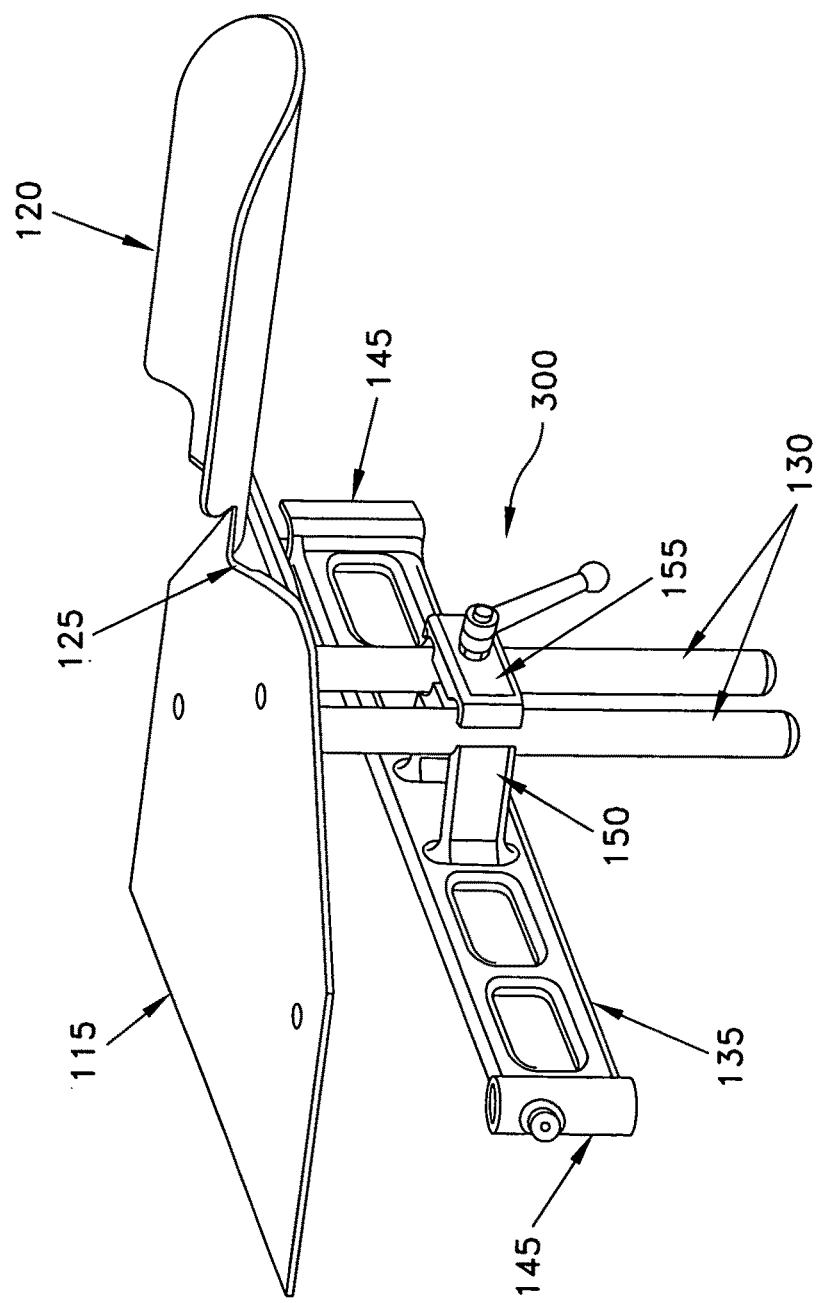
FIGS. 15-18 are schematic views showing an alternative form of riser clamp which may be used in connection with the present invention.
Figure 16:
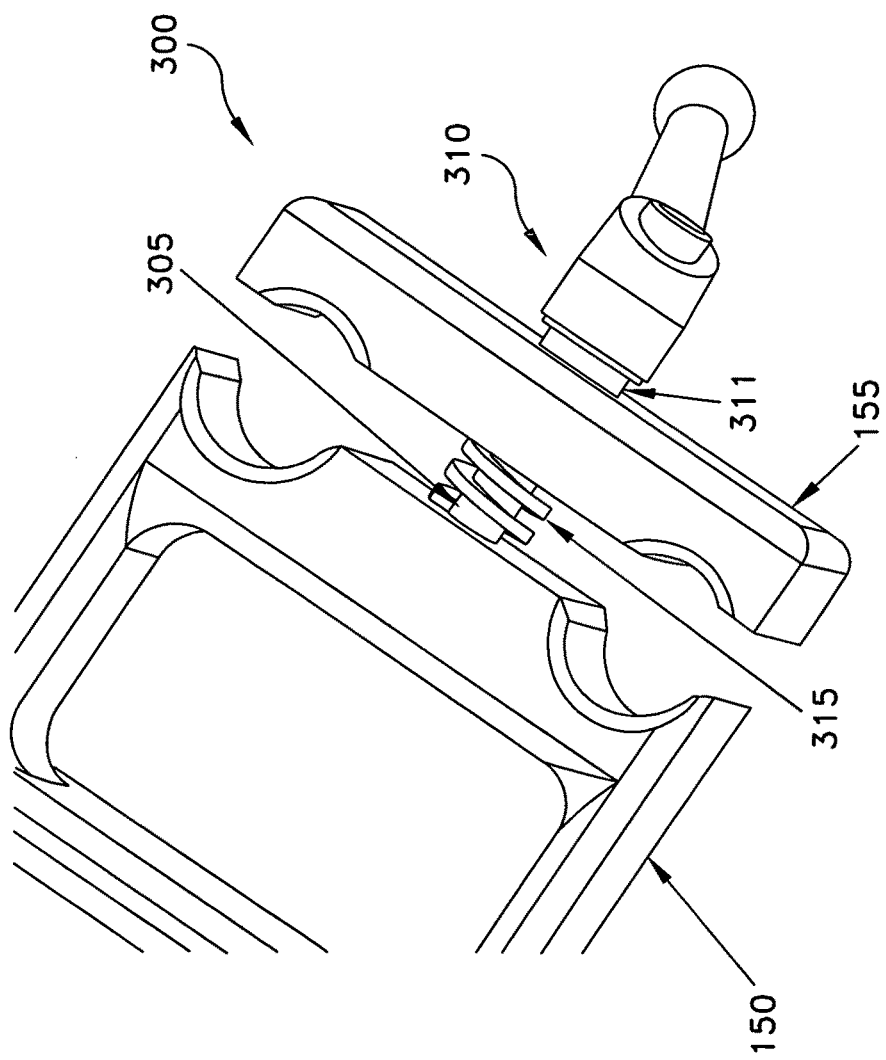
Figure 17:
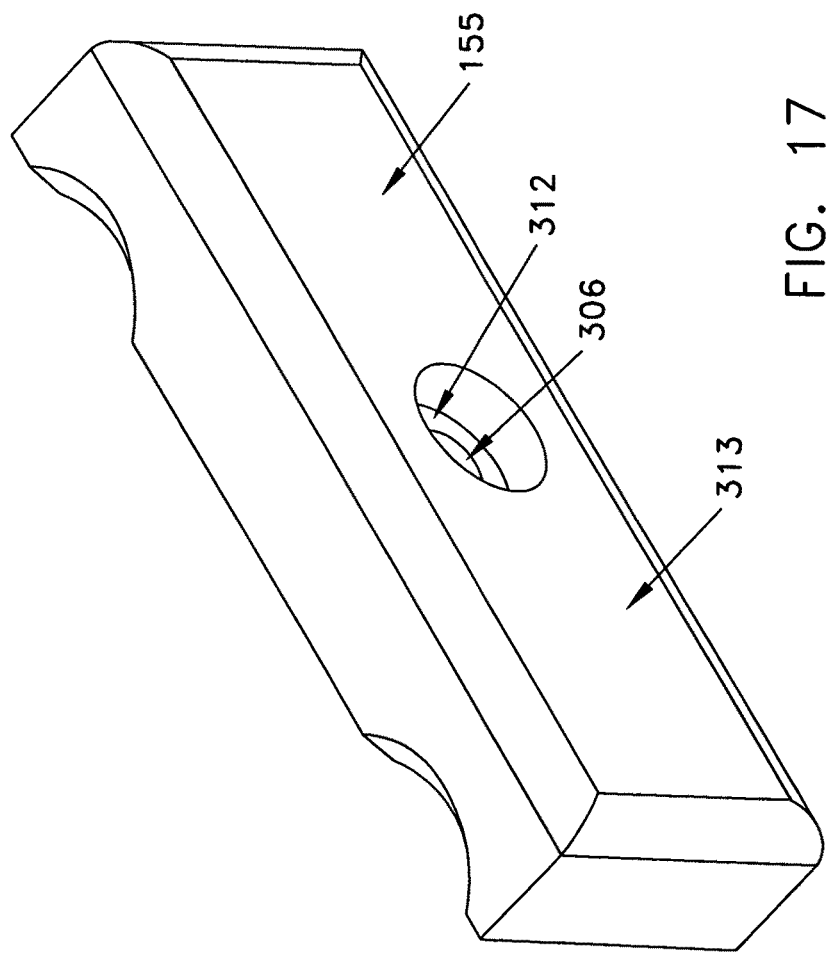
Figure 18:
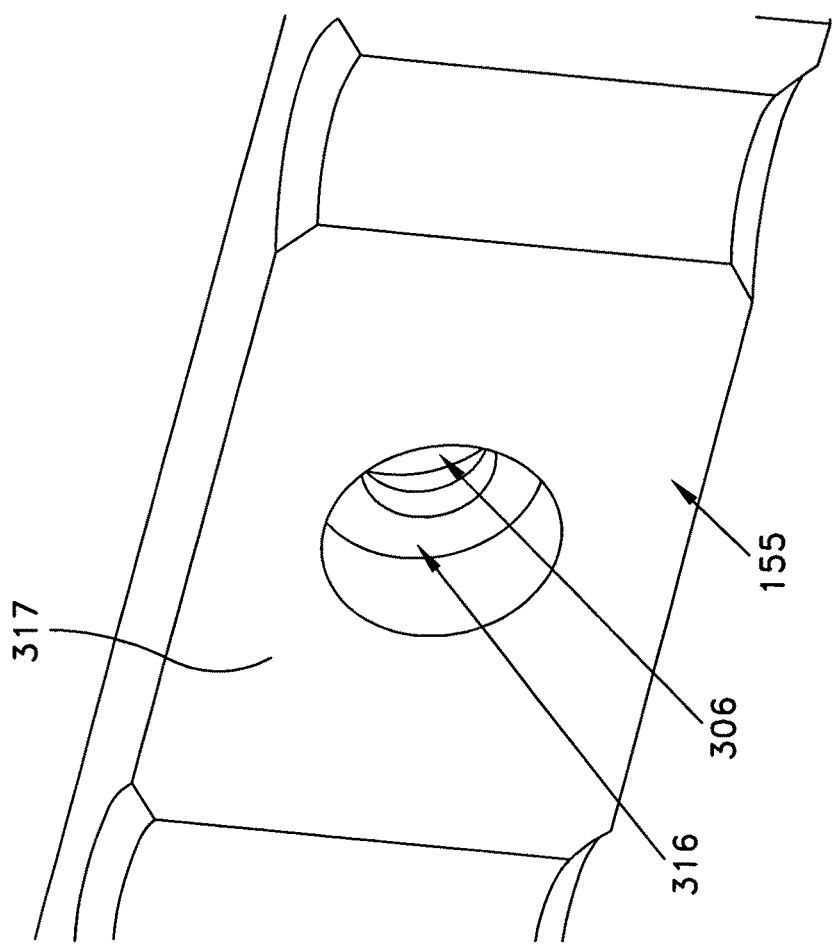

Looking next at FIGS. 11-14, CereTom™ CT machine can be configured to facilitate storing extender 100 on torus 10 of CereTom™ CT machine 5. More particularly, a plate 200, including an undercut 205 and at least one post 210, is attached to the surface of torus 10. Preferably undercut 205 includes two or more beads 211 (FIG. 13) which extend from plate 200 toward CereTom™ CT machine 5. Beads 211 may be made of an elastomer, or a plastic, or a metal. When extender 100 is to be stored on CereTom™ CT machine 5, risers 130 of support 105 are positioned in center opening 20 of CereTom™ CT machine 5 (FIG. 11), and then shoulder section 115 is placed between undercut 205 and torus 10 (FIG. 14), with beads 211 helping to hold shoulder section 115 against torus 10. At the same time, the extender's head section 120 bears against the face of torus 10 (FIG. 11). Then adapter 110 is mounted on the at least one post 210 so as to press shoulder section 115 and head section 120 against torus 10 of CereTom™ CT machine 5 (FIGS. 11 and 14). This is done by opening riser clamp 140, mounting riser clamp 140 on the at least one post 210, and then closing riser clamp 140 so as to secure adapter 110 and hence extender 100 to Cere-Tom™ CT machine 5. Thus it will be seen that the at least one post 210 is preferably arranged so as to have the same configuration as that of the at least one riser 130 (i.e., preferably posts 210 and risers 130 are similar in diameter and, where multiple risers 130 are provided, similar in number and spacing).

Alternative Riser Clamp Constructions

It should be appreciated that it is possible to provide a riser clamp having a construction which is different from the cam-operated riser clamp shown in FIGS. 7-10.

Thus, and looking now at FIGS. 15-18, a crank-operated riser clamp 300 is shown. Crank-operated riser clamp 300 generally comprises a screw 305 which has one end mounted in fixed plate 150 and another end passing through a bore 306 formed in movable plate 155. A crank 310 rides on the free end of screw 305. The inner portion 311 of crank 310 bears against an annular shoulder 312 formed in the outside face 313 of movable plate 155. A spring 315 biases movable plate 155 away from fixed plate 150; one end of spring 315 bears against fixed plate 150 and the other end of spring 315 bears against an annular surface 316 formed in the inside face 317 of movable plate 155. As a result of this construction, crank 310 can be used, in conjunction with spring 315, to move movable plate 155 toward and away from fixed plate 150 so as to close and open riser clamp 300.

Alternative Adapter Constructions

As noted above, many different bed and gurney configurations exist in the marketplace, and hence many different configurations may be provided for bed and gurney mount 135, with the specific configuration of bed and gurney mount 135 being matched to the particular configuration of the bed or gurney BG with which the extender 100 is to be used.

Figure 19:
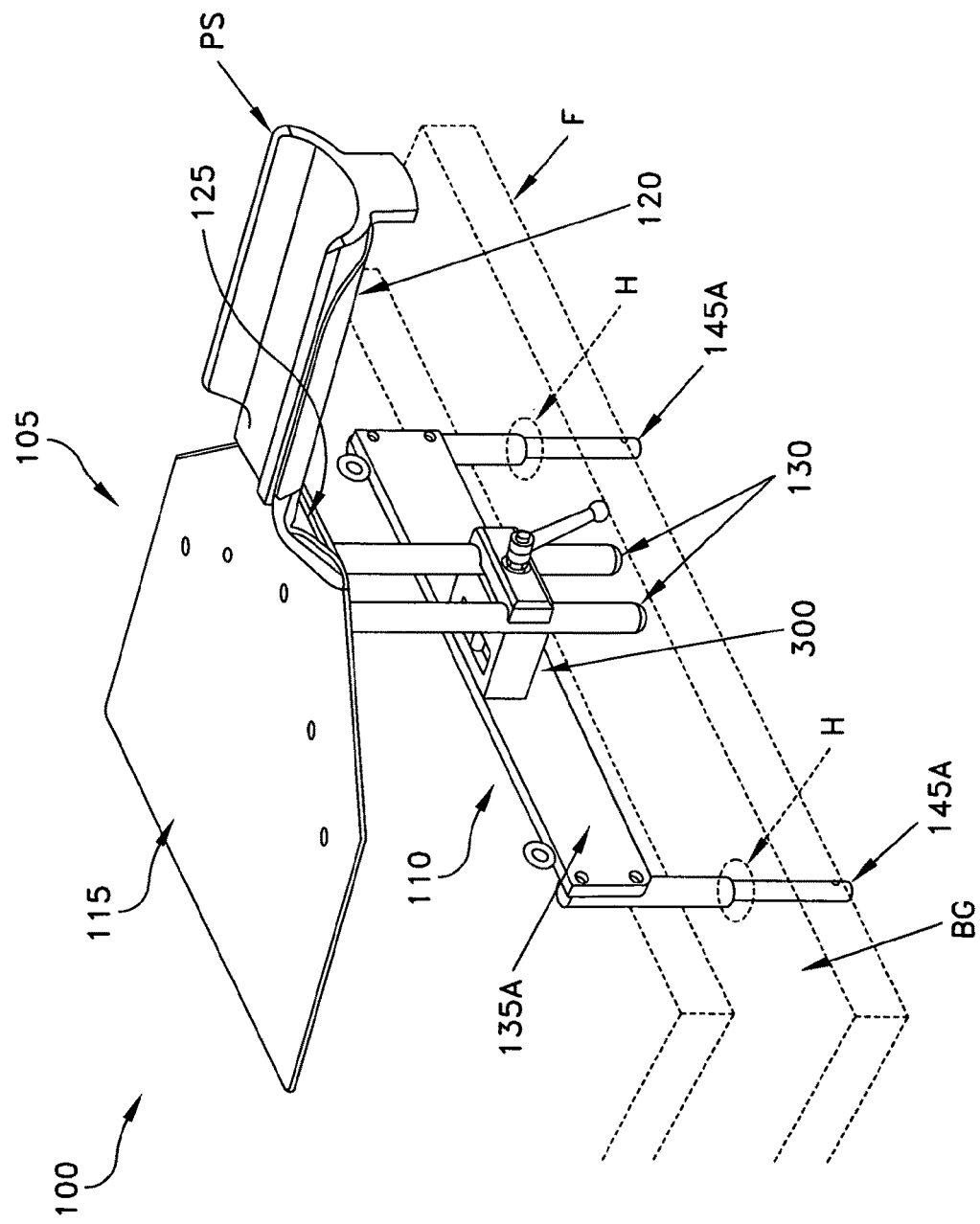
FIG. 19 is a schematic view showing an alternative form of the adapter portion of the bed and gurney extender.

Thus, for example, and looking now at FIG. 19, there is shown an alternative bed and gurney mount 135A. Bed and gurney mount 135A is generally similar to the bed and gurney mount 135 previously discussed, in the sense that the unit mounts to the bed or gurney BG and supports the crank-operated riser clamp 300 (which in turn mounts support 105). However, the alternative bed and gurney mount 135A shown in FIG. 19 is mounted to bed or gurney BG by fitting posts 145A into corresponding holes H formed in the frame F of bed or gurney BG.

If desired, a soft patient support PS may be added to bed and gurney support 105 so as to increase patient comfort. Thus, for example, and looking now at FIG. 19, a patient support PS is shown covering head section 120 and neck section 125. Patient support PS may also cover shoulder section 115 if desired.

Figure 20:
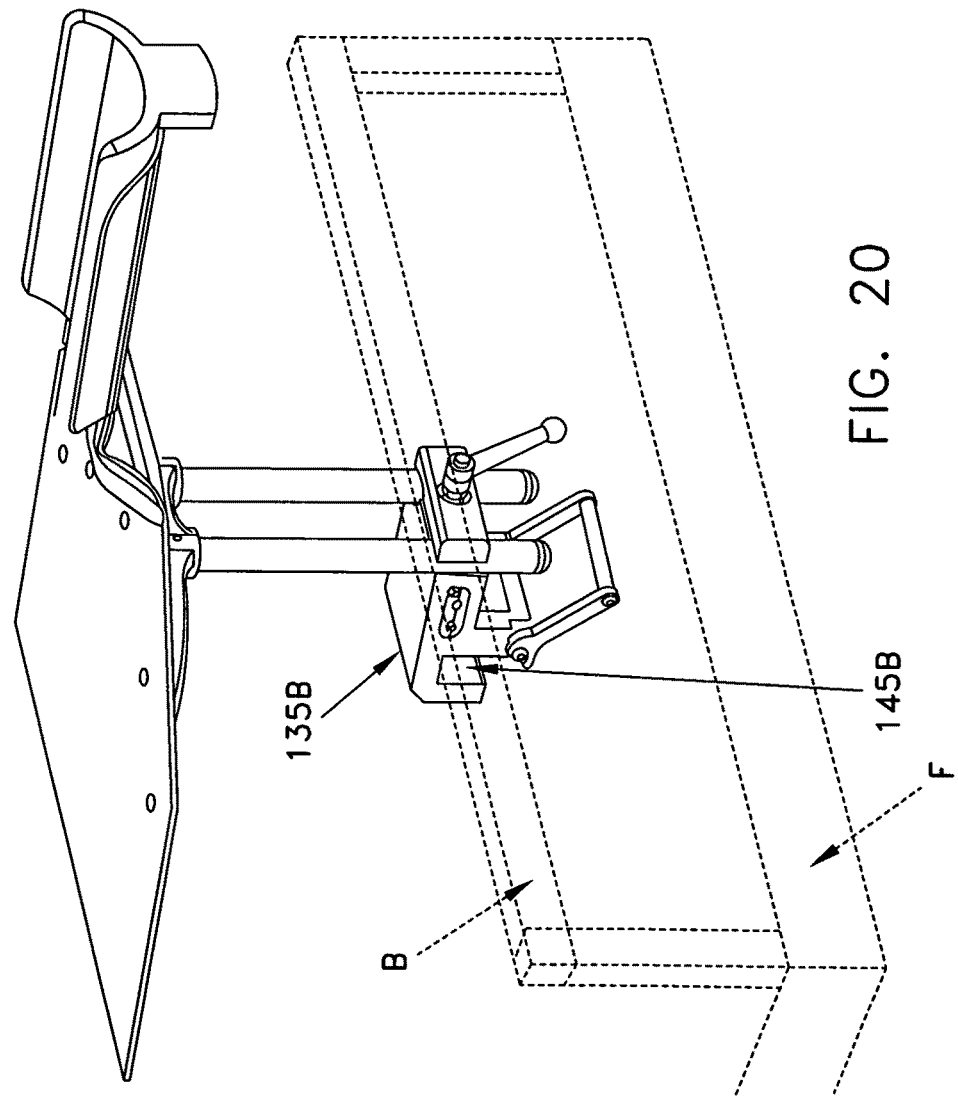
FIGS. 20 and 21 are schematic views showing still another alternative form of the adapter portion of the bed and gurney extender.
Figure 21:
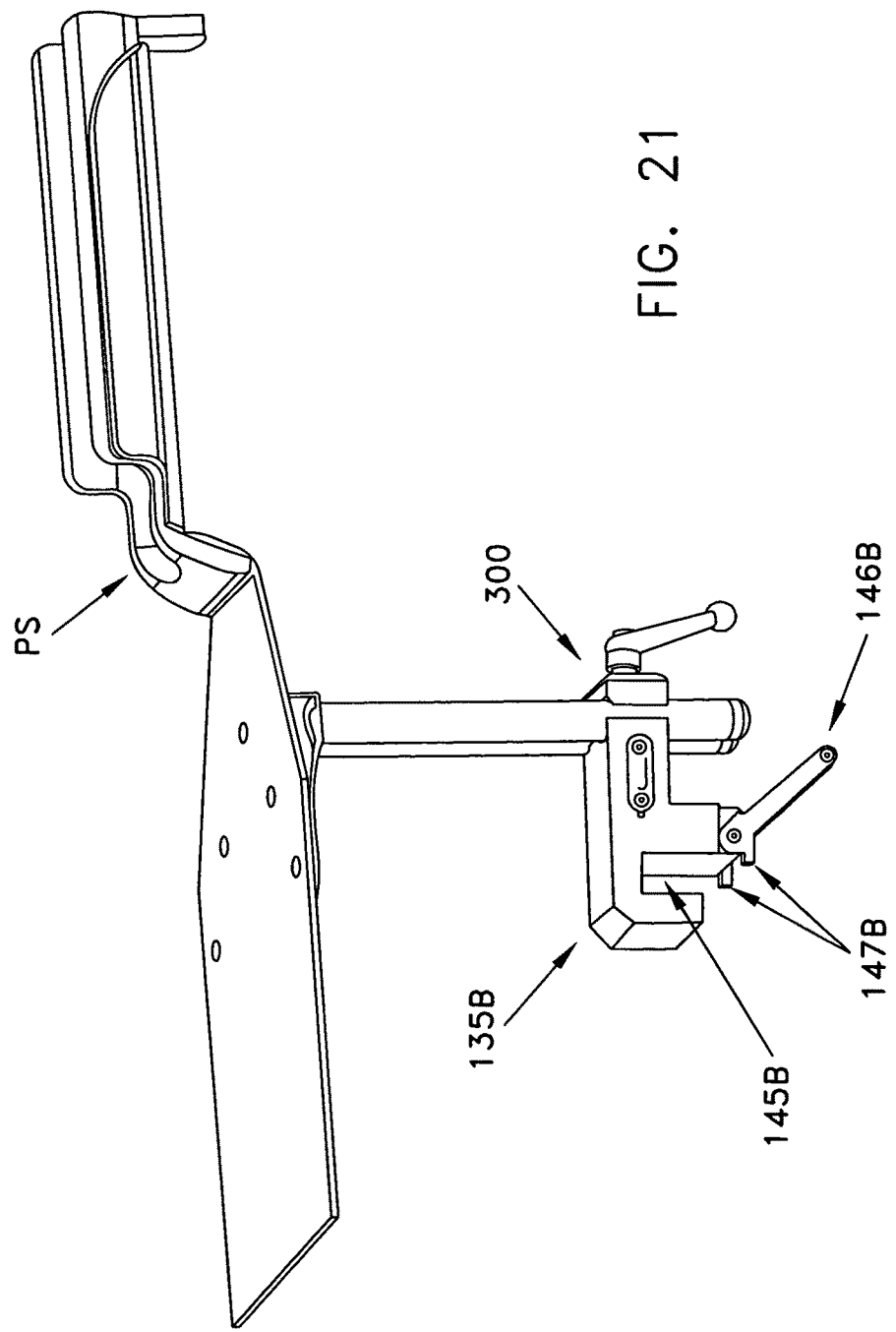

FIGS. 20 and 21 show another alternative bed and gurney mount 135B. Bed and gurney mount 135B generally comprises a rectangular bottom slot 145B which receives a rectangular horizontal bar B of frame F. Due to the rectangular profiles of bottom slot 145B and bar B, bed and gurney mount 145B will be rotationally stable relative to horizontal bar B. A lever latch 146B, including fingers 147B, releasably secures bed and gurney mount 135B to the rectangular horizontal bar B. Riser clamp 300 is formed integral with bed and gurney mount 135B.

Figure 22:
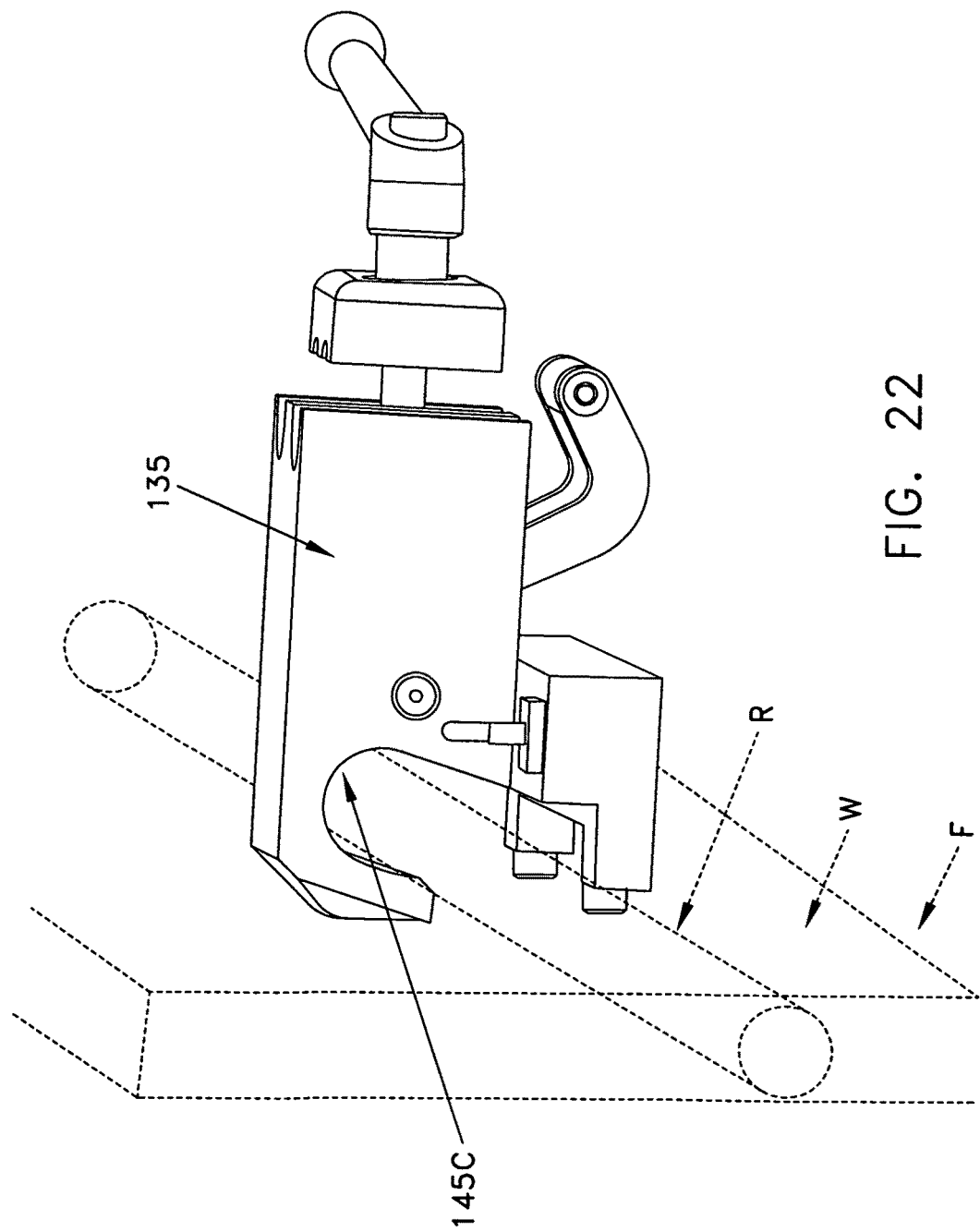
FIGS. 22 and 23 are schematic views showing yet another form of the adapter portion of the bed and gurney extender.
Figure 23:
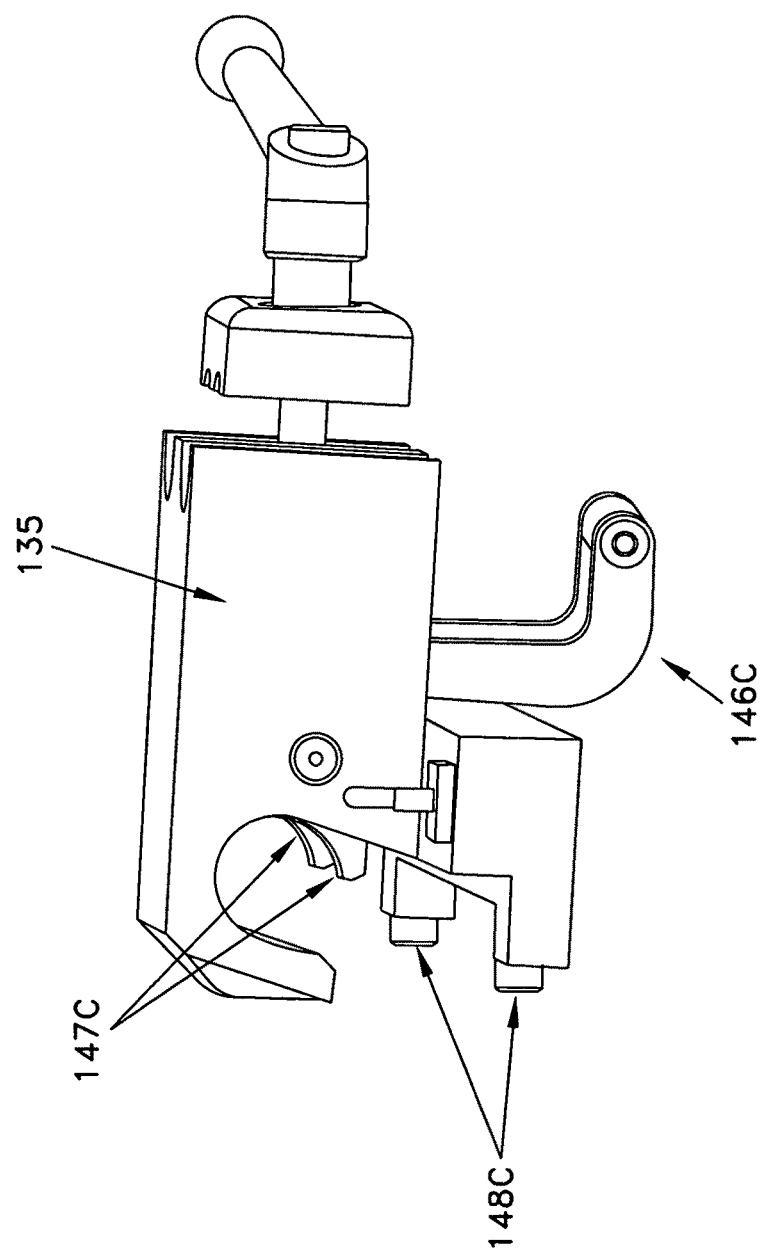

A slightly different arrangement is shown in FIGS. 22 and 23. More particularly, in some circumstances, the bed or gurney BG may comprise a frame F which includes a round rod R disposed adjacent to a vertical wall W. In this circumstance, rotational stability must be provided if riser clamp 300 is mounted to the round rod R. Accordingly, and looking now at FIGS. 22 and 23, there is shown a bed and gurney mount 135C having a slot 145C formed therein. A lever latch 146C, including fingers 147C, releasably secures bed and gurney mount 135C to the round rod R. A pair of feet 148C bear against wall W of frame F so as to prevent clockwise rotation (when seen from the angle of view of FIGS. 22 and 23) of bed and gurney mount 135C relative to round rod R. Riser clamp 300 is formed integral with bed and gurney mount 135C.

It is also possible to form extender 100 without using risers 130. More particularly, and looking now at FIG. 24, there is shown an extender 100D which generally comprises a shoulder section 115D and a head section 120D, joined by a neck section 125D. A horizontal rod 130D is used to connect extender 100 to adapter 110. In this construction, adapter 110 generally comprises a bed and gurney mount 135D for selective attachment to the frame F of the bed or gurney, and a clamp 400 for clamping horizontal rod 130D in position. Clamp 400 generally comprises a fixed jaw 405 and a movable jaw 410. A screw 415 secures movable jaw to 410 fixed jaw 405.

Alternative Bed and Gurney Extender Support

It should be appreciated that it is also possible to provide a bed and gurney support element having a construction which is different from bed and gurney support 105 shown in FIGS. 4-6.

Figure 25:
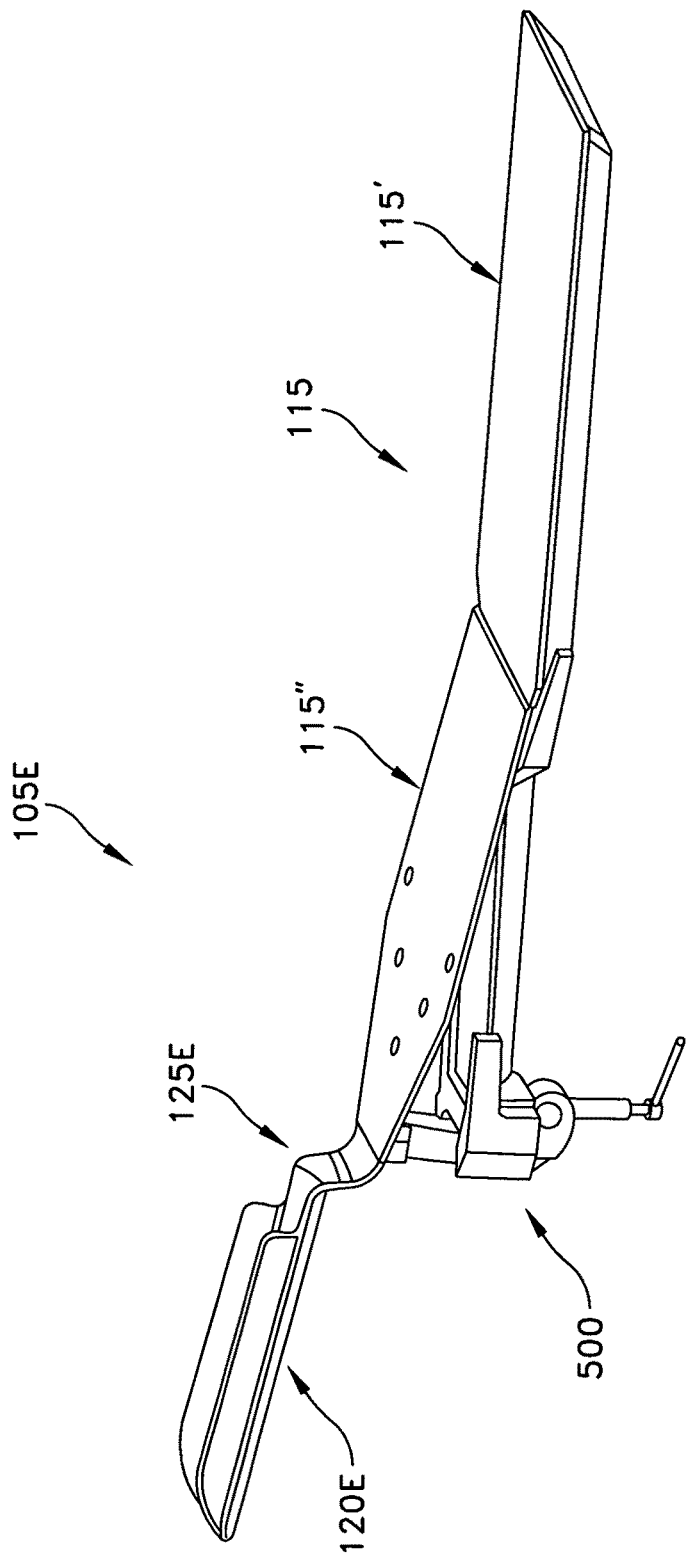
FIG. 25 is a schematic view showing another support formed in accordance with the present invention.

By way of example but not limitation, and looking now at FIG. 25, there is shown a support 105E which permits the patient's head to be aligned with the center opening 20 of CereTom™ CT machine 5. To that end, support 105E comprises a hinged shoulder section 115E for disposition under the shoulders of the patient, a head section 120E for supporting of the head of the patient, and a neck section 125E for connecting head section 120E to hinged shoulder section 115E. Hinged shoulder section 115E in turn is a first shoulder section 115E' and a second shoulder section 115E". An elevator 500 is provided to raise or lower hinged shoulder section 115E" relative to hinged shoulder section 115E', whereby to permit the patient's head to be aligned with the center opening 20 of CereTom™ CT machine 5.

Figure 24:
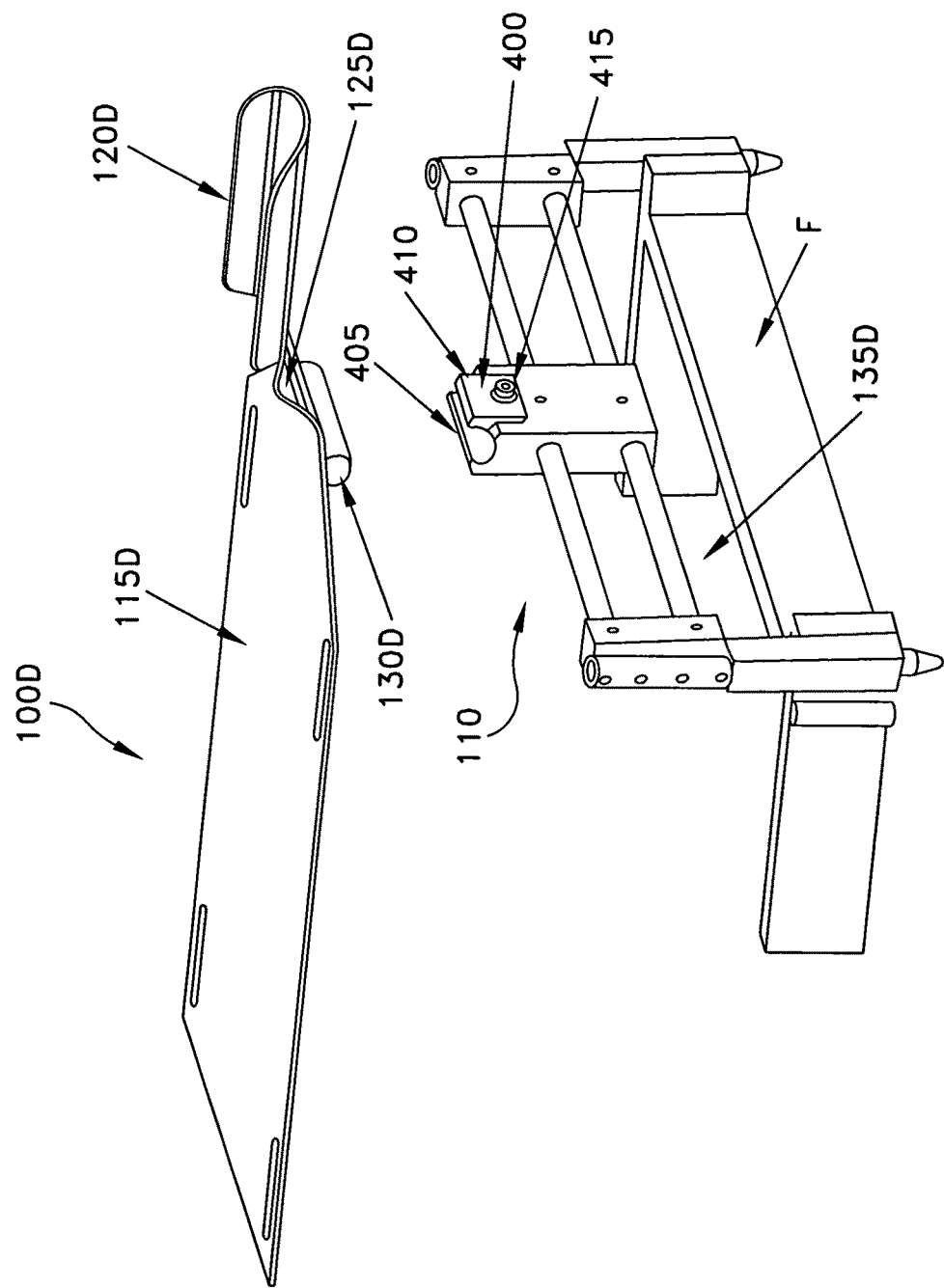
FIG. 24 is a schematic view showing another bed and gurney extender formed in accordance with the present invention.

Support 105E can be particularly useful when using an extender such as the extender 100D shown in FIG. 24, inasmuch as extender 100D does not provide vertical adjustment of extender 100D relative to the bed or gurney BG. Elevator 500 of support 105E can provide this vertical adjustment.

Additional Supports for Supporting

Patient Anatomy During Scanning

The present invention also provides additional supports for supporting patient anatomy during scanning.

1. OR Table Extender.

Figure 26:
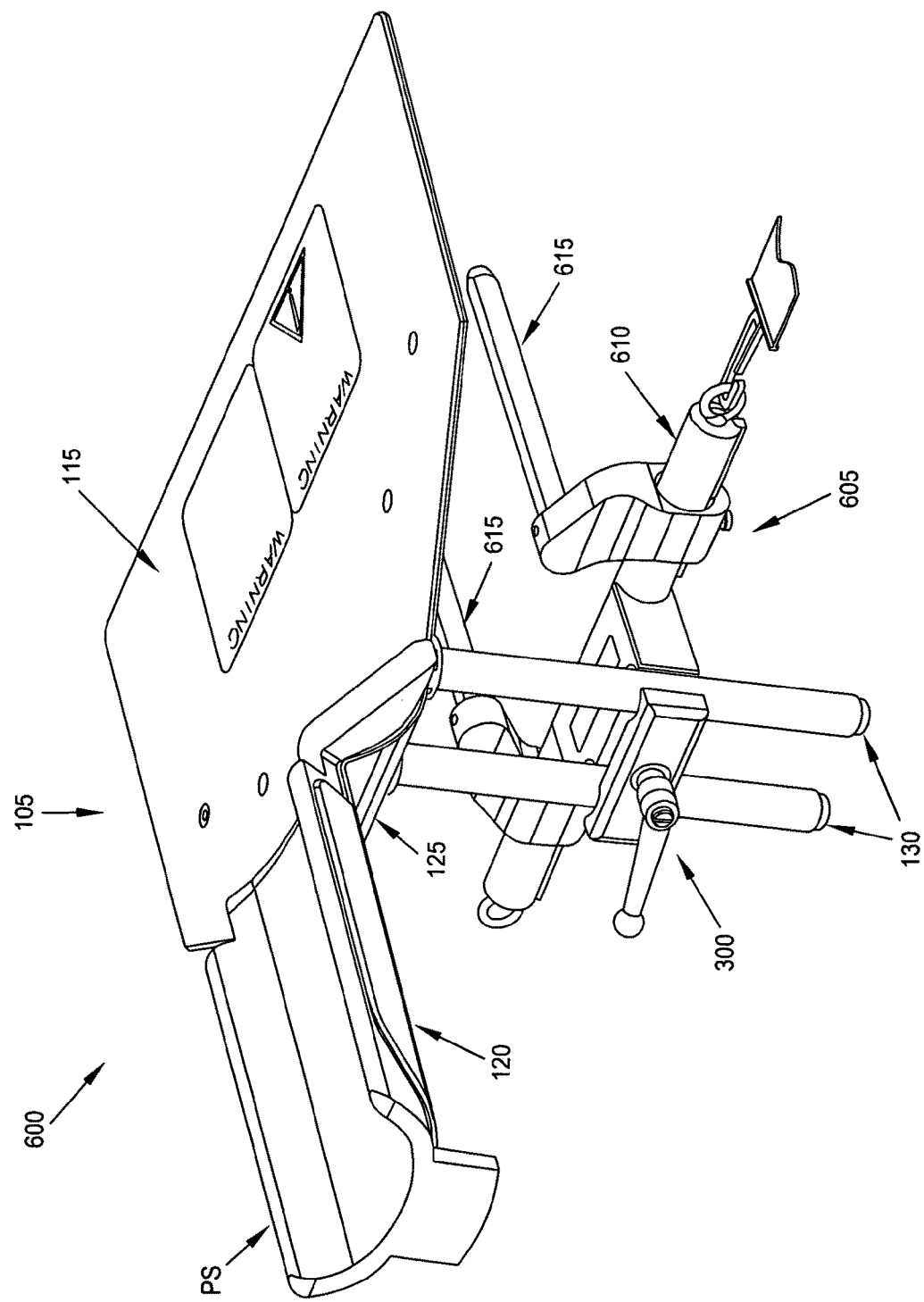
FIGS. 26-28 are schematic views showing an extender for use with an operating table or like patient-supporting platform.
Figure 27:
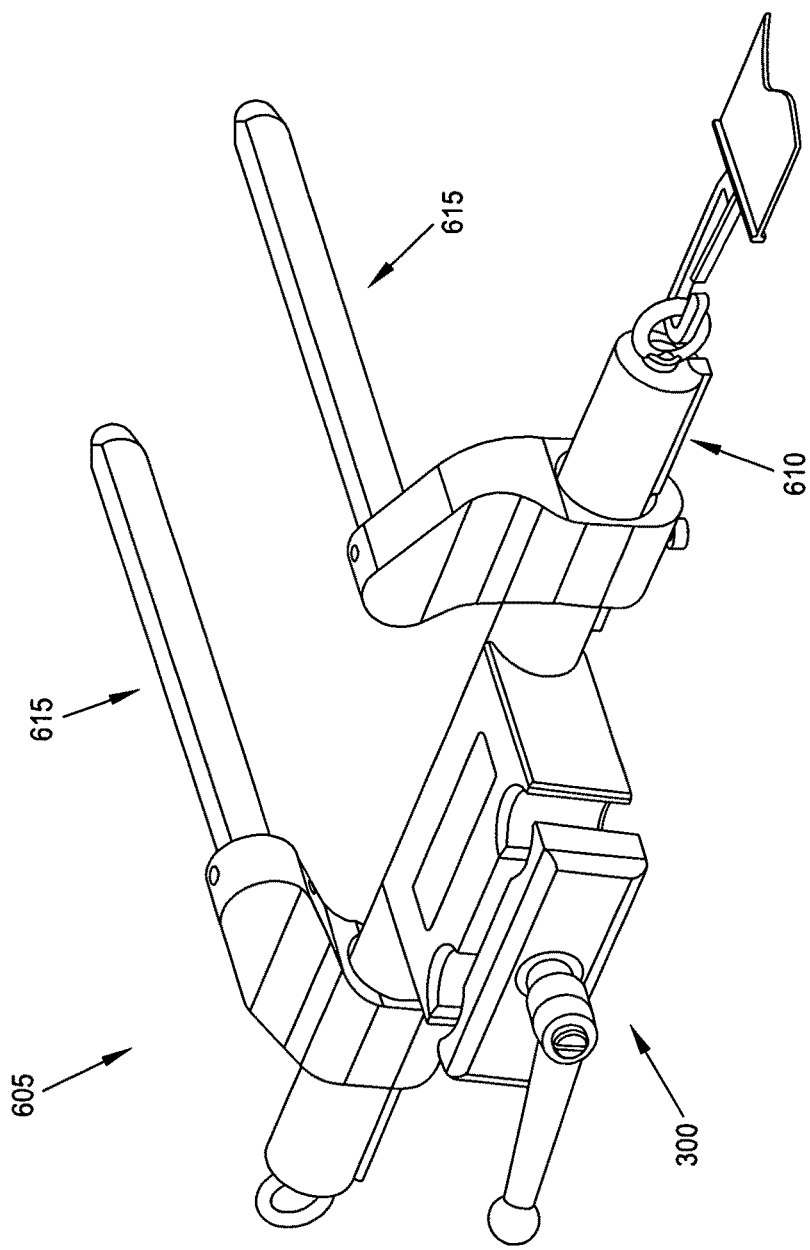
Figure 28:
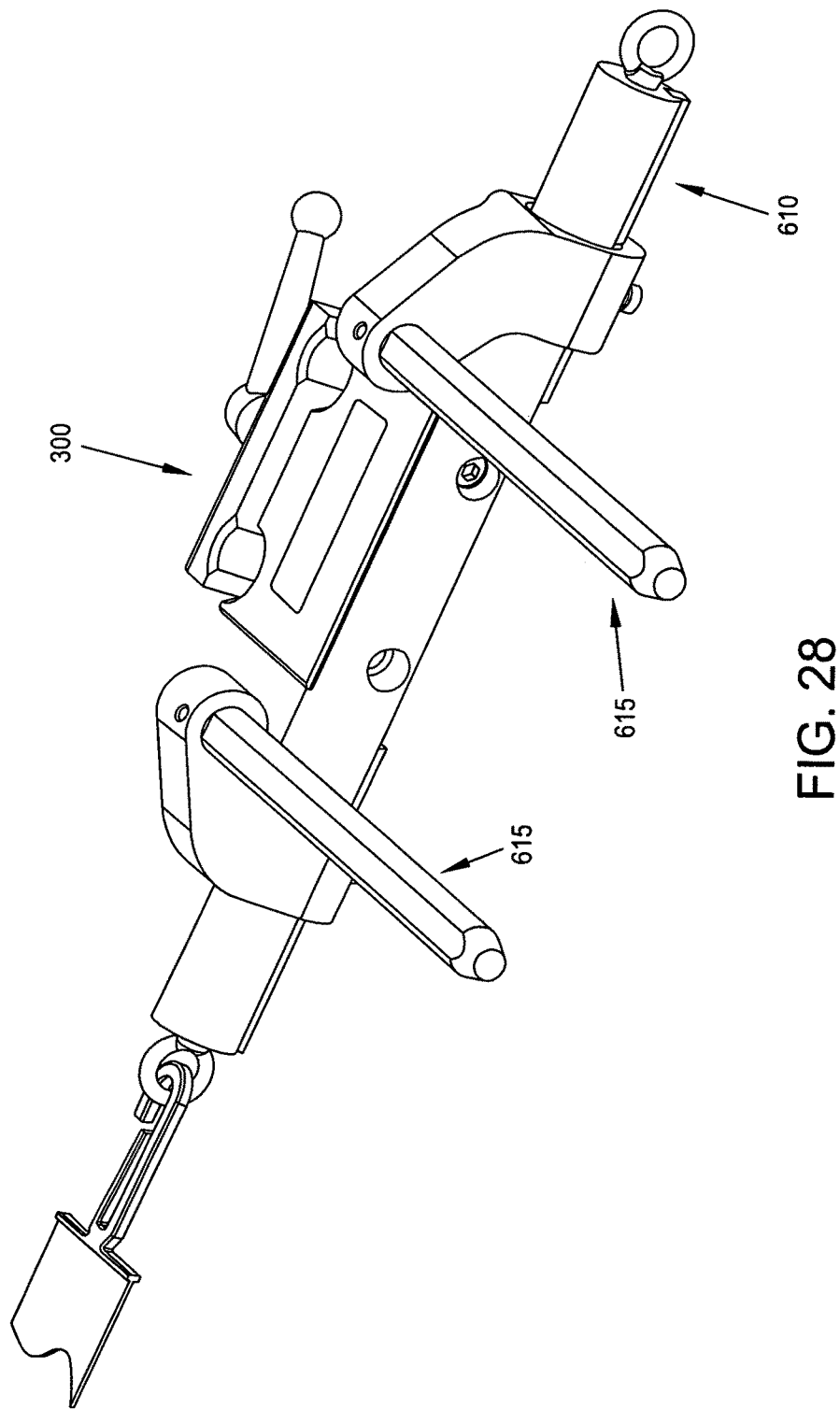

More particularly, and looking now at FIGS. 26-28, there is shown a novel extender 600 for use with an operating table or like patient-supporting platform. Extender 600 generally comprises (i) the support 105 previously discussed, including the shoulder section 115, head section 120, neck section 125, patient support PS and at least one riser 130, and (ii) a novel adapter 605 for selective attachment to an operating table or like patient-supporting platform (not shown). Novel adapter 605 generally comprises a rail 610 which includes a pair of arms 615 for mounting to an operating table or like patient-supporting platform (not shown), e.g., by inserting arms 615 into appropriate recesses or clamping apparatus provided by the operating table or like patient-supporting platform. Novel adapter 605 also comprises the crank-operated riser clamp 300 previously described. On account of this construction, when adapter 605 is properly mounted to an operating table or like patient-supporting platform, crank-operated riser clamp 300 can be used to adjust the position of support 105 as desired, whereby to support patient anatomy (e.g., the head of the patient) during scanning.

It is also possible to provide a free-standing support for supporting the anatomy of a patient during scanning.

2. Infant Support.

Figure 29:
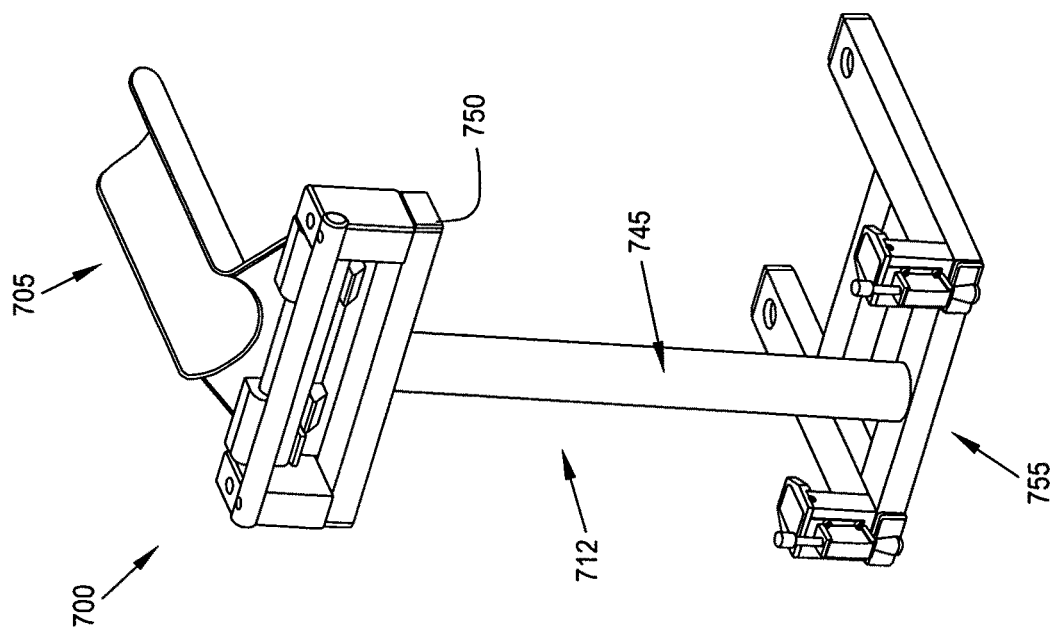
FIGS. 29-57 are schematic views showing a support for supporting anatomy of a patient (e.g., the body of an infant) during scanning.
Figure 30:
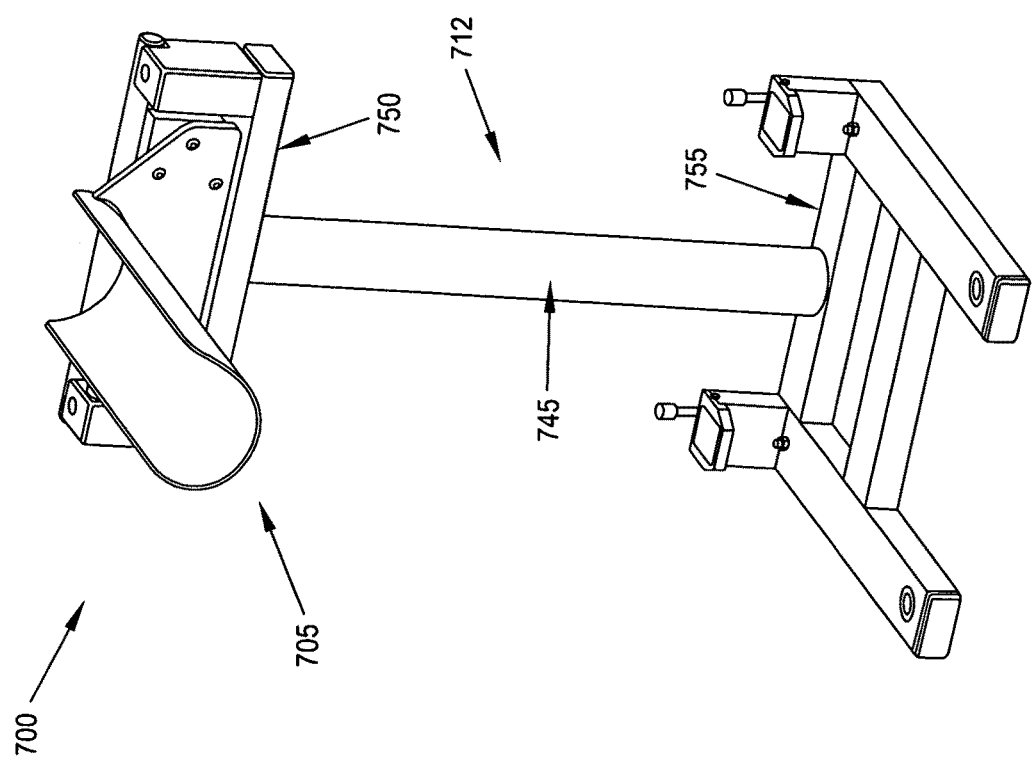
Figure 31:
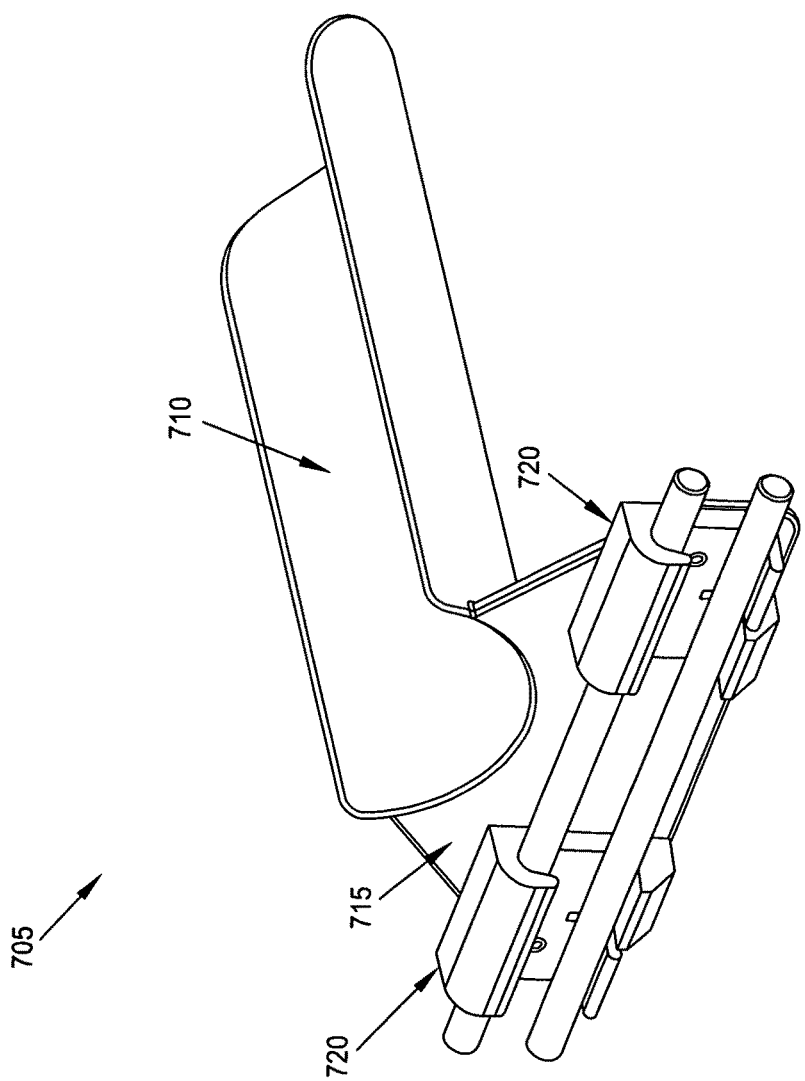
Figure 32:
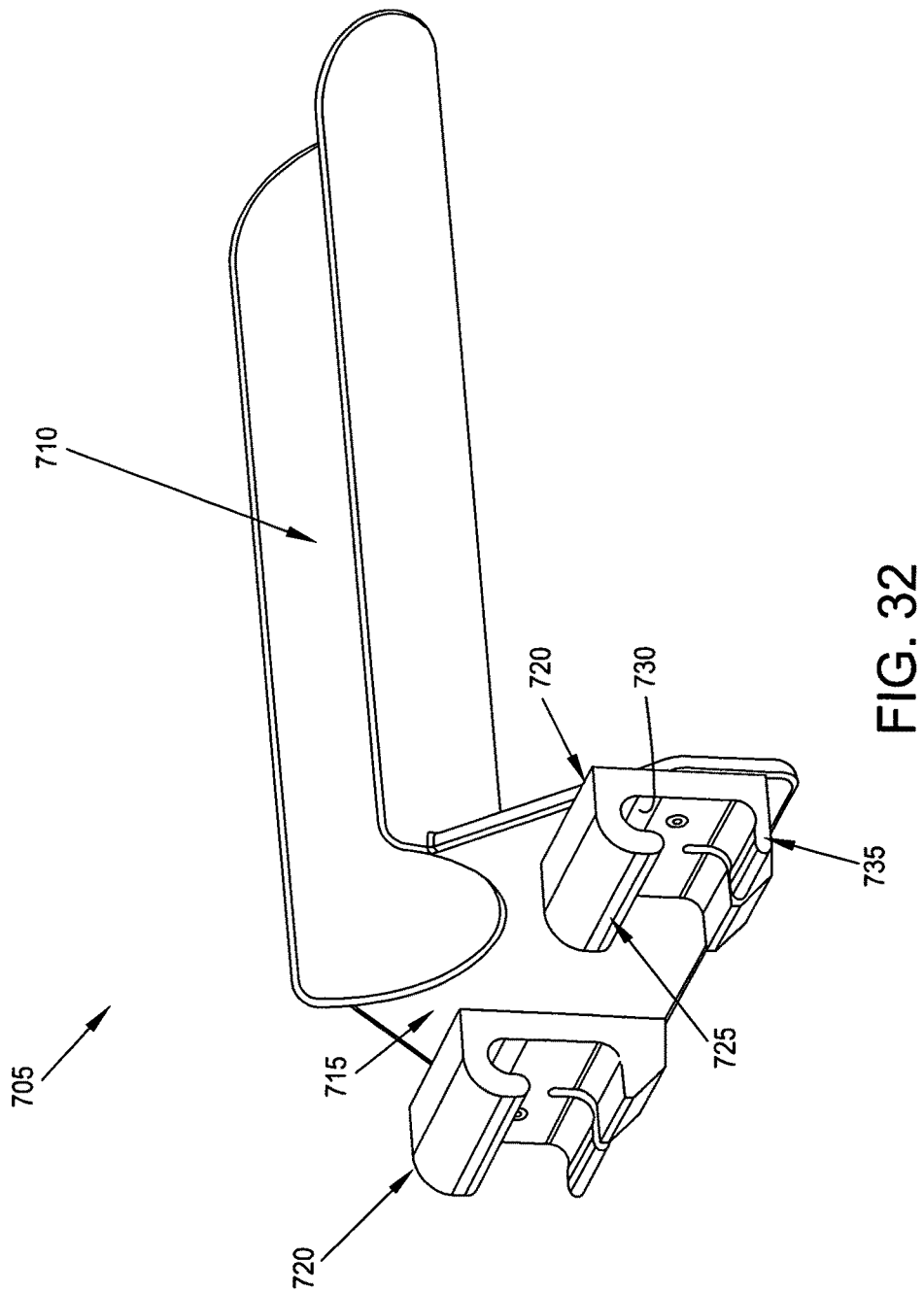
Figure 33:
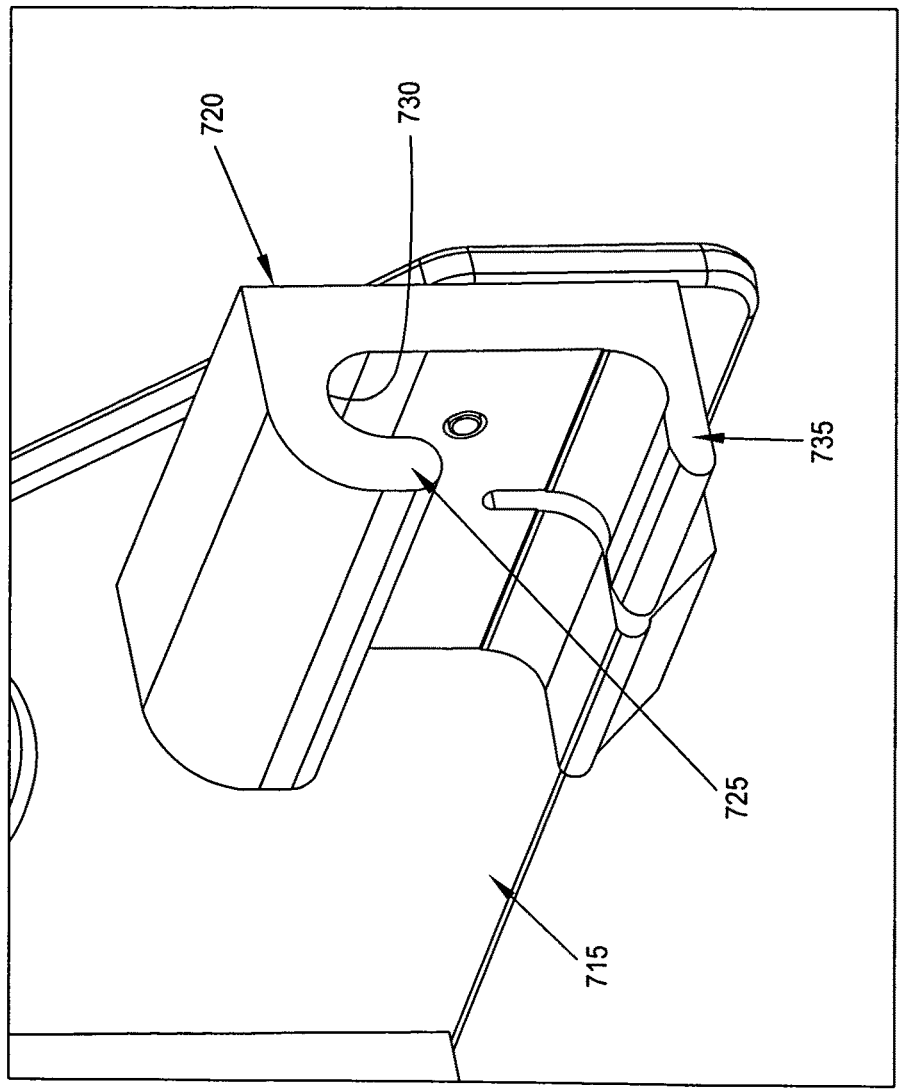
Figure 34:
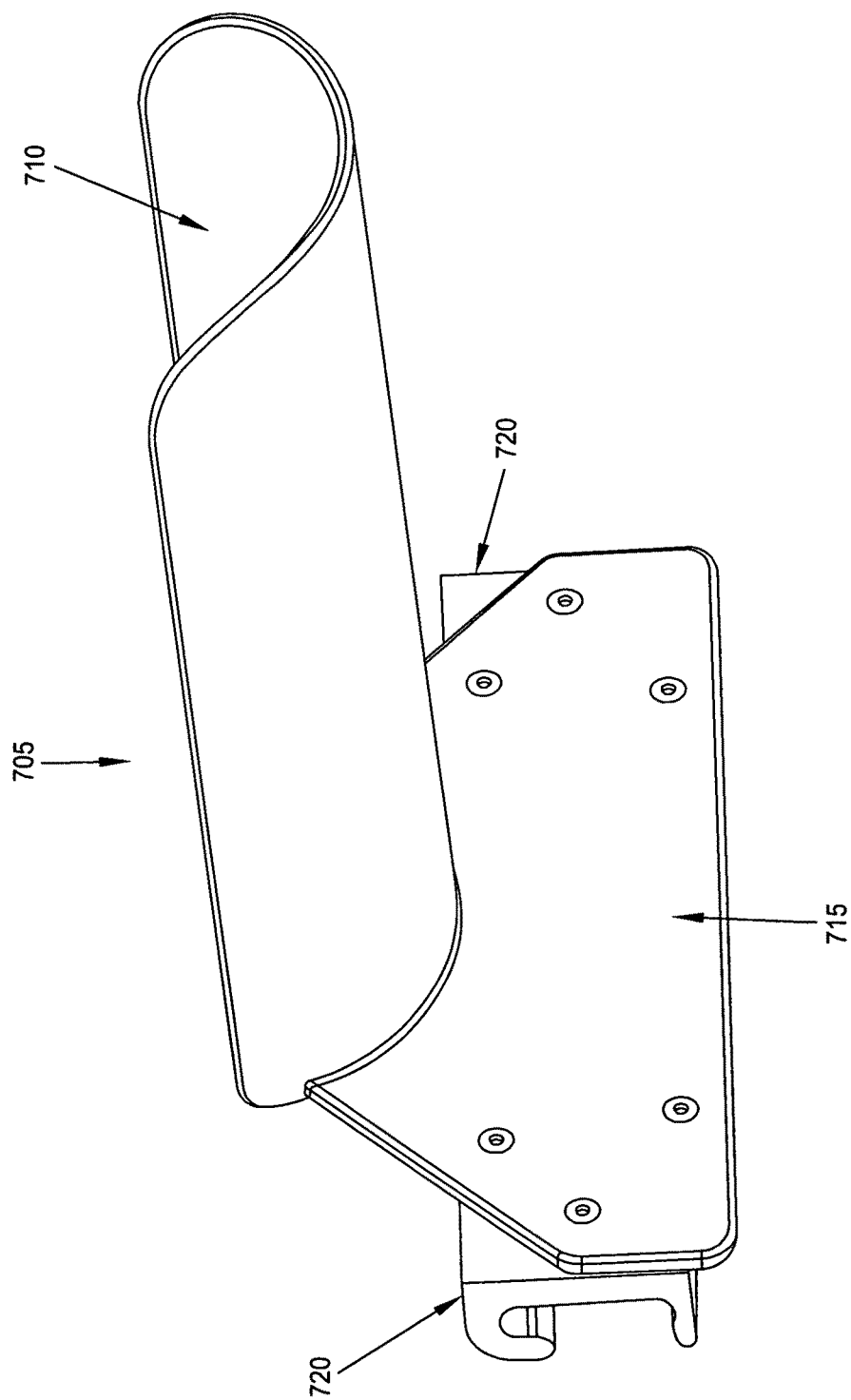
Figure 35:
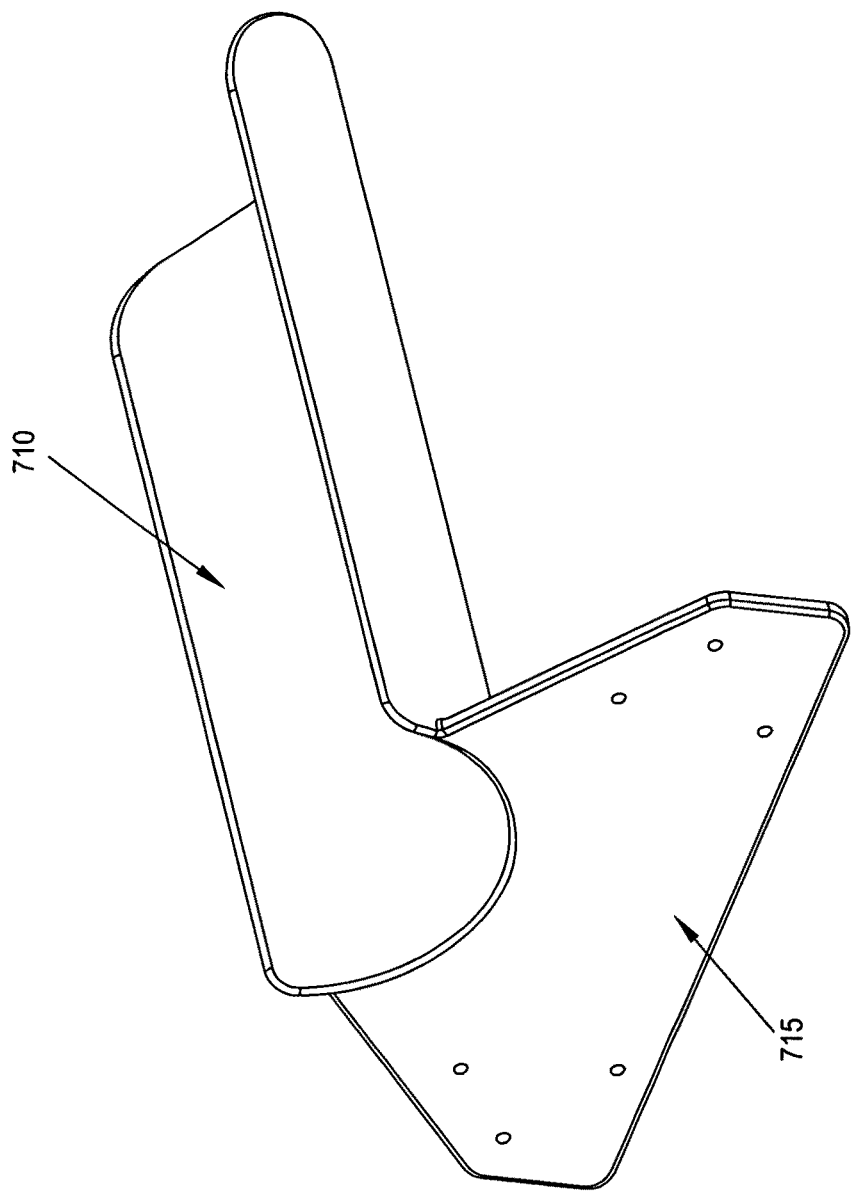
Figure 36:
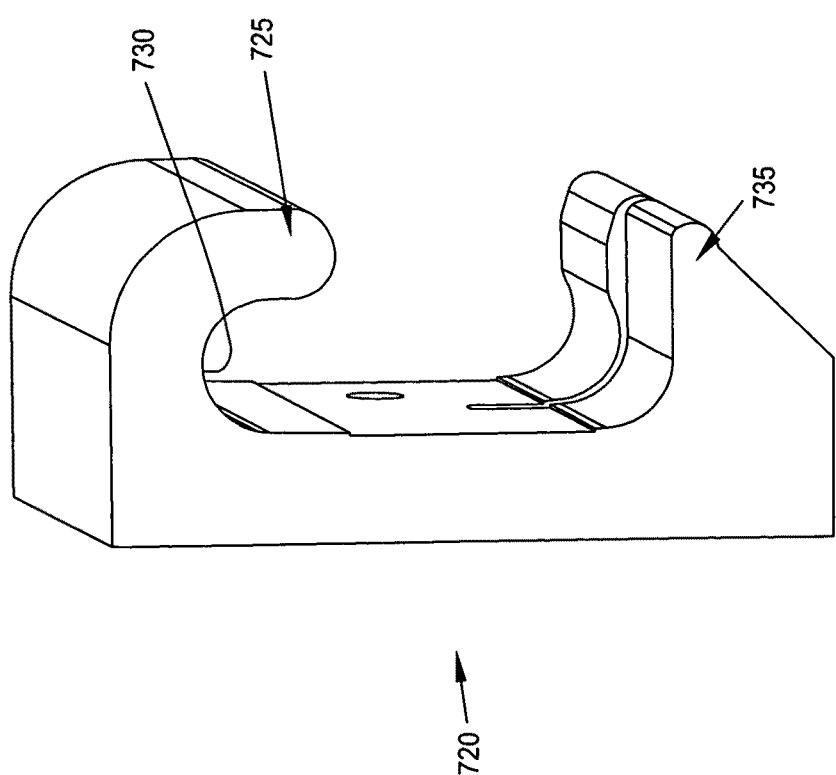
Figure 37:
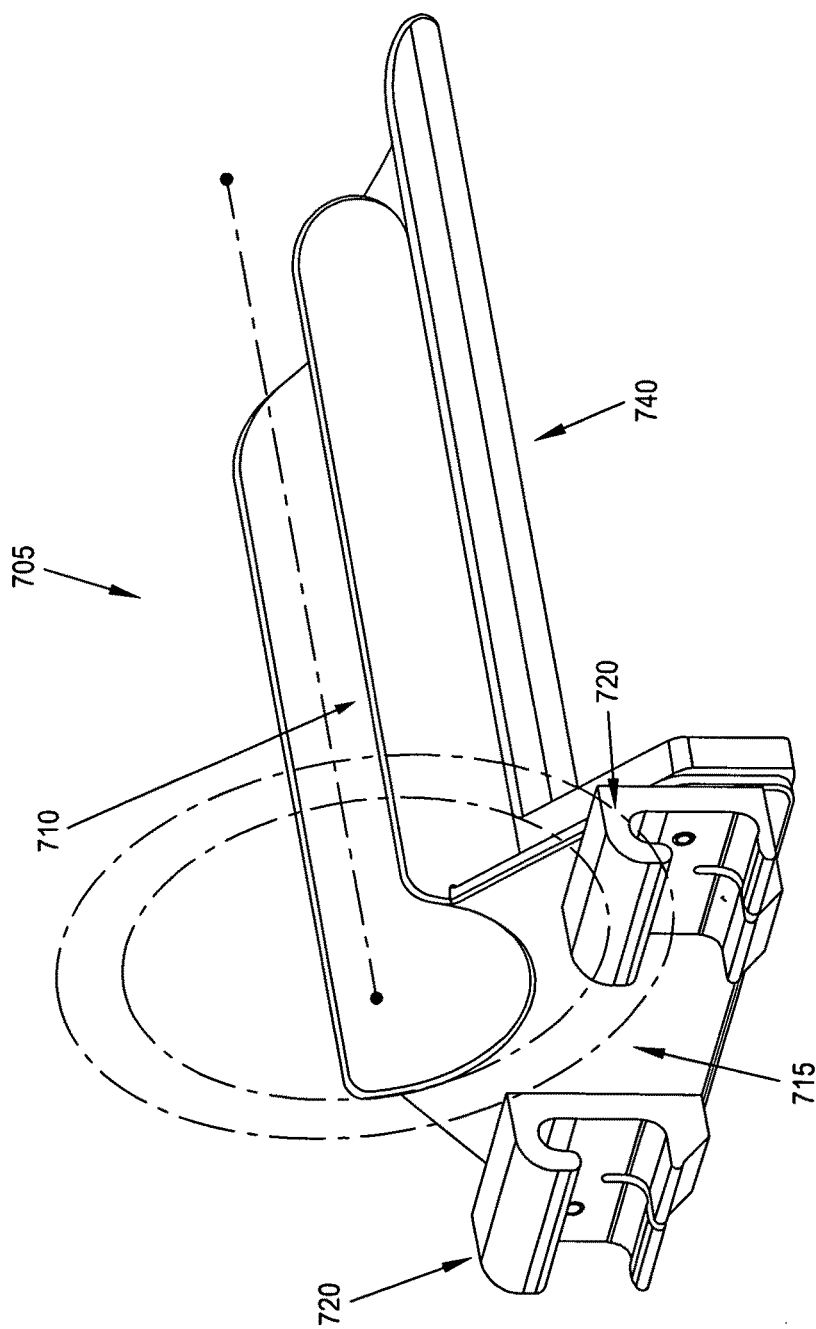

Thus, for example, in FIGS. 29 and 30, there is shown a support 700 for supporting the anatomy of a patient (e.g., the body of an infant) during scanning. Support 700 generally comprises a holder 705 and a movable stand 712. As seen in FIGS. 29-38, holder 705 comprises an X-ray transparent concave body 710 terminating in a plate 715 which has at least one mount 720 secured thereto. X-ray transparent concave body 710 is preferably sized to receive the body of an infant, although it can also be sized to receive a limb of a patient (e.g., an arm of a patient). Each mount 720 includes an upper lipped overhang 725 defining a recess 730 and a lower ledge 735. If desired, holder 705 can also include a support platform 740 for providing additional support to the X-ray transparent concave body 710.

Figure 38:
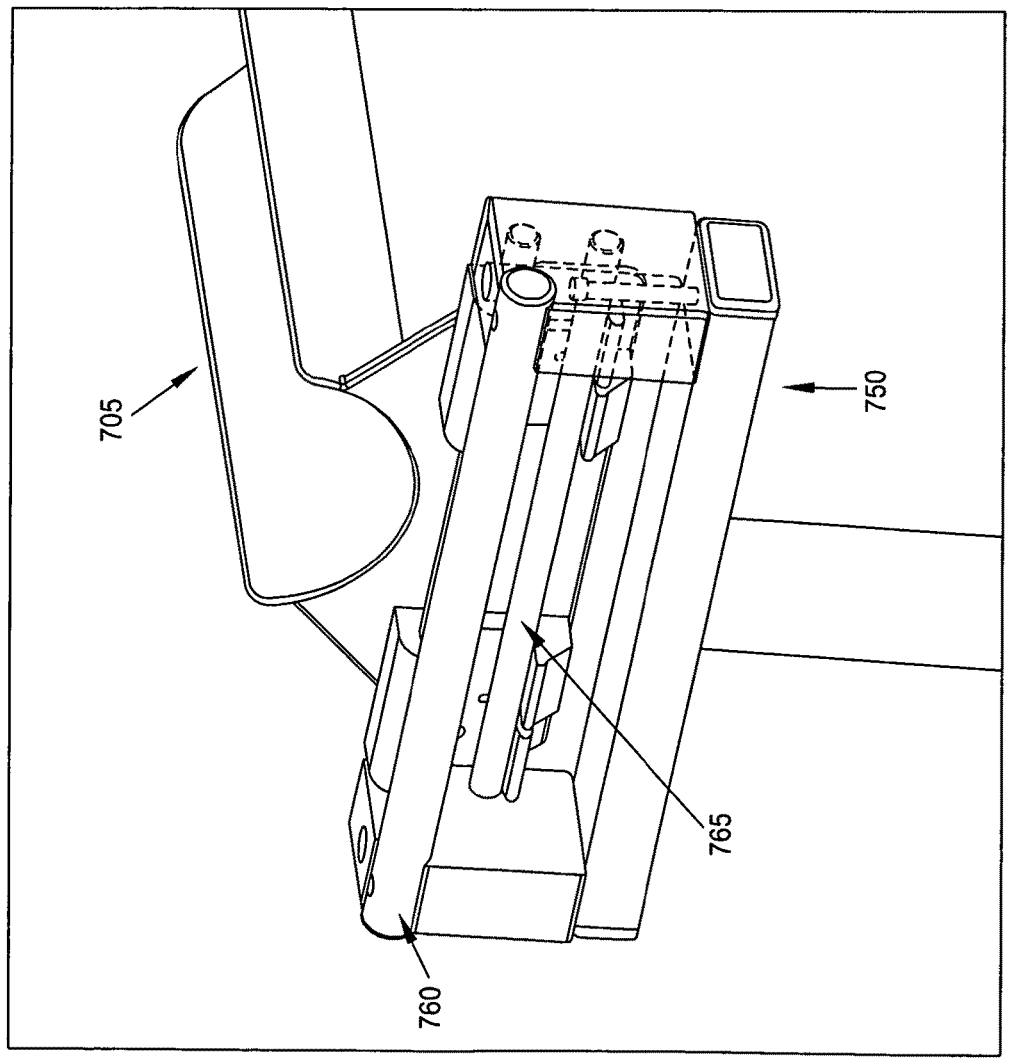
Figure 39:
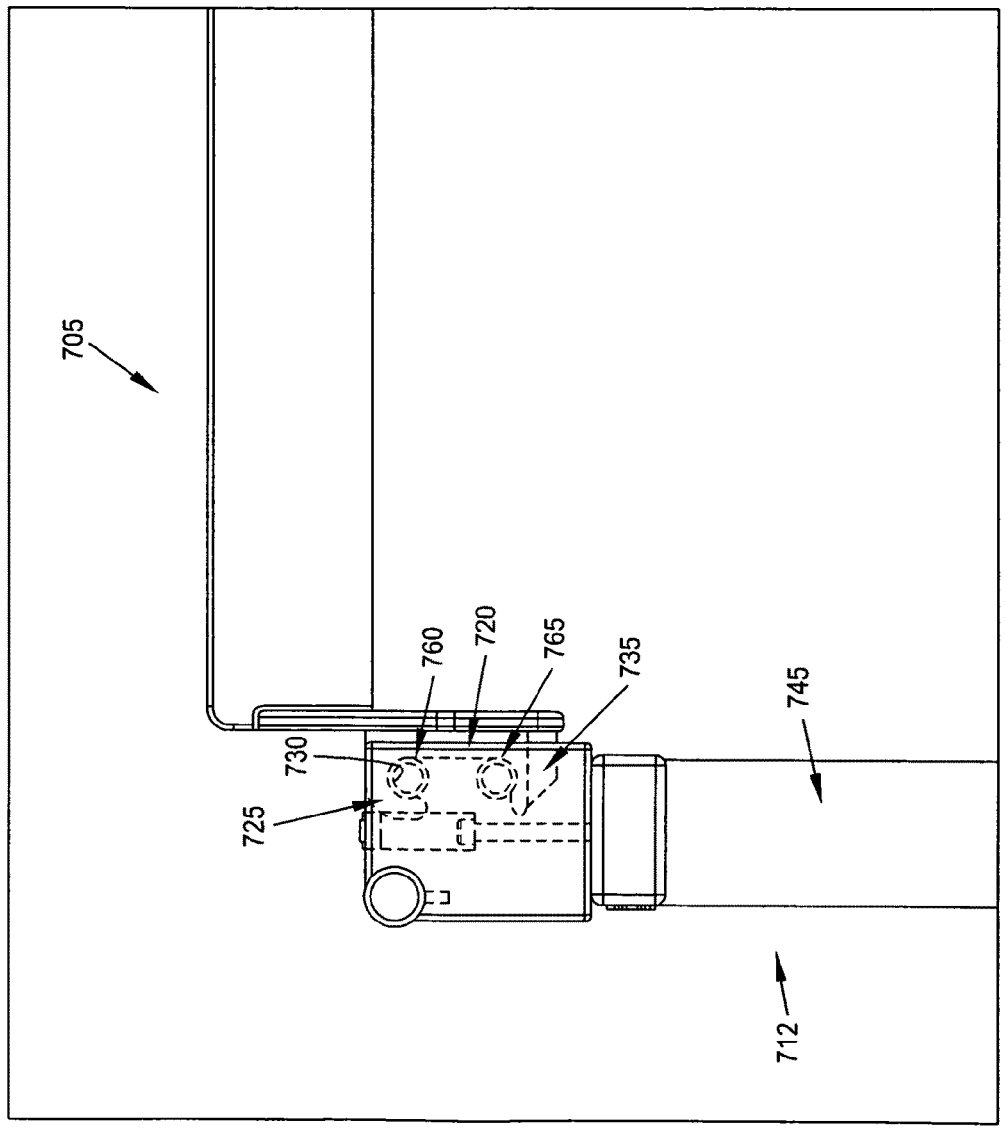
Figure 40:
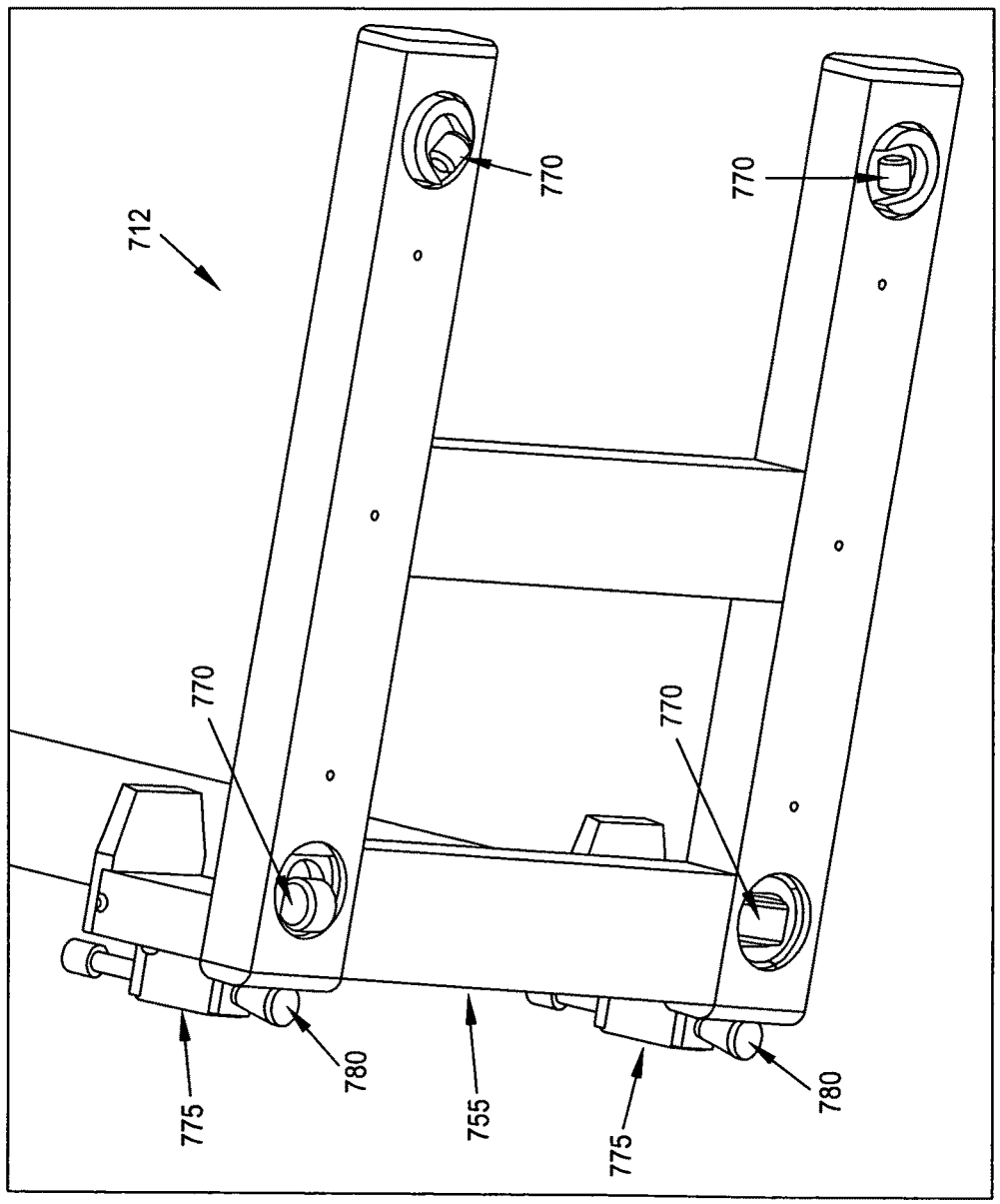
Figure 41:
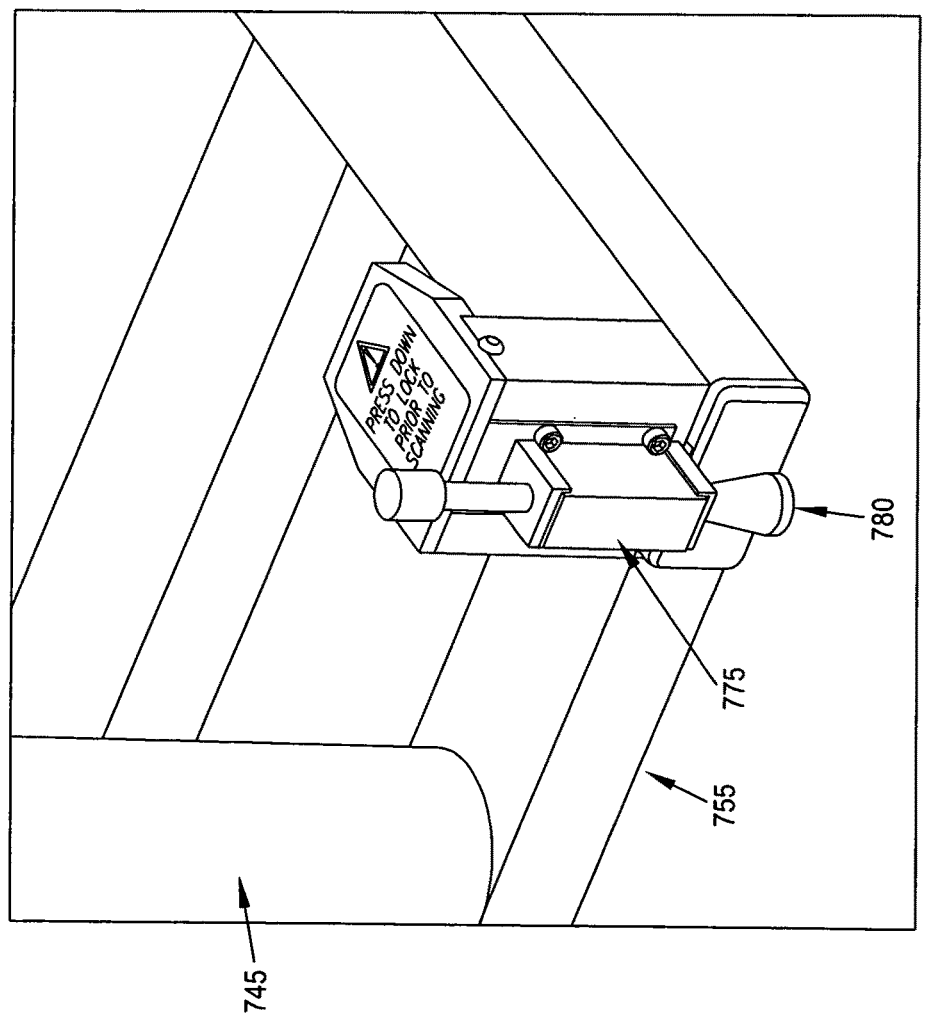

As seen in FIGS. 29 and 30, movable stand 712 comprises a riser 745 terminating in a head 750 at its upper end and in a base 755 at its lower end. Head 750 comprises a pair of horizontal bars 760, 765 (FIG. 38). The aforementioned holder 705 mounts to movable stand 712 by fitting the at least one mount 720 onto horizontal bars 760, 765. More particularly, holder 705 mounts to movable stand 712 by fitting the upper lipped overhang 725 of mount 720 over upper horizontal bar 760 so that upper horizontal bar 760 is received in recess 730, and then rotating holder 705 downward (i.e., counterclockwise in FIG. 39) until the lower horizontal bar 765 is engaged by lower ledge 735 of mount 720 (see FIG. 39). The base of movable stand 712 comprises casters 770 (FIG. 40) which permit movable stand 712 to move easily about on a floor, and includes a pair of brakes 775 having non-skid feet 780 for selectively stopping movement of movable stand 712 on a floor.

Figure 42:
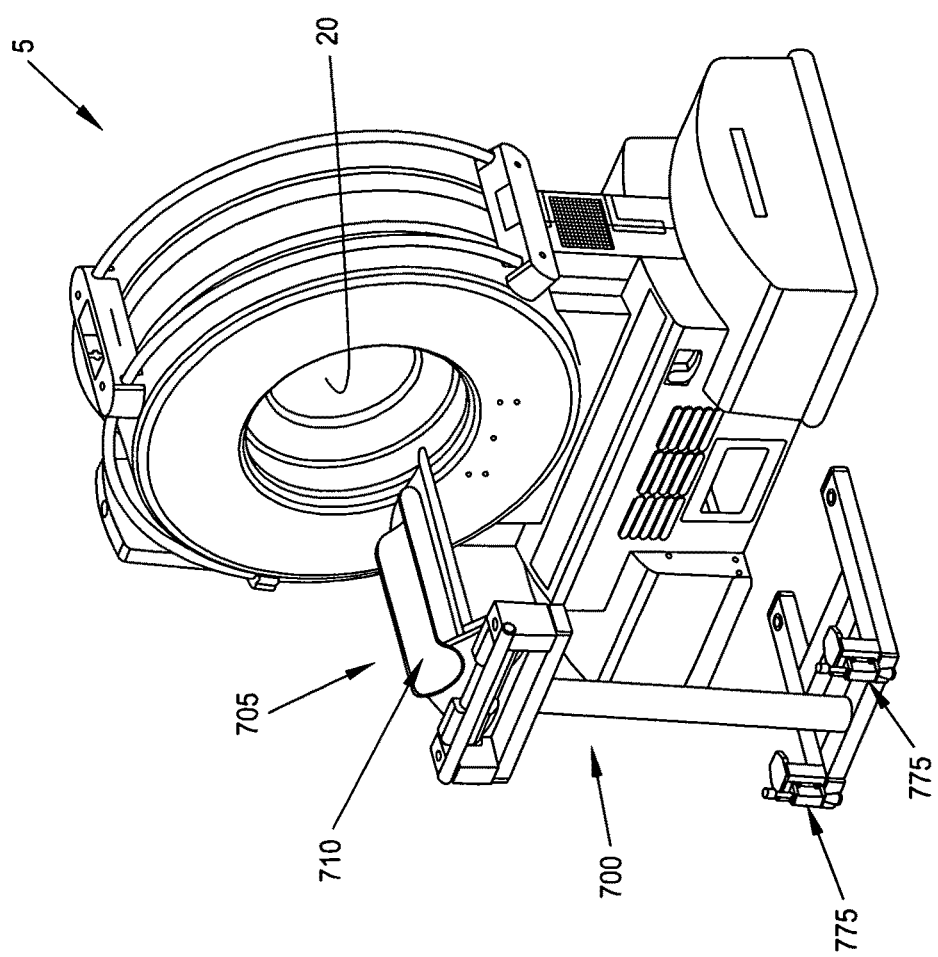
Figure 43:
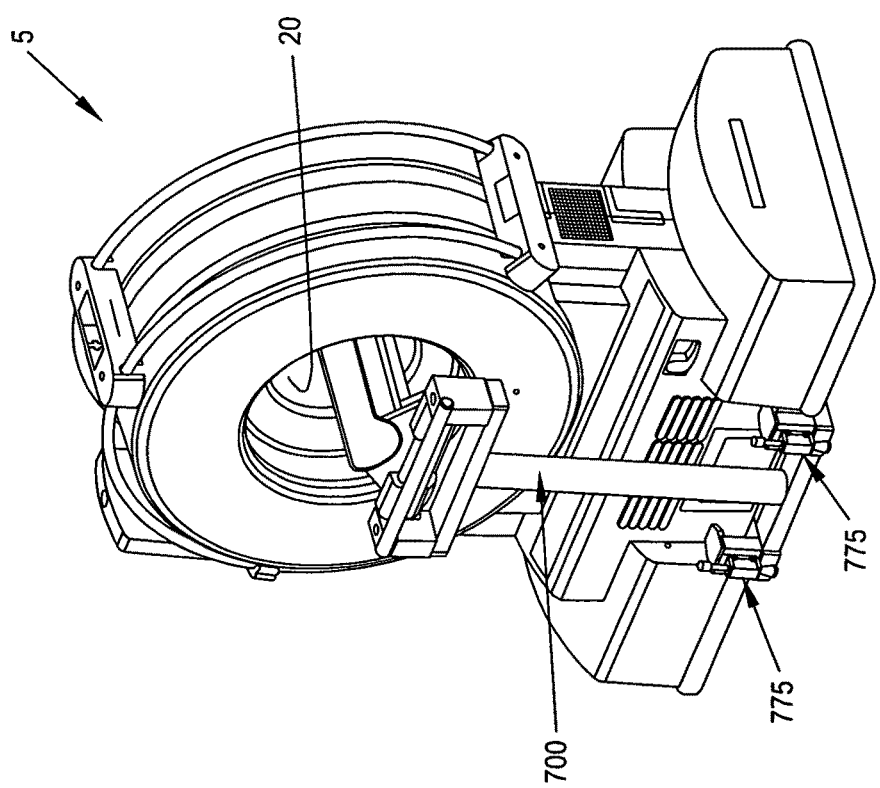
Figure 44:
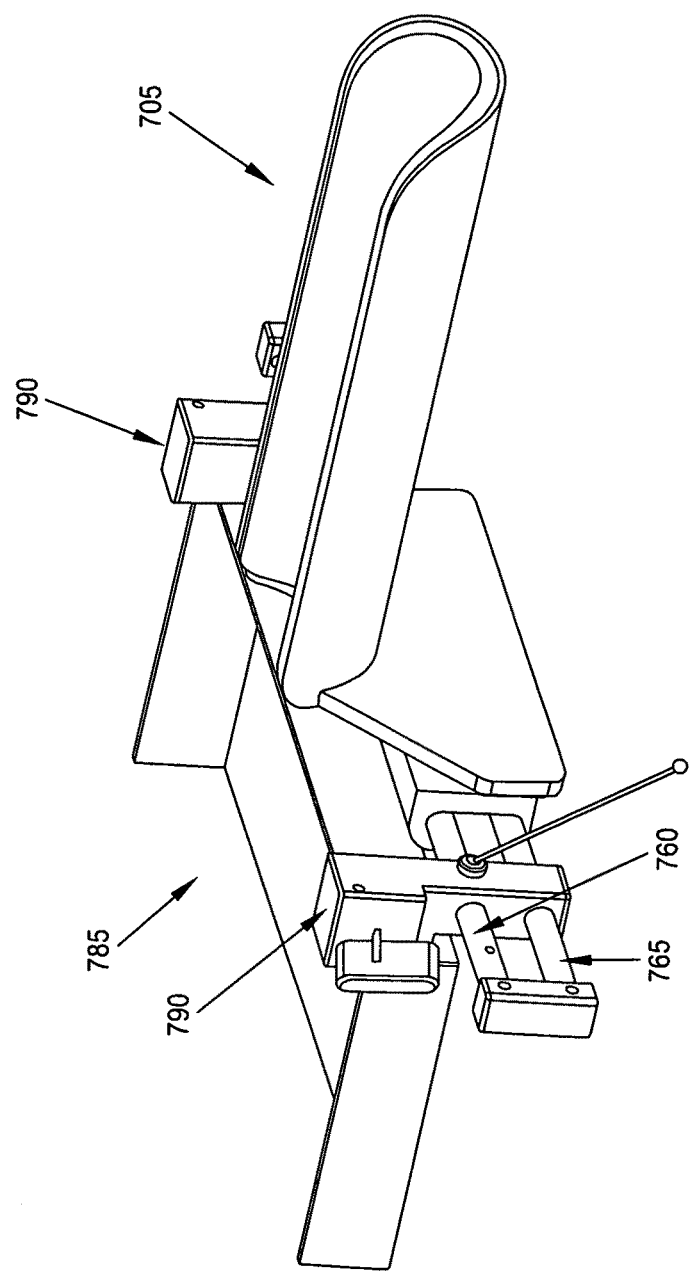
Figure 45:
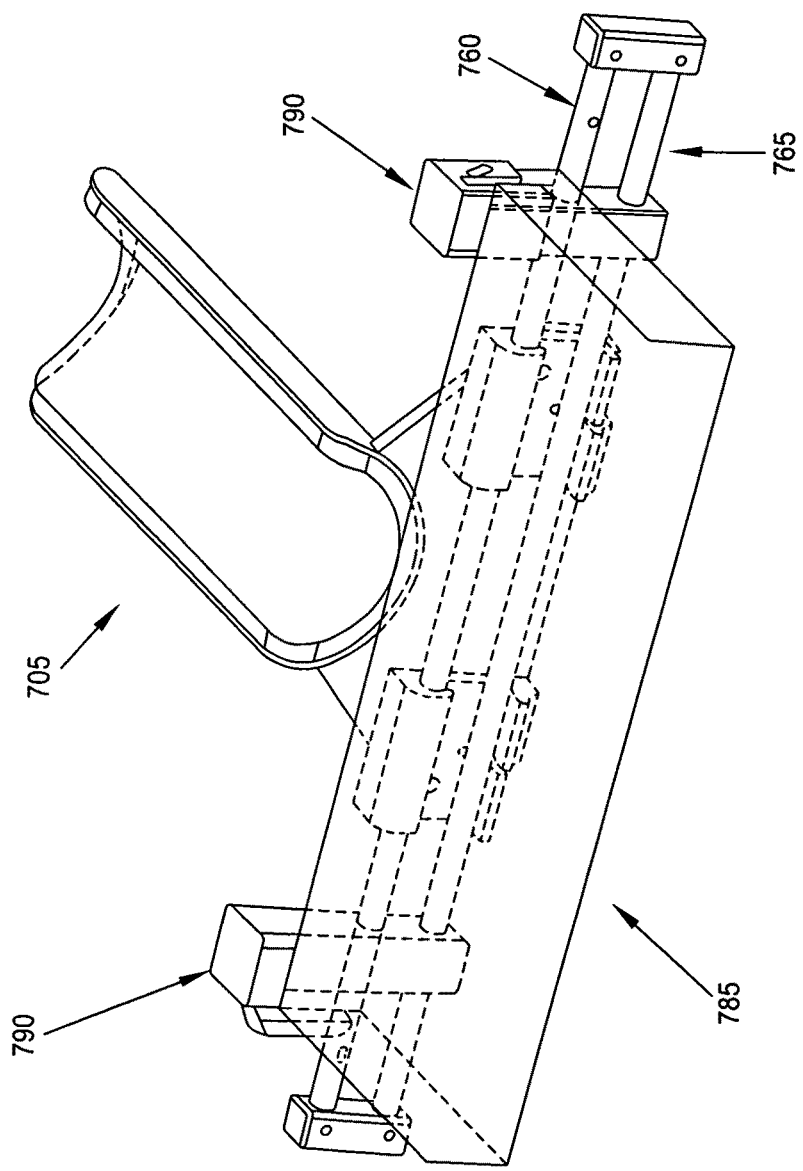
Figure 46:
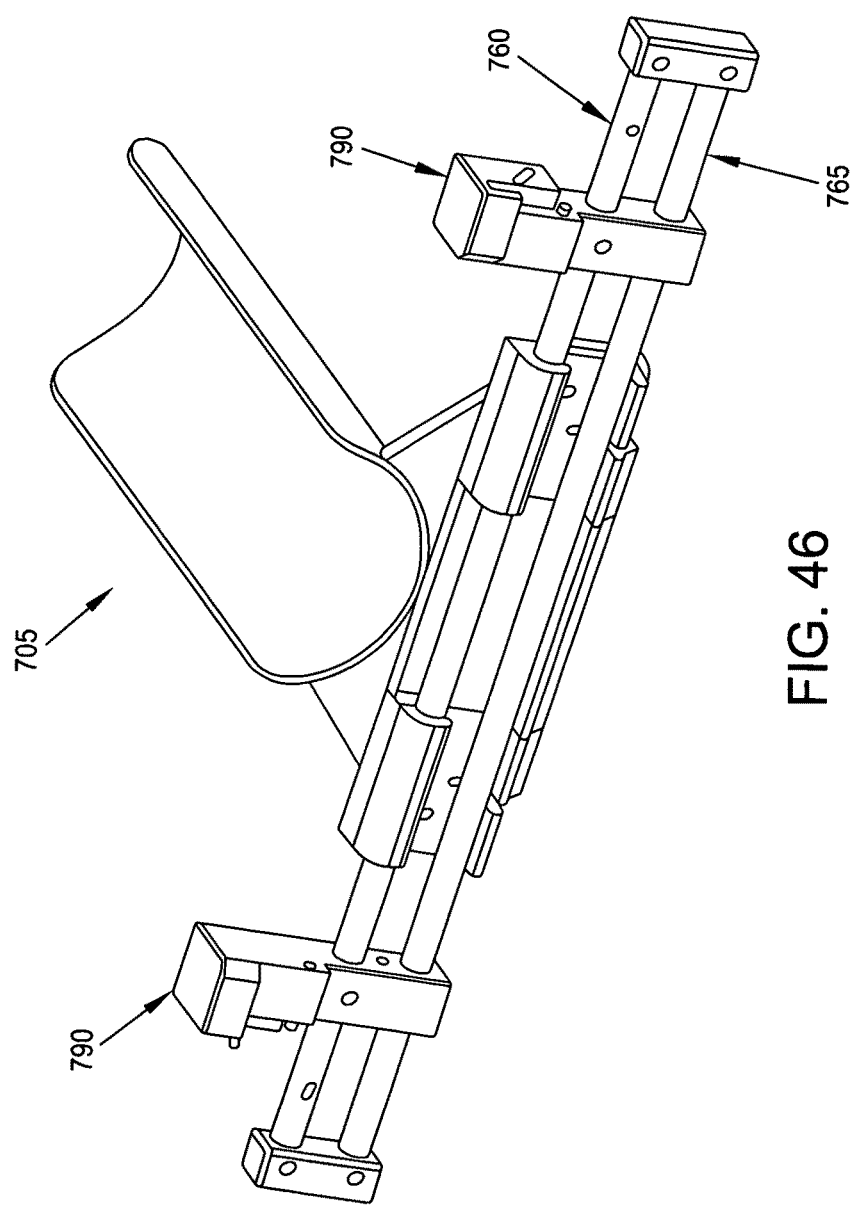
Figure 47:
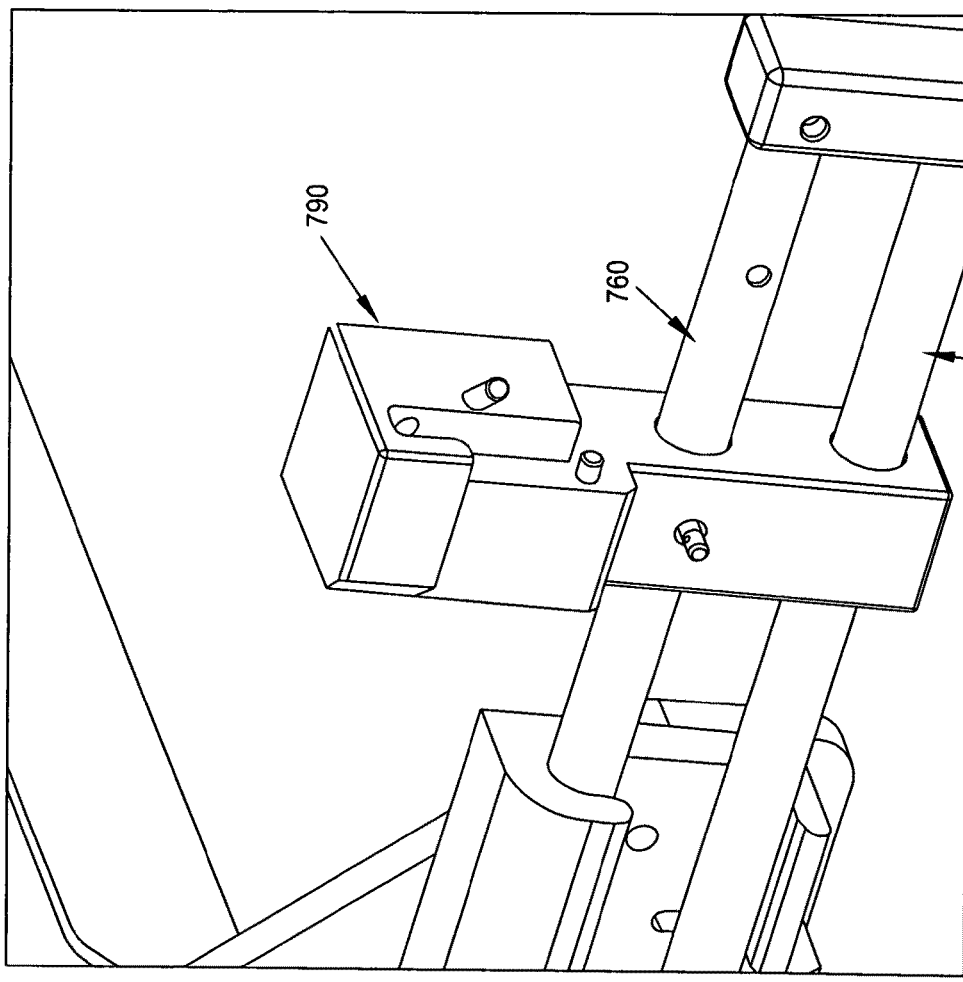
Figure 48:
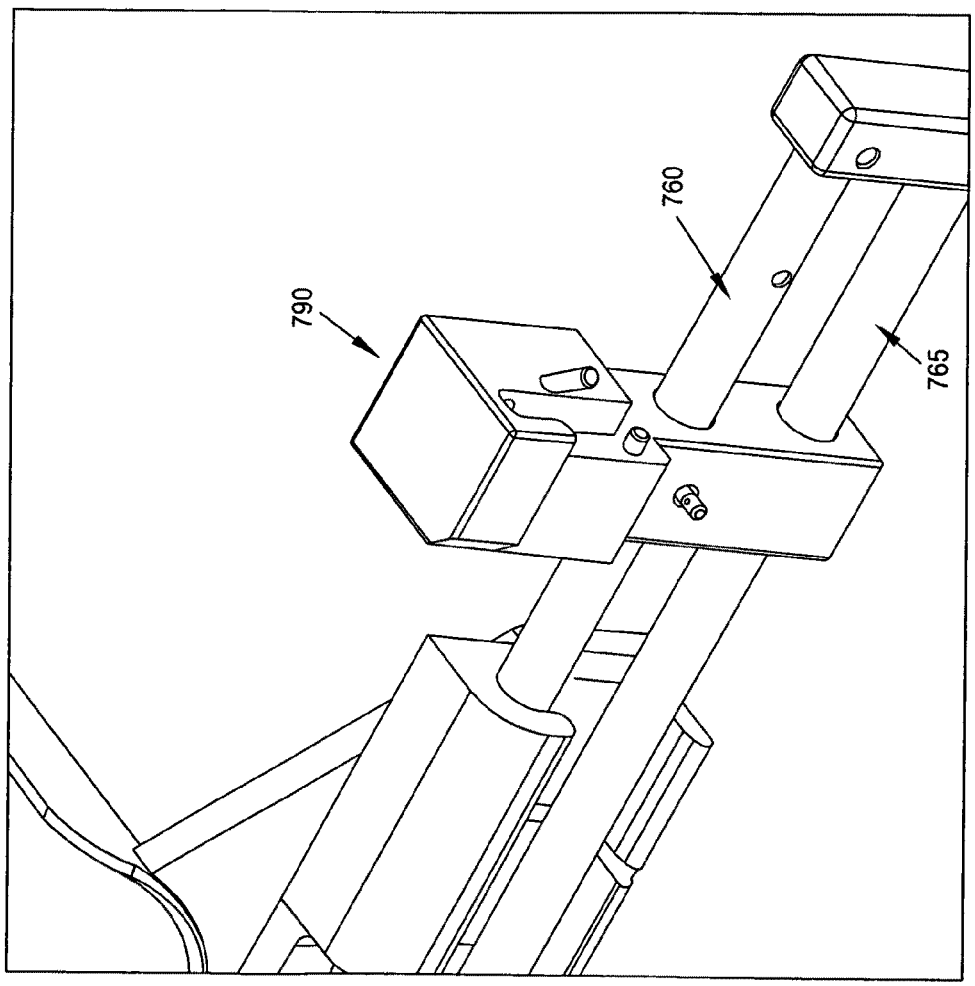
Figure 49:
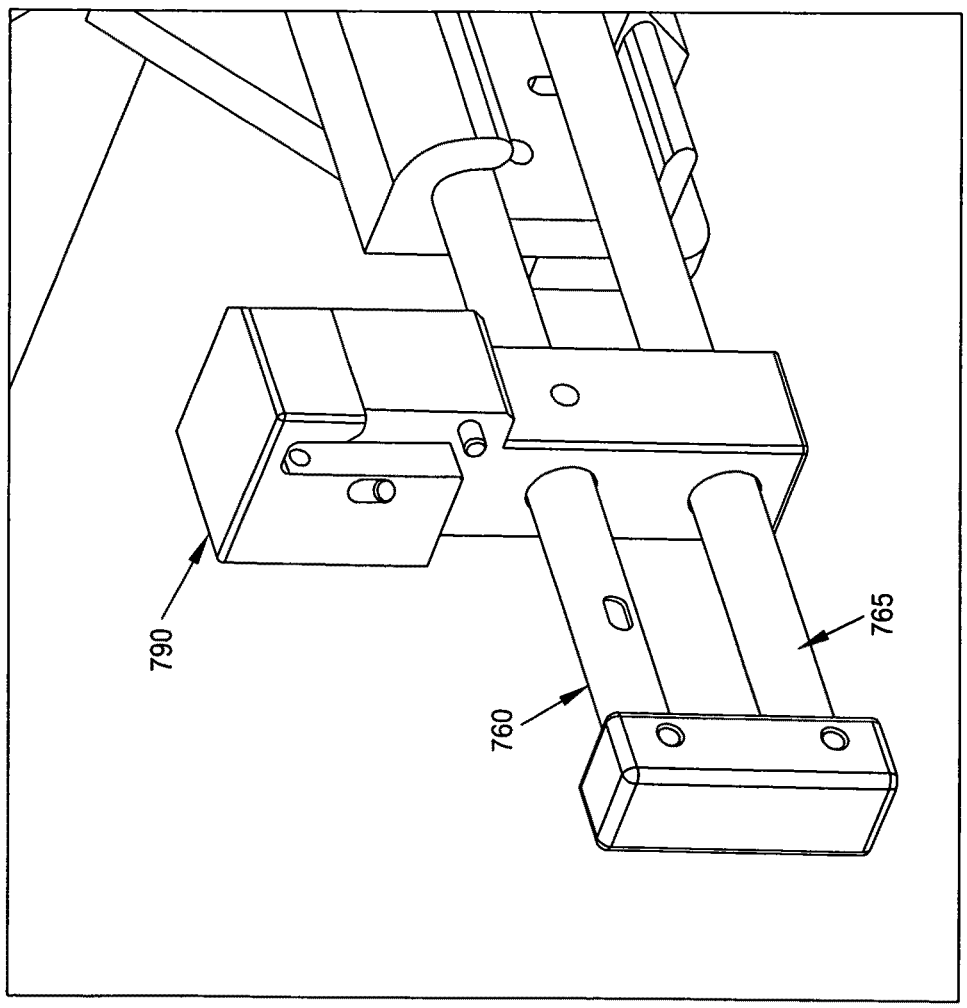
Figure 50:
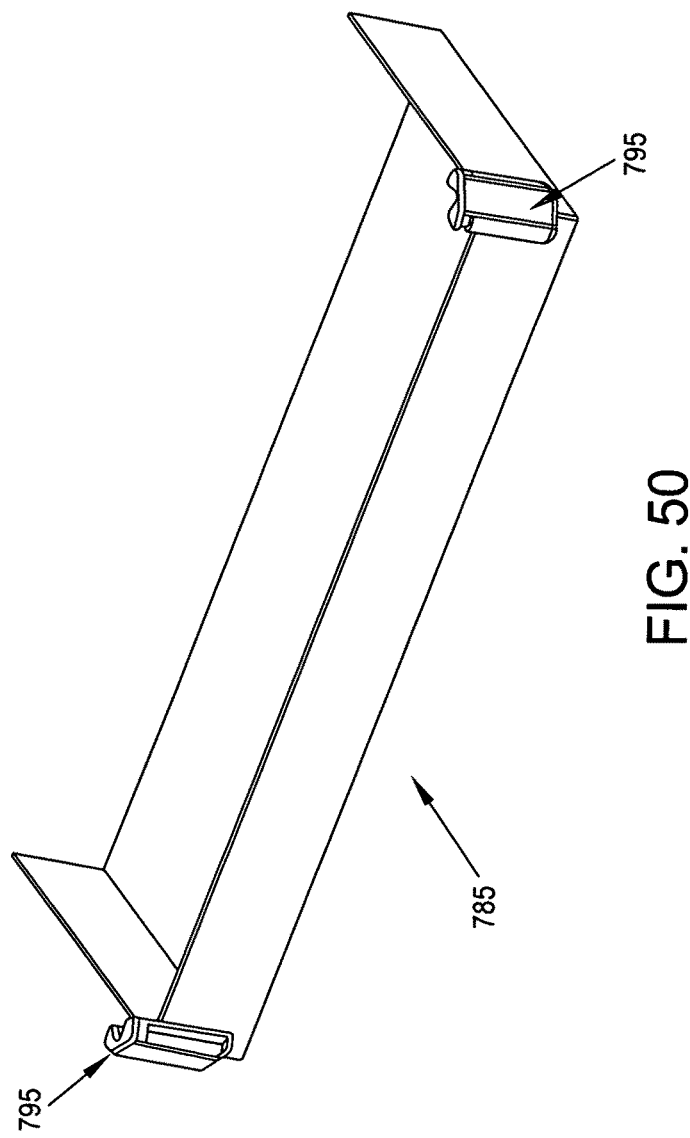
Figure 51:
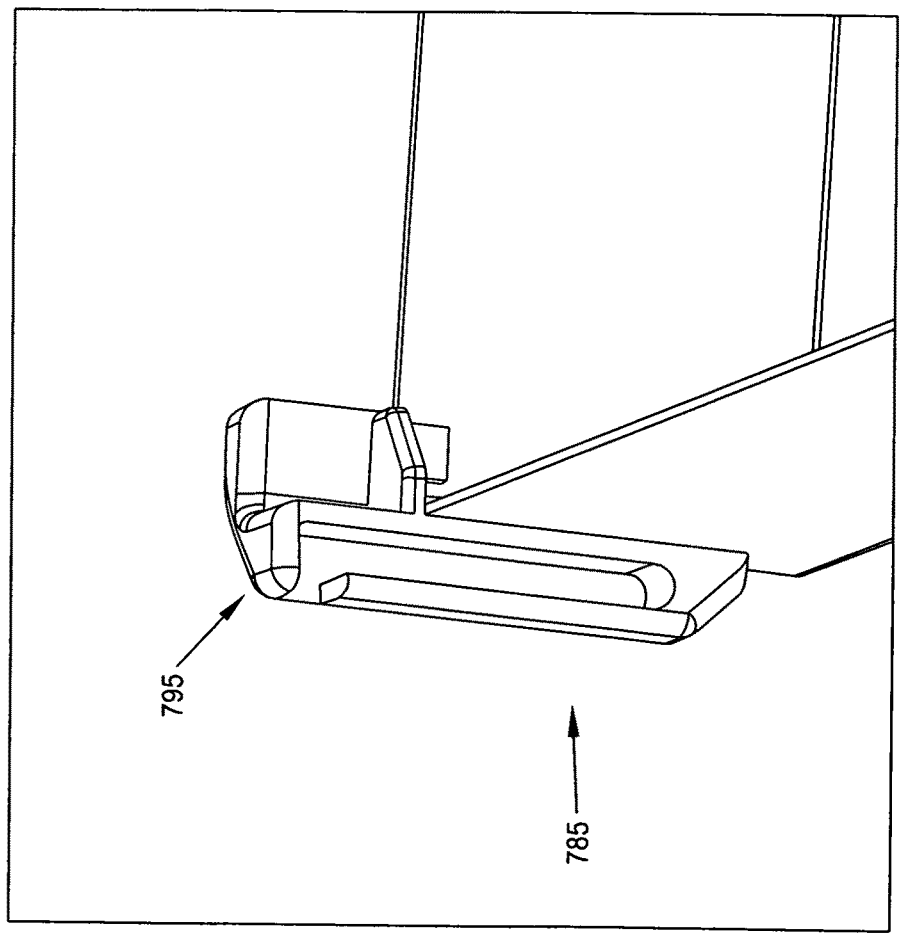
Figure 52:
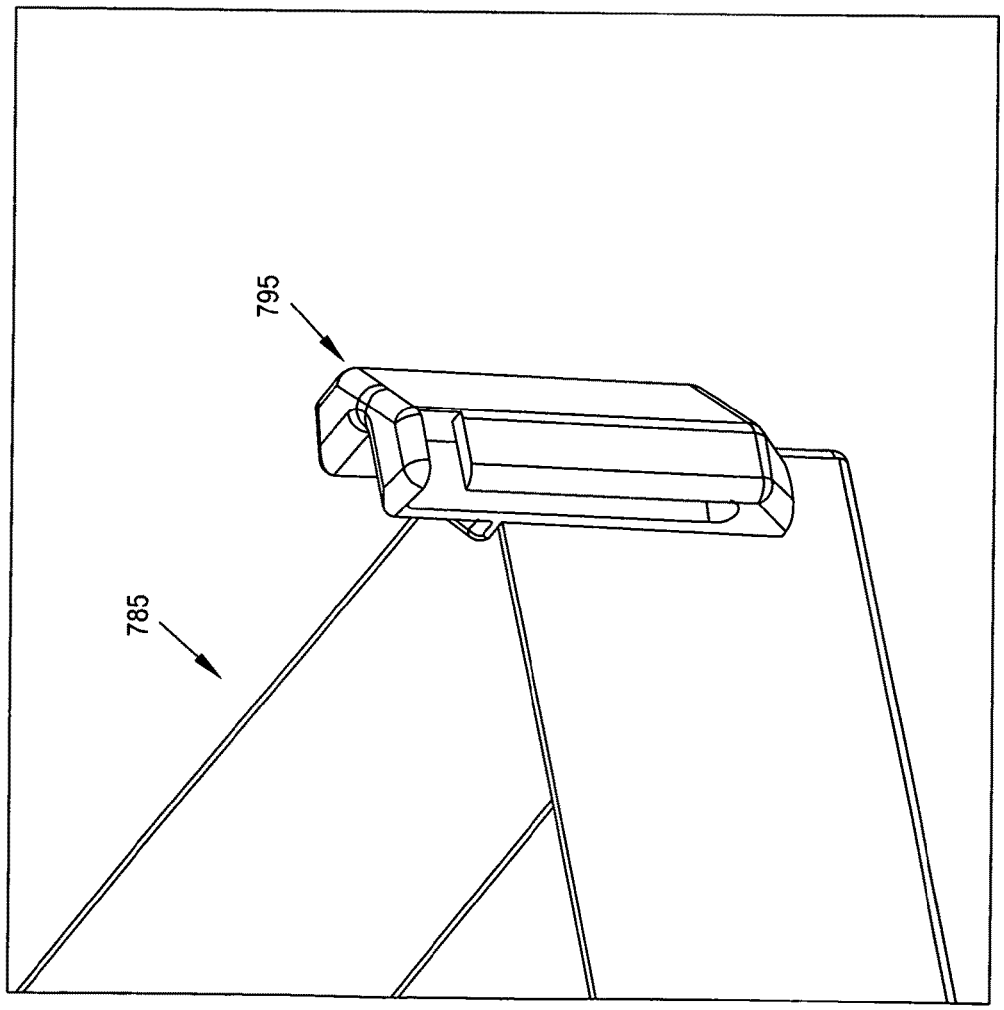
Figure 53:
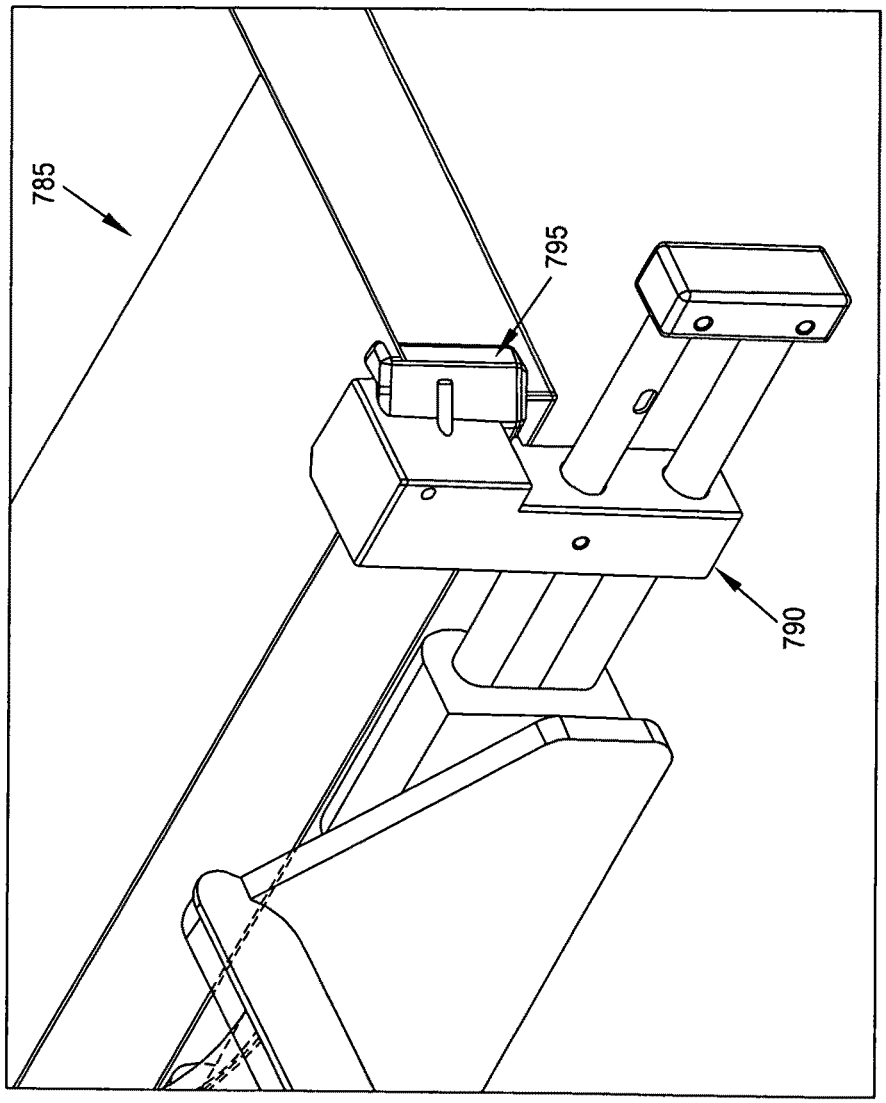
Figure 54:
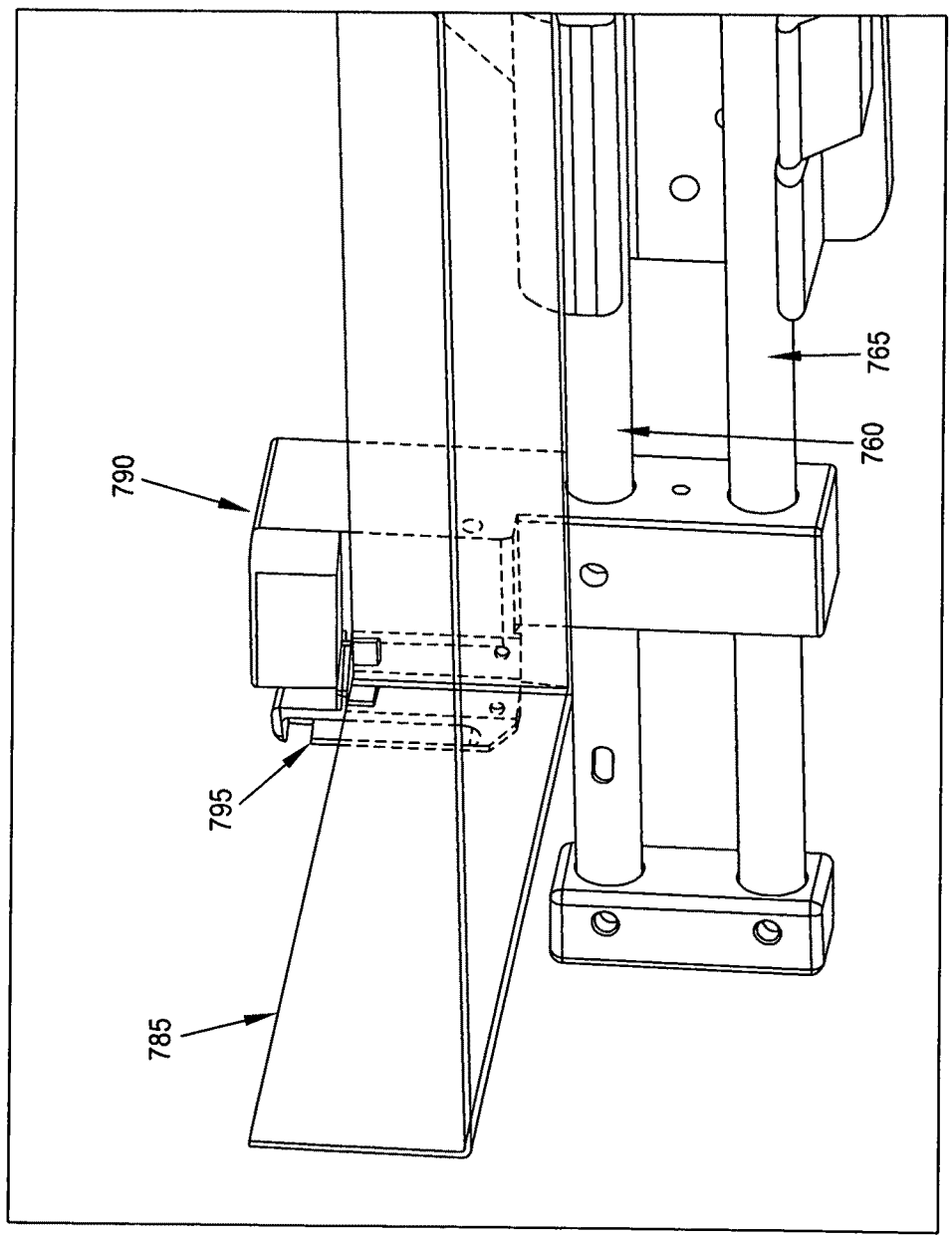
Figure 55:
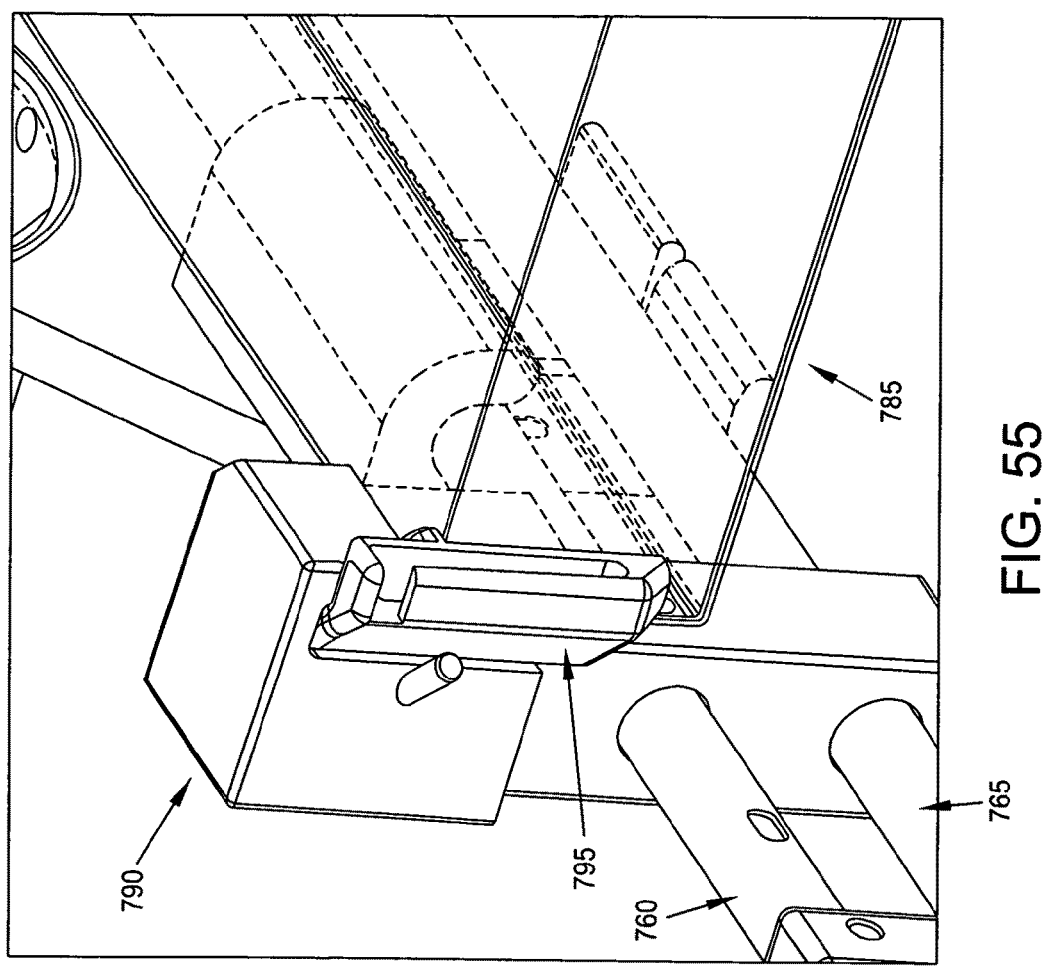
Figure 56:
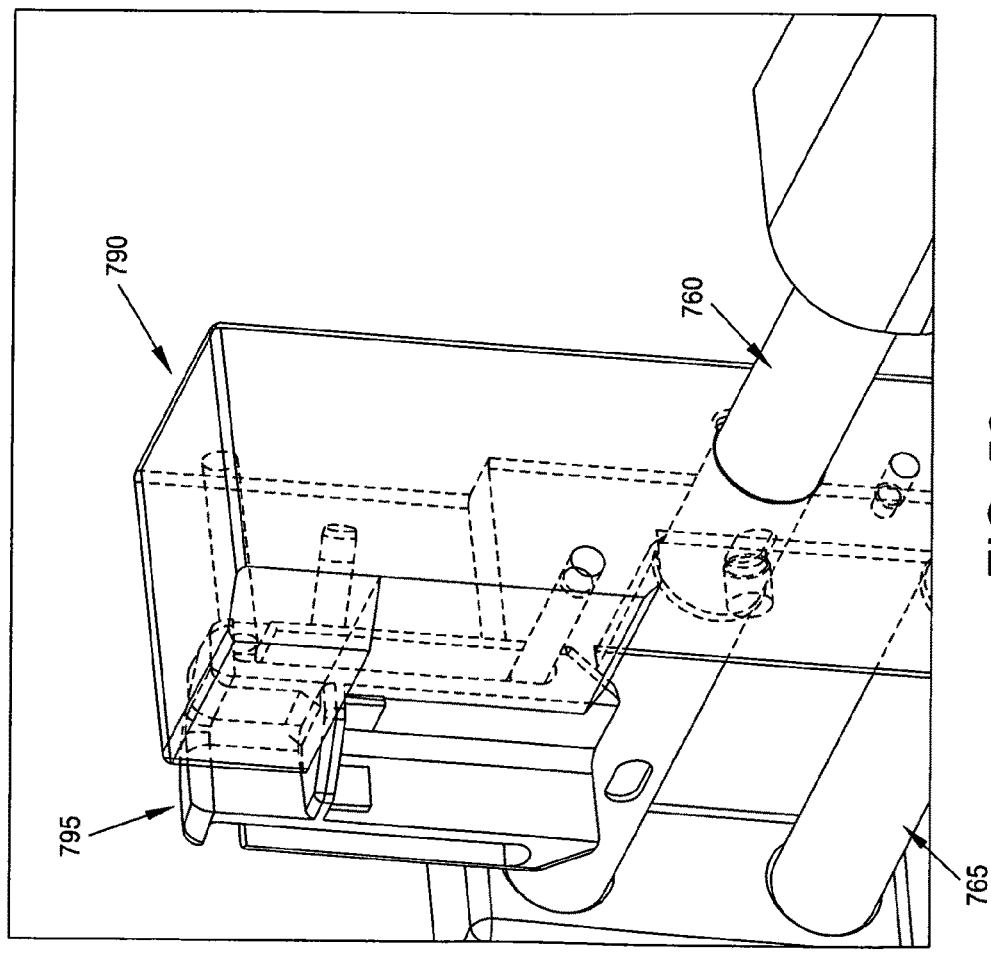
Figure 57:
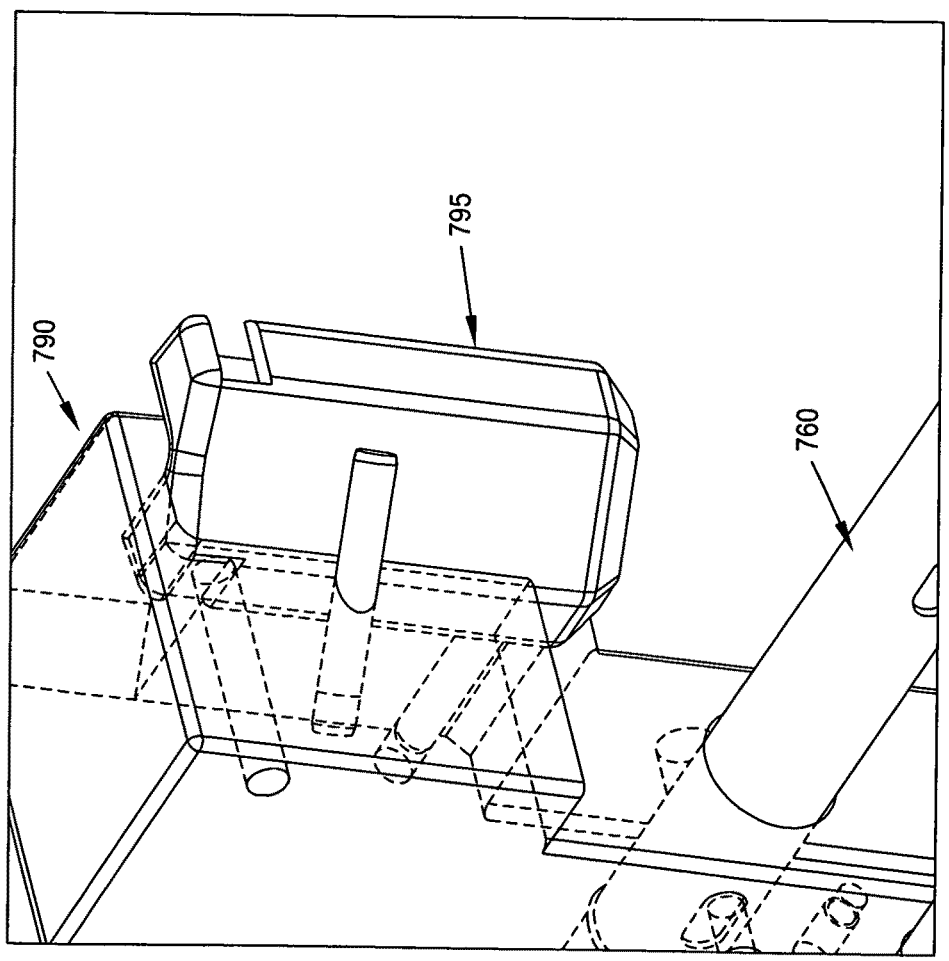

In use, and looking now at FIGS. 42 and 43, brakes 775 are set so that the non-skid feet 780 are engaged with the floor, the infant is placed in concave body 710, the brakes 775 are released so that the non-skid feet 780 are disengaged from the floor, and then support 700 is maneuvered so that its holder 705 sits adjacent to the center scan opening 20 of a Cere-Tom™ CT machine 5. Then brakes 775 are set so that non-skid feet 780 once again engage the floor and support 700 is locked in position. Scanning may then be conducted, with CereTom™ CT machine 5 moving relative to support 700 so as to effect scanning.

If desired, and looking now at FIGS. 44-57, a tray 785 may be mounted to head 750 of movable stand 712 so that tray 785 extends adjacent to, but in an opposite direction from, holder 705. Preferably, tray 785 is mounted to head 750 of movable stand 712 by mounting a pair of arms 790 to horizontal bars 760, 765, and then mounting tray 785 to arms 790. To this end, tray 785 may include corner brackets 795 which are adapted to engage arms 790.

It is also possible to provide an enlarged support (e.g., for a large baby or toddler) atop a movable stand.

3. Large Baby Support.

Thus, for example, and looking now at FIGS. 58-62, there is shown a support 800 for supporting the anatomy of a patient (e.g., the body of a large baby or toddler) during scanning. Support 800 may be used where, for example, the patient is too large to fit in the aforementioned support 700.

Figure 58:
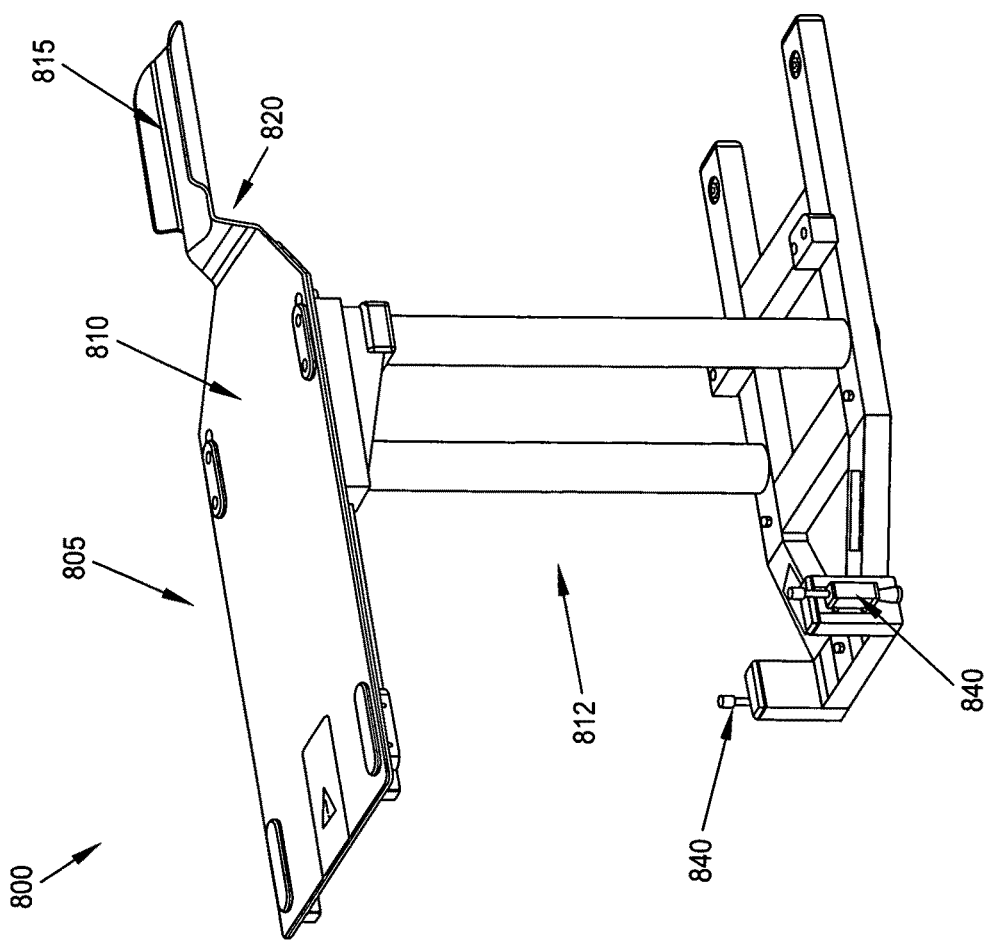
FIGS. 58-62 are schematic views showing a support for supporting anatomy of a patient (e.g., the body of a large baby or toddler) during scanning.
Figure 59:
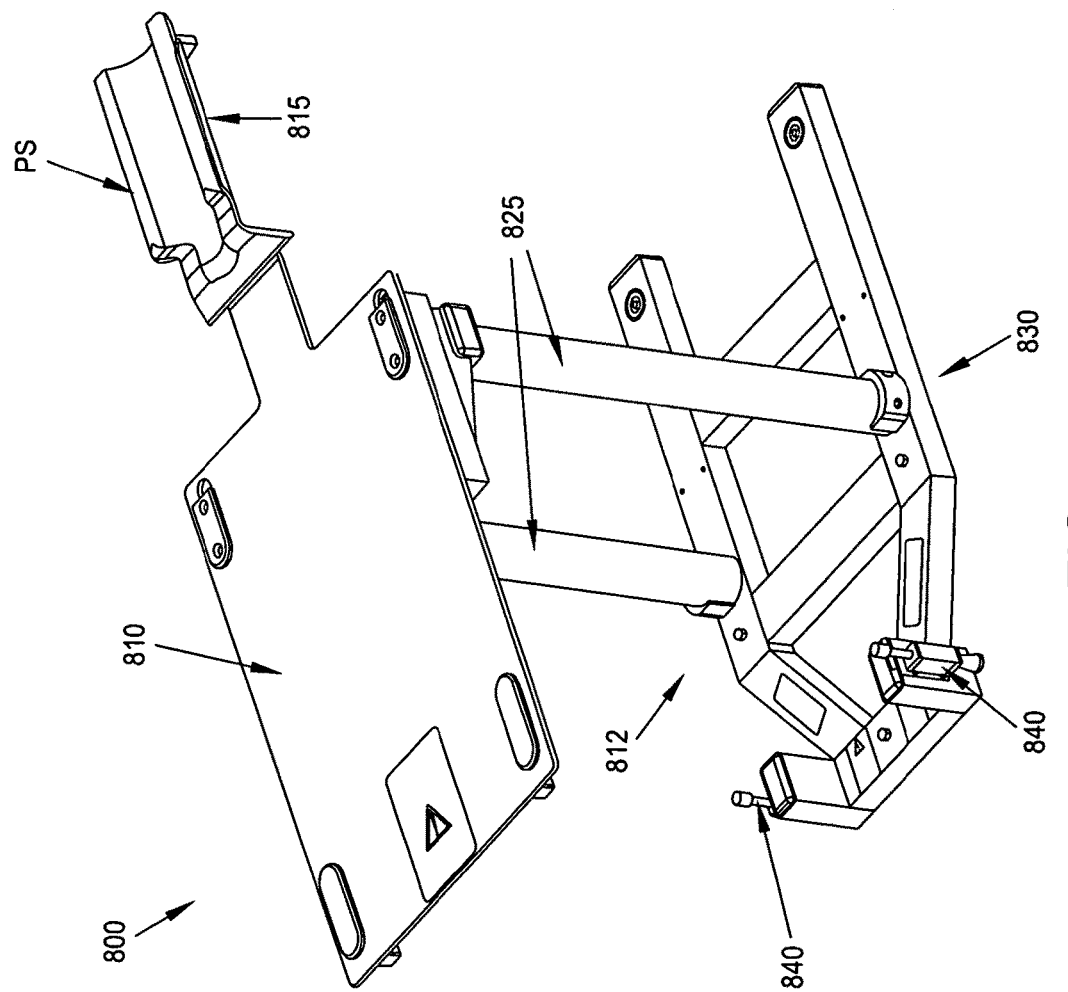
Figure 60:
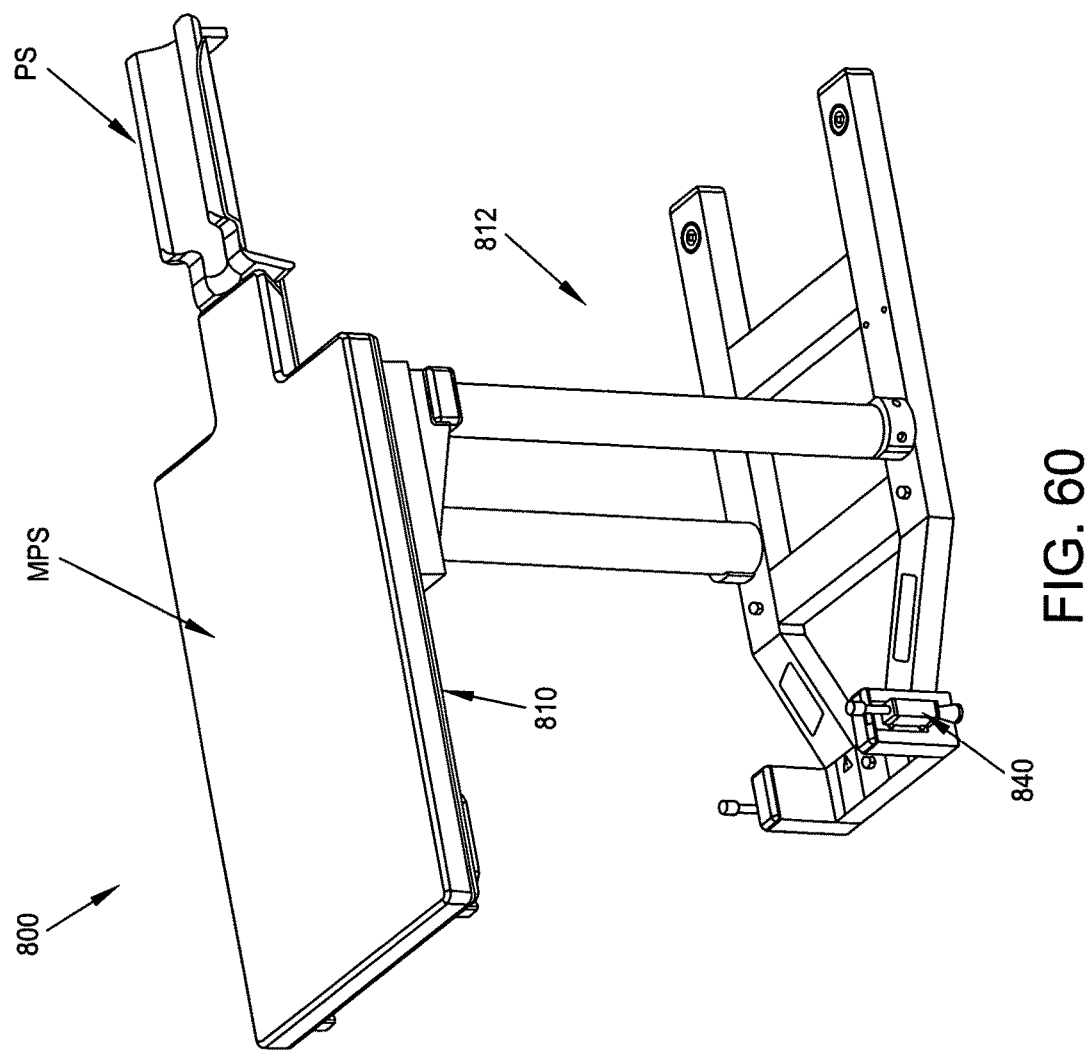
Figure 61:
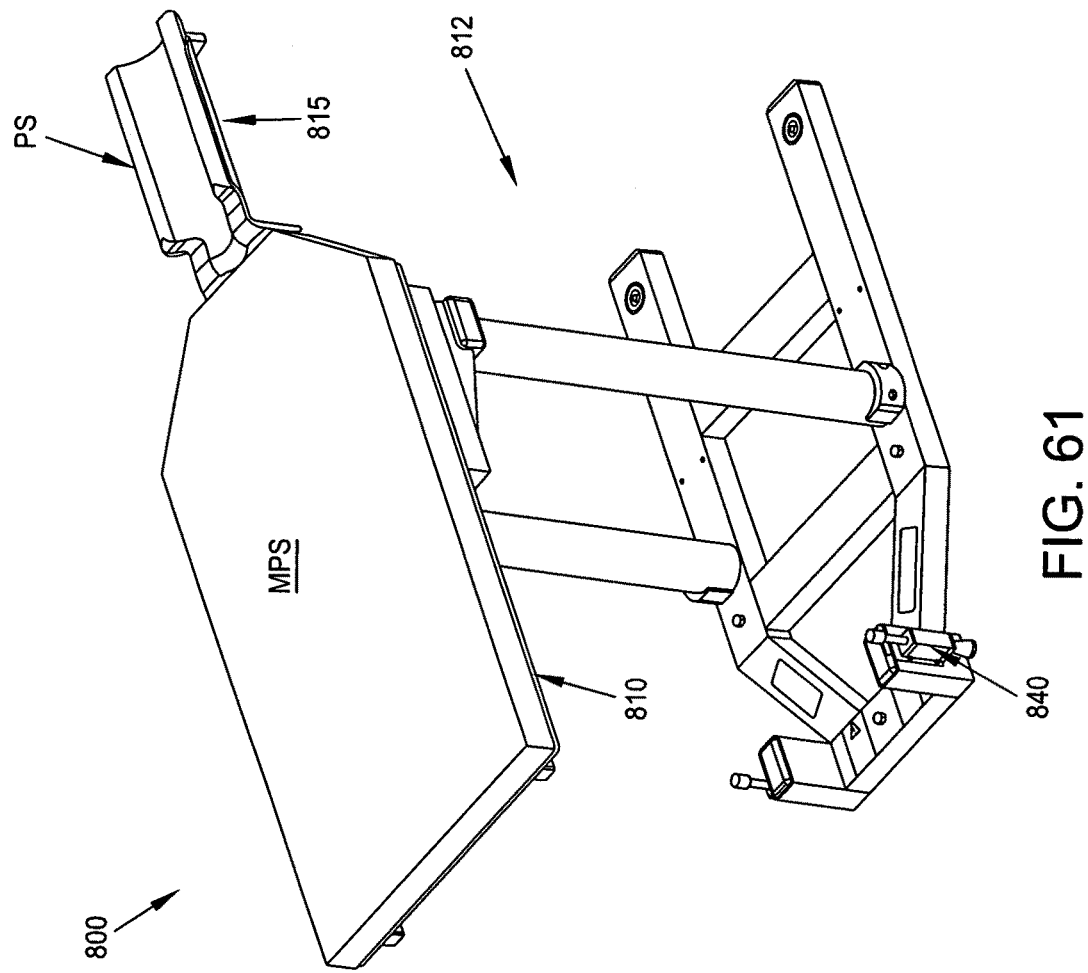
Figure 62:
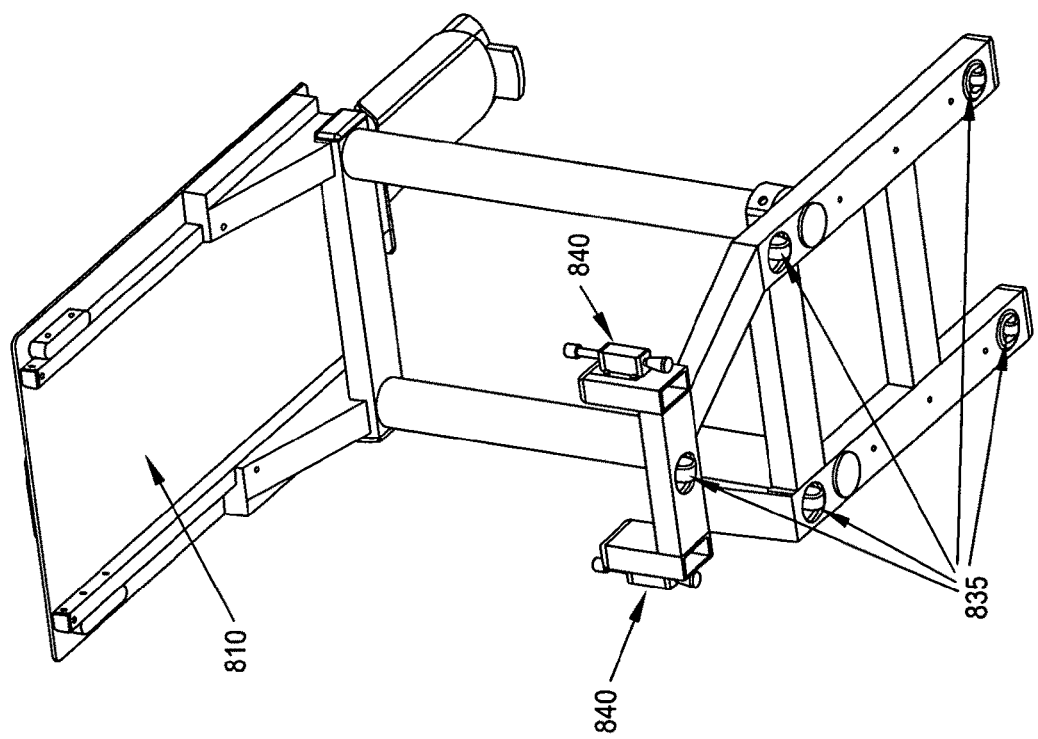
Figure 63:
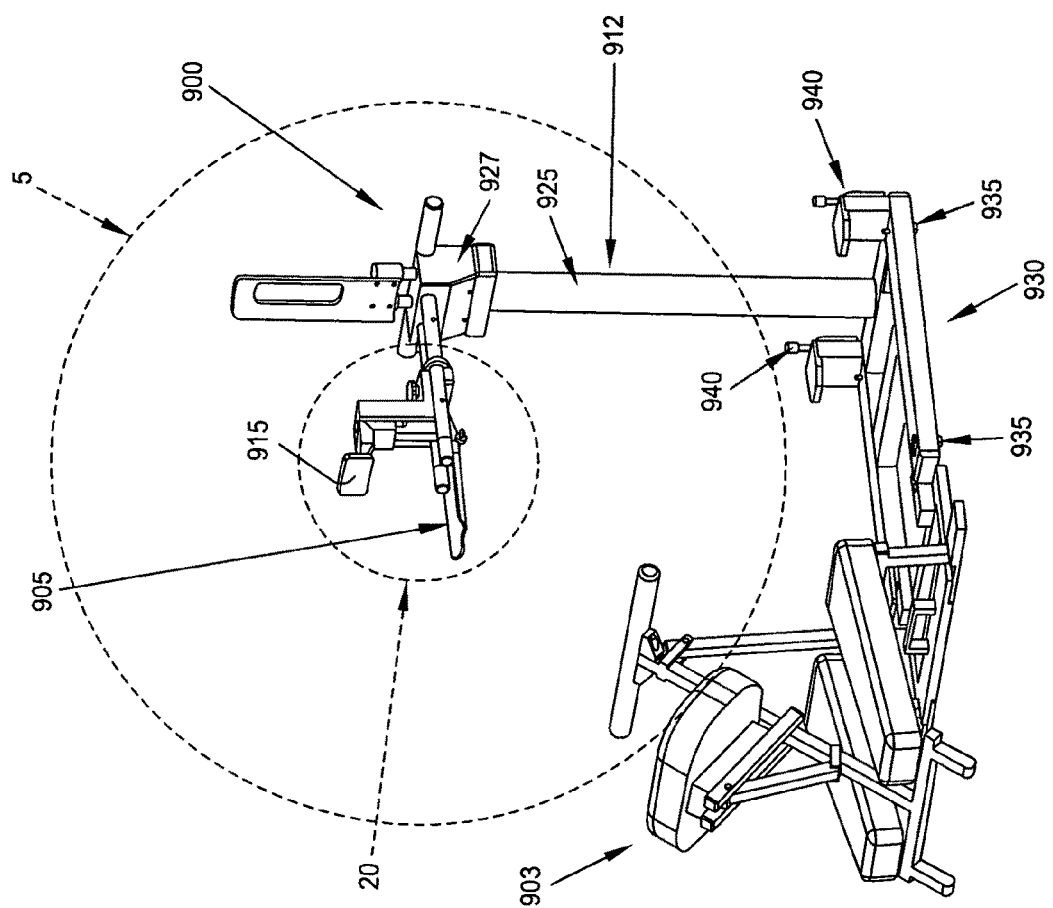
FIGS. 63-67 are schematic views showing a support for supporting anatomy of a patient (e.g., the head of a patient) during scanning.
Figure 64:
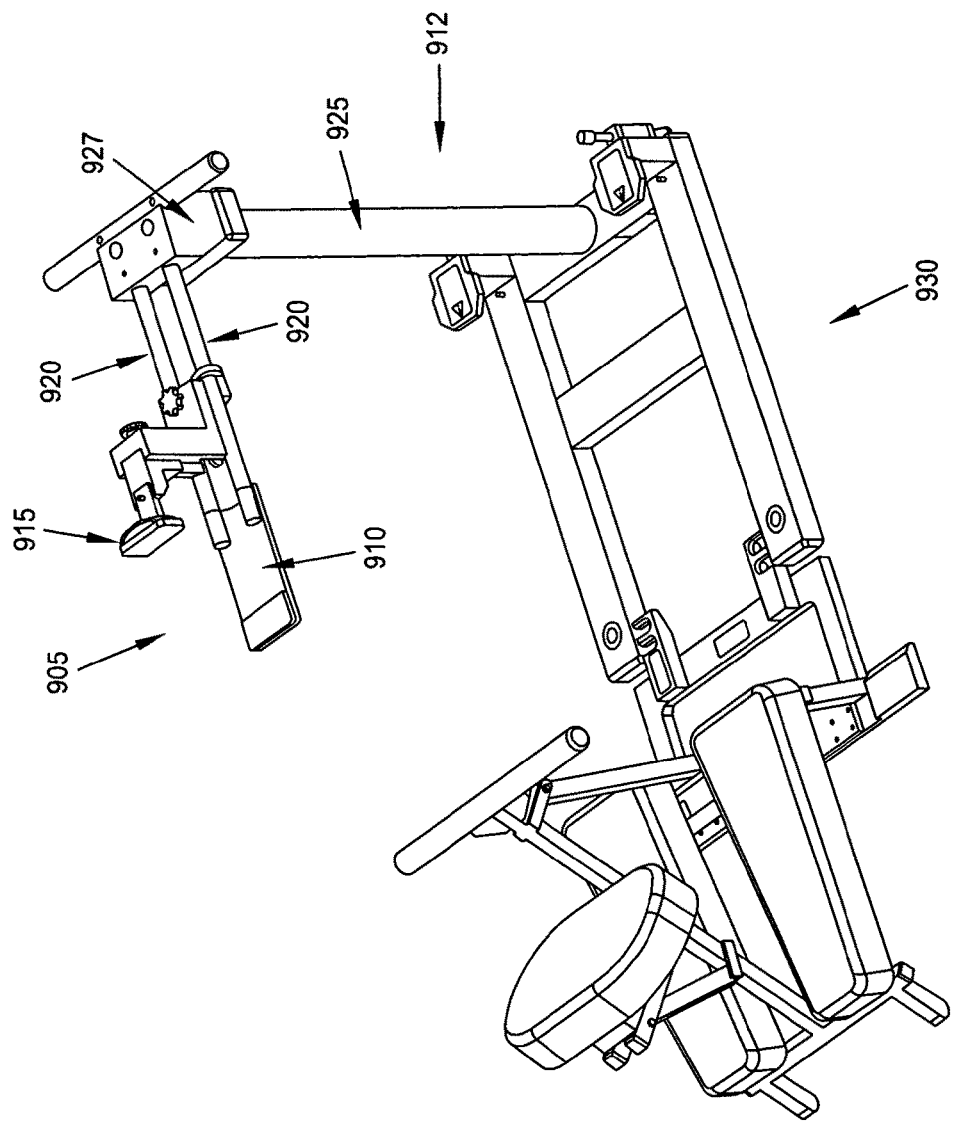
Figure 65:
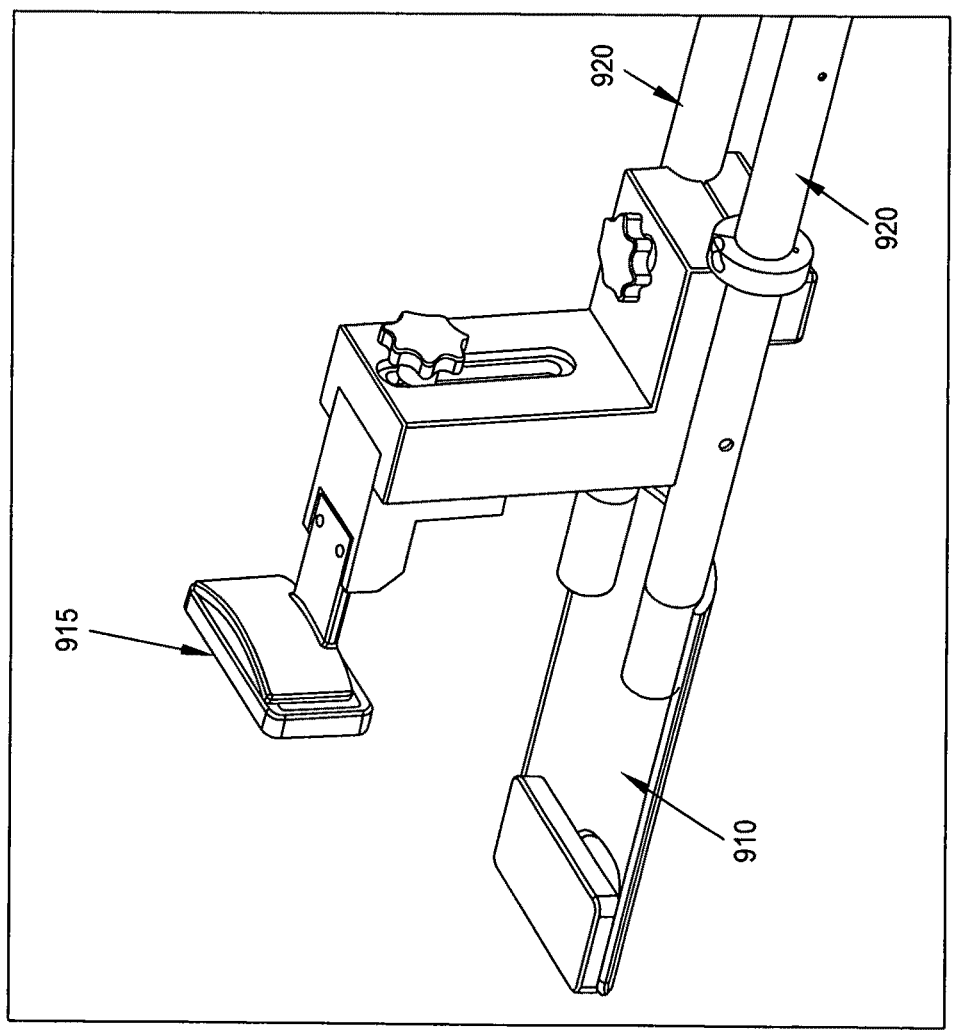
Figure 66:
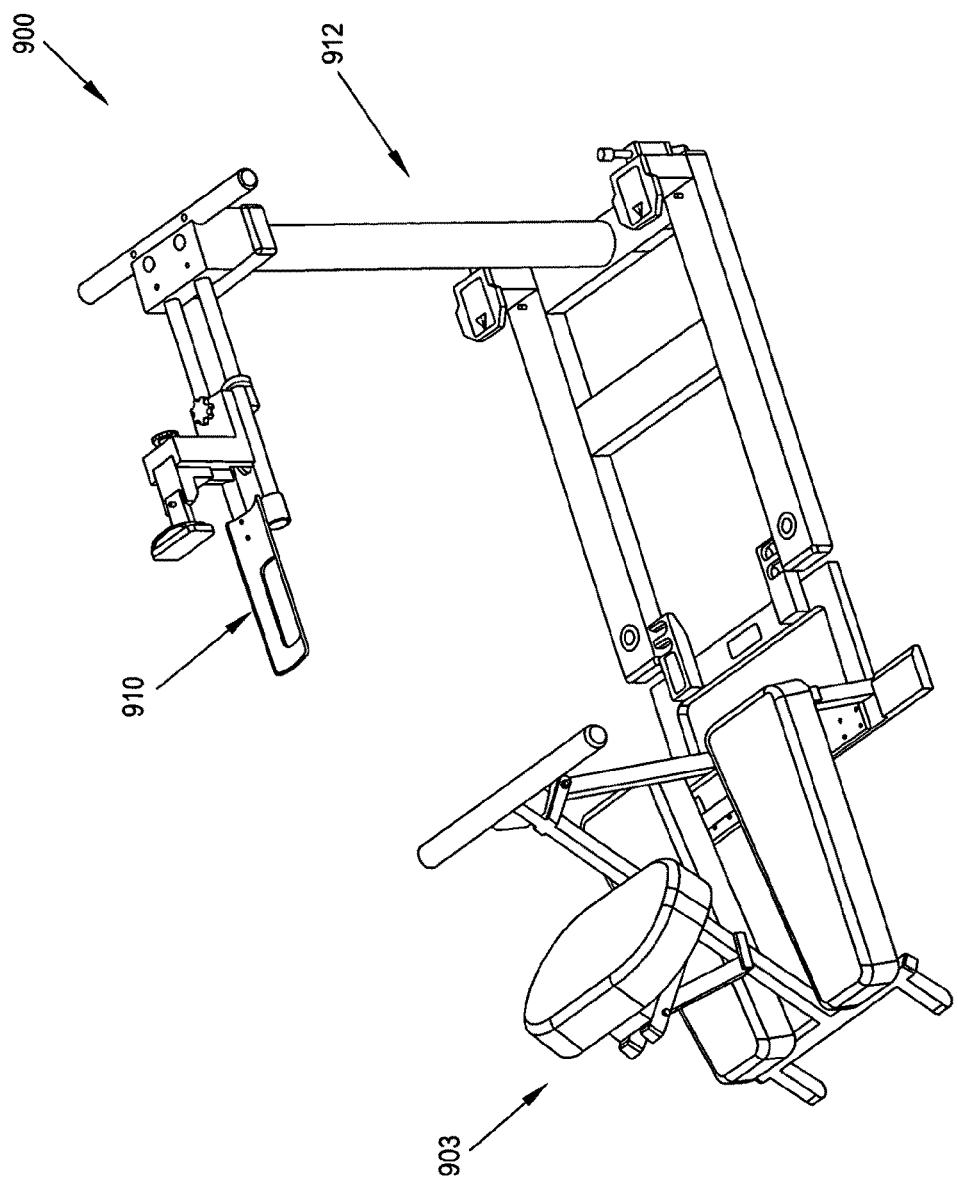
Figure 67:
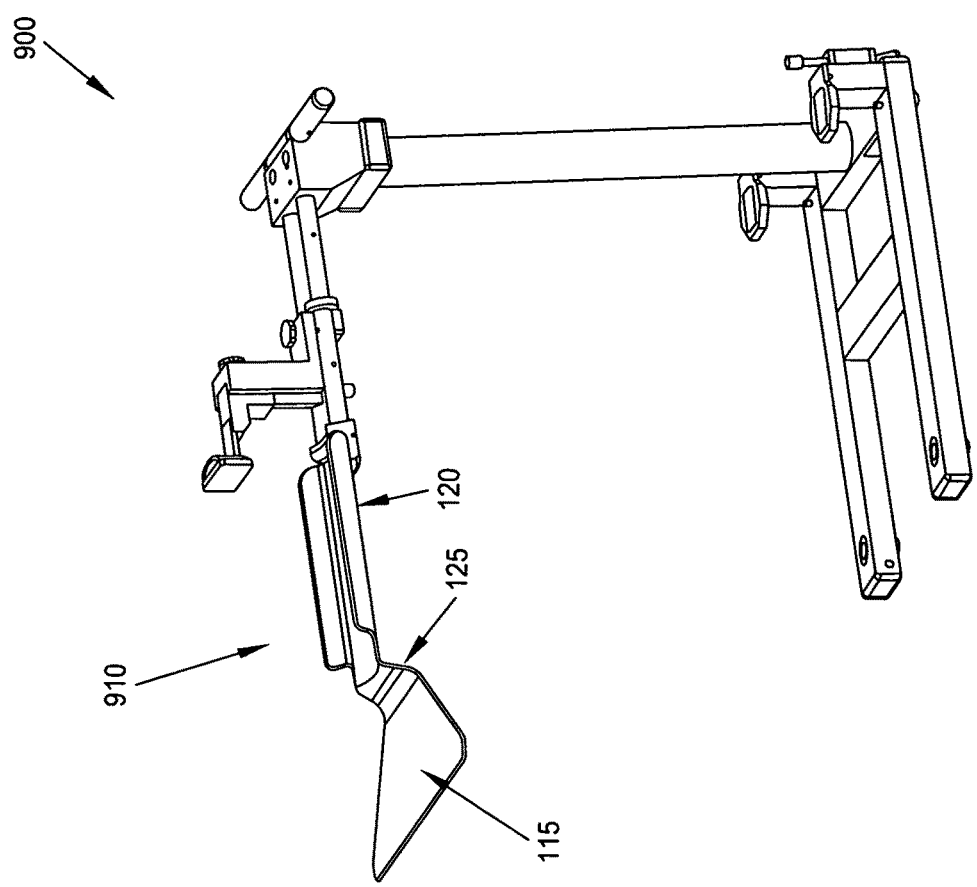
Figure 68:
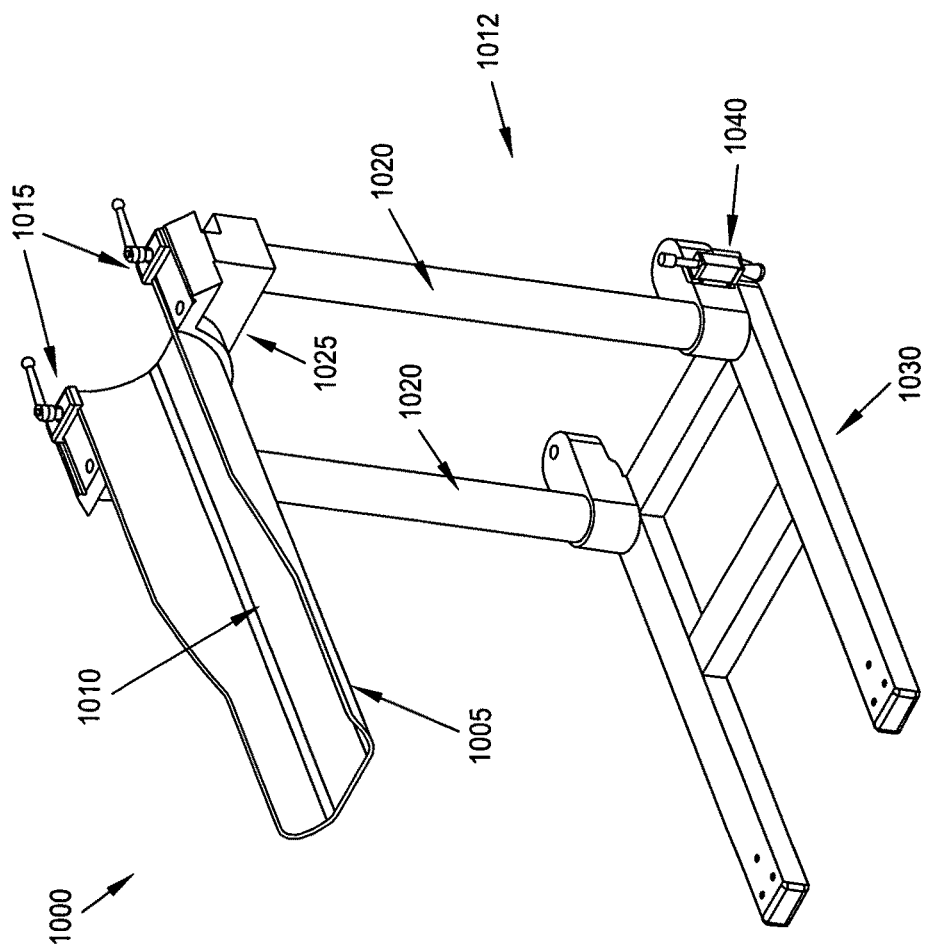
FIGS. 68-71 are schematic views showing a support for supporting anatomy of a patient (e.g., the leg of a horse) during scanning.
Figure 69:
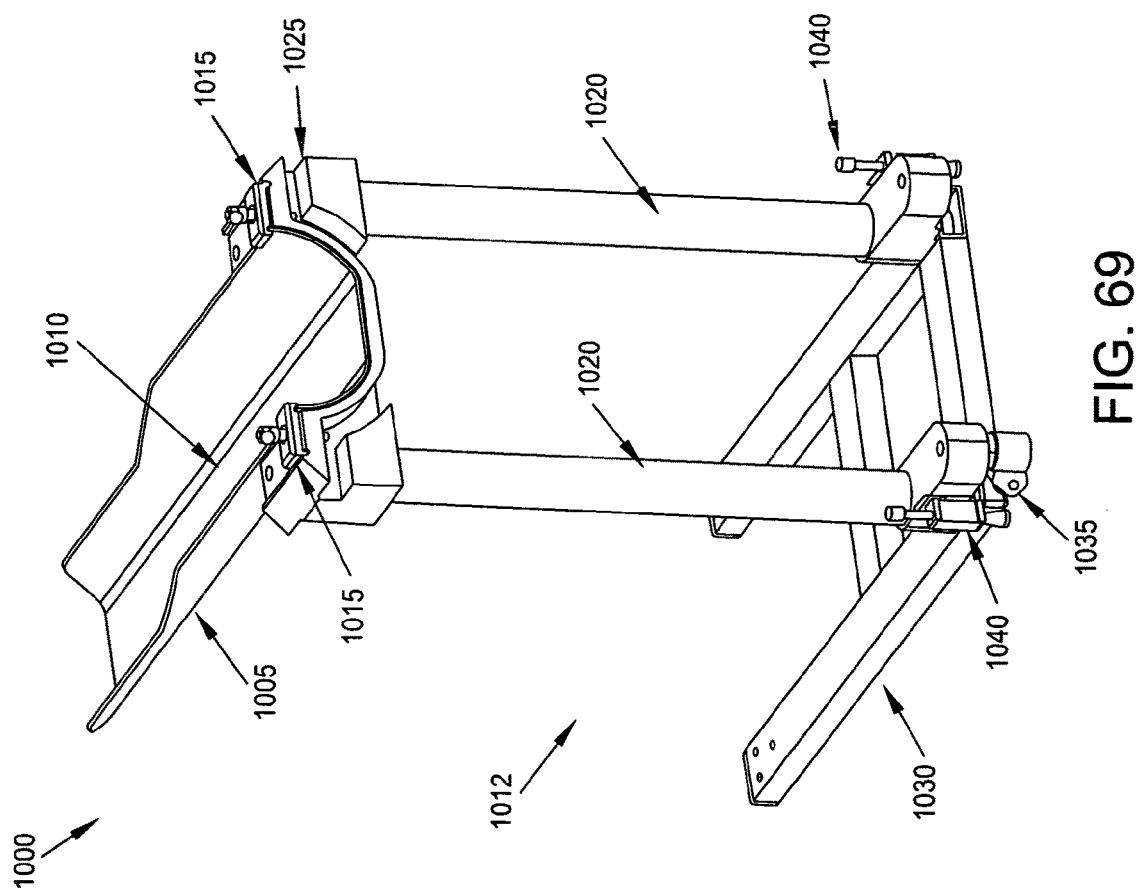
Figure 70:
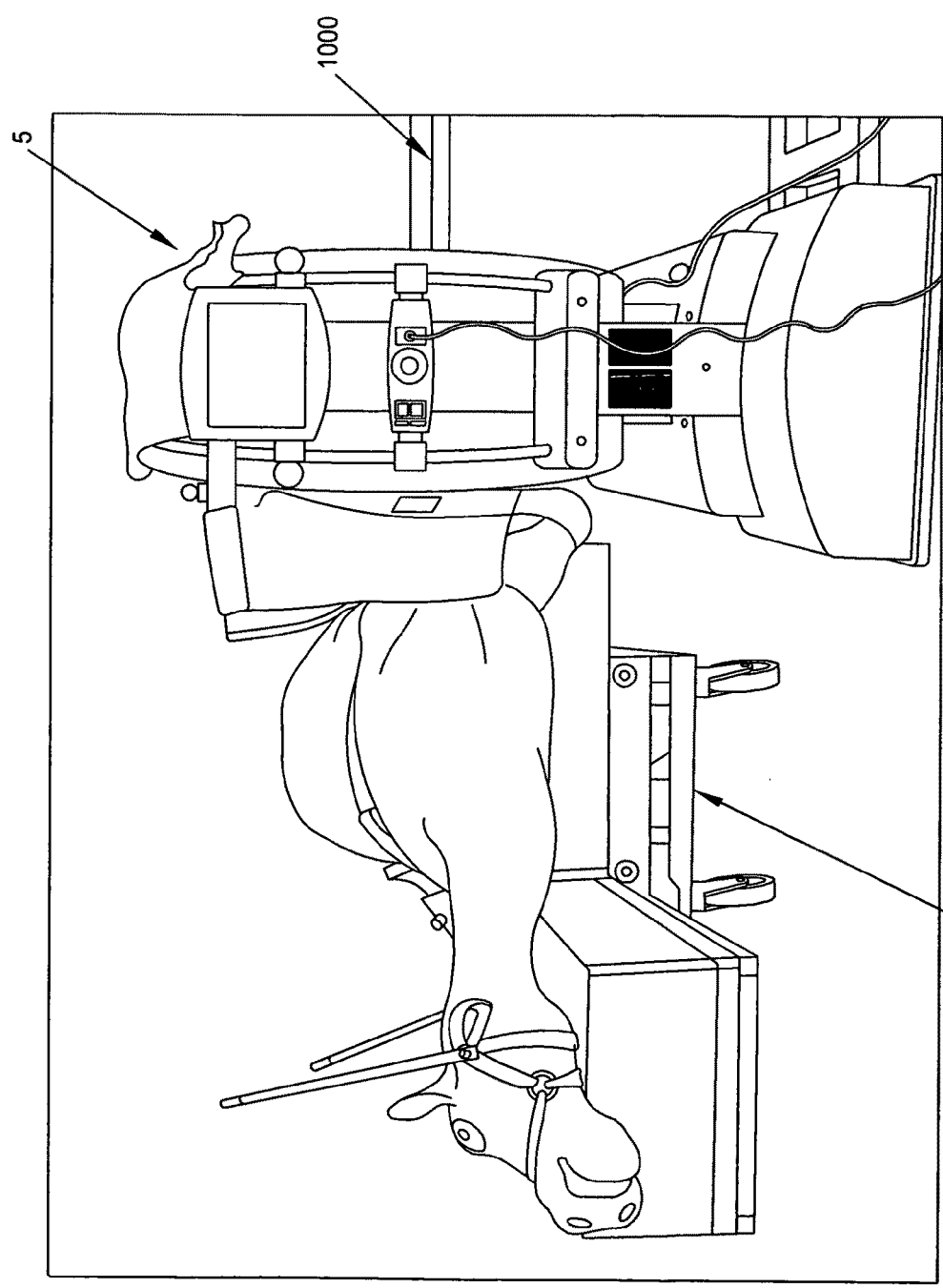
Figure 71:
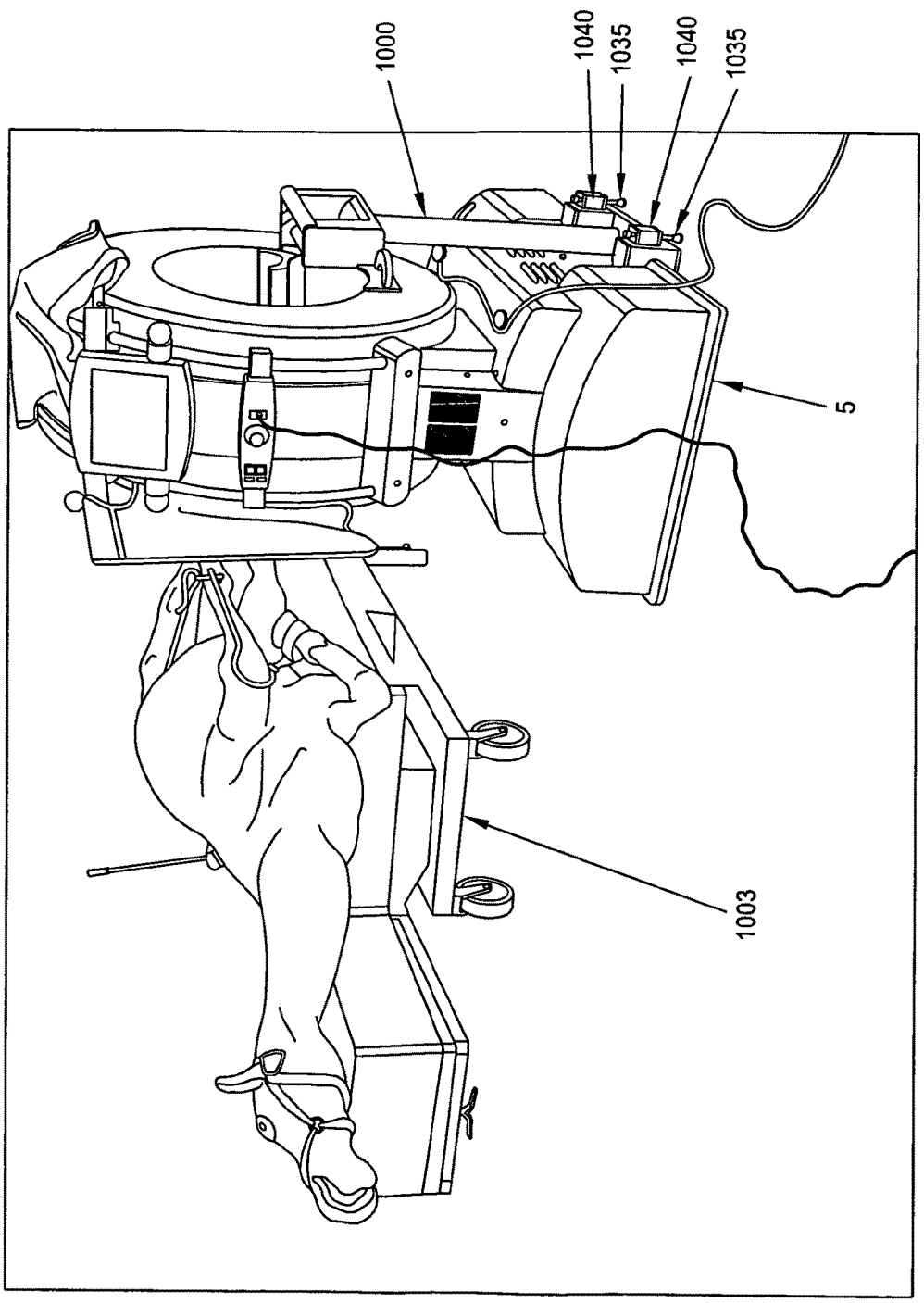

Support 800 generally comprises an X-ray transparent holder 805 and a movable stand 812. Holder 805 in turn generally comprises a main section 810 for supporting the body of the large baby or toddler, and a head section 815 for supporting the head of the large baby or toddler. Preferably, head section 815 is connected to main section 810 by a neck section 820. If desired, the leading end of main section 810 can be angled (e.g., as shown in FIGS. 58 and 61) or reduced in width (e.g., as shown in FIGS. 59, 60 and 62) in the region where main section 810 connects to neck section 820. Furthermore, if desired, head section 815 can be covered by a soft patient support PS, and/or main section 810 can be covered by a soft patient support MPS. Movable stand 812 comprises a pair of risers 825 which extend between main section 810 and a base 830. Base 830 includes casters 835 and brakes 840. Casters 835 permit support 800 to move freely across a floor, and brakes 840 allow support 800 to be stopped from moving across a floor. Support 800 is used in substantially the same way as support 700 above, except for the disposition of the large baby or infant on holder 805.

It is also possible to provide other types of support structures (e.g., a chin support) atop a movable stand so as to support the patient's anatomy during scanning.

4. ENT Support.

Thus, for example, and looking now at FIGS. 63-67, there is shown a novel support 900 which is adapted for supporting the chin of a patient (e.g., for ENT examination) during scanning. Support 900 may be used where, for example, the patient is to sit on a kneeling chair 903, with his or her chin immobilized on the support 900, for an ENT examination using CereTom™ CT machine 5. In this case, kneeling chair 903 is placed on one side of the CereTom™ CT machine 5, immediately adjacent to its center opening 20, then support 900 is positioned on the other side of the CereTom™ CT machine 5, and support 900 is then moved so that its X-ray transparent chin holder 905 extends through the center opening 20 of CereTom™ CT machine 5, whereupon the patient can sit in kneeling chair 903, place his or her chin on chin holder 905 immediately in front of the center opening 20 of the CereTom™ CT machine 5, and then scanning of the patient can be commenced.

Support 900 generally comprises the X-ray transparent chin holder 905 and a movable stand 912. Chin holder 905 in turn generally comprises an X-ray transparent main section 910 for supporting the chin of the patient, and an X-ray transparent head rest 915 for engagement by the forehead of the patient. A pair of rods 920 connect chin holder 905 to movable stand 912. More particularly, movable stand 912 comprises a riser 925 which extends between a head 927 and a base 930. Rods 920 of chin holder 905 are secured to head 927 of movable base 912. Base 930 includes casters 935 and brakes 940. Casters 935 permit support 900 to move freely across a floor, and brakes 940 allow support 900 to be stopped from moving about on the floor.

If desired, support 900 can have an alternative form of X-ray transparent main section 910. Thus, for example, in FIG. 66, another form of X-ray transparent main section 910 is provided for use in conjunction with kneeling chair 903.

Furthermore, if desired, support 900 could be fitted with a main section 910 which is generally similar to the support 105 described above, e.g., a shoulder section 115 for disposition under the shoulders of the patient and an X-ray transparent head section 120 for supporting the head of a patient, with head section 120 being connected to shoulder section 115 by a neck section 125.

It is also possible to provide support stands for veterinarian applications (e.g., to support the leg of a horse).

5. Veterinarian Support.

Thus, for example, and looking now at FIGS. 68-71, there is shown a novel support 1000 which is adapted for supporting a limb of a large animal (e.g., the leg of a horse) during scanning. Support 1000 may be used where, for example, the patient is layed on a gurney 1003, with their leg immobilized on the support 1000, for scanning of their leg using Cere-Tom™ CT machine 5. In this case, gurney 1003 is placed on one side of the CereTom™ CT machine 5, immediately adjacent to its center opening 20, then support 1000 is positioned on the other side of the CereTom™ CT machine 5, and support 1000 is then moved so that its X-ray transparent limb holder 1005 extends through the center opening 20 of Cere-Tom™ CT machine 5, whereupon the large animal on gurney 1003 can have its limb placed on the support 1000. Then scanning of the limb can be commenced.

Support 1000 generally comprises the X-ray transparent limb holder 1005 and a movable stand 1012. Limb holder 1005 in turn generally comprises an X-ray transparent main section 1010 for supporting the limb of the animal. A pair of adjustable clamps 1015 secure limb holder 1005 to movable stand 1012. More particularly, movable stand 1012 comprises a pair of risers 1020 which extend between a head 1025 and a base 1030. Base 1030 includes casters 1035 and brakes 1040. Casters 1035 permit support 1000 to move freely across a floor, and brakes 1040 allow support 1000 to be stopped from moving about on the floor.

Application to Other Types of Scanning Systems

It should be appreciated that the present invention is not limited to use with a CereTom™ CT machine 5. It may be used with any type of CT machine where the CT machine is capable of moving its scan head relative to a fixed-position patient.

Furthermore, it should be appreciated that the present invention is not limited to use with CT machines. Thus, for example, the present invention may be used in connection with CT machines used for non-medical applications, e.g., with CT machines which are used to scan inanimate objects.

Furthermore, the present invention may be used with non-CT-type scanning systems.

Thus, for example, the present invention may be used with a nuclear medicine diagnostic apparatus such as that disclosed in U.S. Pat. No. 6,285,028, issued Sep. 4, 2001 to Yamakawa for SEMICONDUCTOR RADIATION DETECTOR AND NUCLEAR MEDICINE DIAGNOSTIC APPARATUS, which patent is hereby incorporated herein by reference, wherein the diagnostic apparatus moves on rails disposed on either side of the patient.

Of course, where the present invention is used in conjunction with scanners using something other than X-rays, it may be necessary to change the composition of head section 120 so that it is rendered transparent in the scanner.

In essence, the present invention has application to any type of mobile imaging system in which the patient (or object) must be scanned on their bed or gurney (or other support).

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. Apparatus for use in scanning a patient, the apparatus comprising:
a free-standing support for supporting anatomy of a patient during scanning, the free-standing support comprising:
a holder for supporting anatomy of a patient during scanning, wherein the holder is sized so as to fit within a scan opening of a scanning machine, wherein the scan opening of the scanning machine comprises a toroidal shaped center opening, and further wherein at least a portion of the holder is transparent to the scanning machine; and
a stand, the stand comprising a shaft having a top end, a bottom end and a longitudinal axis extending therebetween, the shaft terminating in a head at the top end and a base at the bottom end;
wherein the head of the stand is configured to receive a mount formed on the holder for attaching the holder to the head so that the holder extends perpendicularly to the longitudinal axis of the shaft;
wherein the base comprises a pair of horizontal bars extending perpendicularly to the longitudinal axis of the shaft;
wherein the holder and the horizontal bars extend parallel to, but spaced from, one another so that the holder, the shaft and the pair of horizontal bars form a u-shaped configuration; and
wherein the base comprises a plurality of casters which permit the stand to move about on a floor, and at least one brake for selectively stopping movement of the stand on a floor, and further wherein the horizontal bars of the base are sized to fit under the scanning machine.

2. Apparatus according to claim 1 wherein at least the portion of the holder transparent to the scanner is formed out of an X-ray transparent material.

3. Apparatus according to claim 2 wherein the X-ray transparent material is selected from the group consisting of carbon fiber and plastic.

4. Apparatus according to claim 1 wherein at least a portion of the holder is transparent to X-rays.

5. Apparatus according to claim 1 wherein the holder is removably attached to the head of the stand.

6. Apparatus according to claim 1 wherein the apparatus further comprises a mobile scanner.

7. Apparatus according to claim 6 wherein the mobile scanner is a mobile CT machine.

8. Apparatus according to claim 7 wherein the mobile CT machine comprises a transport mechanism mounted to the base of the CT machine, wherein the transport mechanism comprises a fine movement mechanism for moving the CT machine precisely, relative to the patient, during scanning.

9. Apparatus according to claim 7 wherein the apparatus further comprises an additional free-standing support for supporting additional anatomy of a patient during scanning, the additional free-standing support comprising one from the group consisting of: a chair, a kneeling chair, a bed, a gurney, an operating table, and a patient-supporting platform.

10. Apparatus according to claim 7 wherein the free-standing support is configured to approach a scanner from a first direction and the additional free-standing support is configured to approach a scanner from a second, opposite direction.

11. A method for scanning a patient, comprising:
providing apparatus for use in scanning a patient, the apparatus comprising:
a free-standing support for supporting anatomy of a patient during scanning, the free-standing support comprising:
a holder for supporting anatomy of a patient during scanning, wherein the holder is sized so as to fit within a scan opening of a scanning machine, wherein the scan opening of the scanning machine comprises a toroidal shaped center opening, and further wherein at least a portion of the holder is transparent to the scanning machine; and
a stand, the stand comprising a shaft having a top end, a bottom end and a longitudinal axis extending therebetween, the shaft terminating in a head at the top end and a base at the bottom end;
wherein the head of the stand is configured to receive a mount formed on the holder for attaching the holder to the head so that the holder extends perpendicularly to the longitudinal axis of the shaft;
wherein the base comprises a pair of horizontal bars extending perpendicularly to the longitudinal axis of the shaft;
wherein the holder and the horizontal bars extend parallel to, but spaced from, one another so that the holder, the shaft and the pair of horizontal bars form a u-shaped configuration; and
wherein the base comprises a plurality of casters which permit the stand to move about on a floor, and at least one brake for selectively stopping movement of the stand on a floor, and further wherein the horizontal bars of the base are sized to fit under the scanning machine;
positioning the free-standing support adjacent a scanning machine, wherein the scanning machine comprises a toroidal shaped center opening;
positioning anatomy of a patient on the holder; and
moving the scanner relative to a patient during scanning while the anatomy of the patient remains disposed on the holder which is transparent to the scanning machine.

12. A free-standing support for supporting anatomy of a patient during scanning, the free-standing support comprising:
a holder for supporting anatomy of a patient during scanning, wherein the holder is sized so as to fit within a scan opening of a scanning machine, wherein the scan opening of the scanning machine comprises a toroidal shaped center opening, and further wherein at least a portion of the holder is transparent to the scanning machine; and
a stand, the stand comprising a shaft having a top end, a bottom end and a longitudinal axis extending therebetween, the shaft terminating in a head at the top end and a base at the bottom end;
wherein the head of the stand is configured to receive a mount formed on the holder for attaching the holder to the head so that the holder extends extending perpendicularly to the longitudinal axis of the shaft,
wherein the base comprises a pair of horizontal bars extending perpendicularly to the longitudinal axis of the shaft;
wherein the holder and the horizontal bars extend parallel to, but spaced from, one another so that the holder, the shaft and the pair of horizontal bars form a u-shaped configuration; and
wherein the base comprises a plurality of casters which permit the stand to move about on a floor, and at least one brake for selectively stopping movement of the stand on a floor, and further wherein the horizontal bars of the base are sized to fit under the scanning machine.

* * * * *